US007264922B2

(12) United States Patent
Welch et al.

(10) Patent No.: US 7,264,922 B2
(45) Date of Patent: Sep. 4, 2007

(54) METHOD OF REDUCING COMPLEMENT - MEDIATED DISRUPTION OF CELLS

(75) Inventors: Rodney A. Welch, Madison, WI (US); Wyndham W. Lathem, St. Louis, MO (US); Thomas E. Grys, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

(21) Appl. No.: 11/294,087

(22) Filed: Dec. 5, 2005

(65) Prior Publication Data

US 2006/0153828 A1 Jul. 13, 2006

Related U.S. Application Data

(63) Continuation-in-part of application No. 10/786,445, filed on Feb. 25, 2004, which is a continuation-in-part of application No. 10/002,309, filed on Oct. 26, 2001, now Pat. No. 6,872,559.

(60) Provisional application No. 60/651,560, filed on Feb. 10, 2005, provisional application No. 60/633,583, filed on Dec. 6, 2004, provisional application No. 60/243,675, filed on Oct. 26, 2000.

(51) Int. Cl.
*C12Q 1/00* (2006.01)
*C12N 9/48* (2006.01)

(52) U.S. Cl. .......................... 435/4; 435/69.1; 435/212; 536/23.2

(58) Field of Classification Search ..................... 435/4, 435/212, 69.1; 536/23.2
See application file for complete search history.

(56) References Cited

U.S. PATENT DOCUMENTS 6,872,559 B2   3/2005   Welch et al.

FOREIGN PATENT DOCUMENTS

WO   WO 02/34918   5/2002

OTHER PUBLICATIONS

Bauer, M.E. et al., "Characterization of an RTX toxin from enterohemorrhagic *Escherichia coli* O157:H7," Infect. Immun. (1996) 64:167-175.
Bergamaschini, L. et al., "Endothelial targeting with C1-inhibitor reduces complement activation in vitro and during ex vivo reperfusion of pig liver," Clin. Exp. Immunol. (2001) 126:412-420.
Berggard, K. et al., "Binding of human C4BP to the hypervariable region of M protein: a molecular mechanism of phagocytosis resistance in streptococcus pyogenes," Mol. Microbiol. (2001) 42:539-551.
Boucher, R.C., "An overview of the pathogenesis of cystic fibrosis lung disease," Adv. Drug Delivery Reviews (2002) 54:1359-1371.

Brunder, W., "*E. coli* 3.3kb DNA fragment from plasmid pO157," Database EMBL 'Online! Database Entry EC33P0157, Y11831.1 (1999) 1-2.
Brunder, W., "Hypothetical 34.0 kDa protein (Fragment)," Database SWALL 'Online! Entry No. Q9ZAL1 (1999) 1.
Burak, K.W. et al., "C1 inhibitor deficiency and angioedema of the small intesting masquerading as Crohn's disease," Can. J. Gastroenterol (2000) 14(4):349-351.
Burland, V. et al., "The complete DNA sequence and analysis of the large virulence plasmic of *Escherichia coli* 0157:H7 plasmid pO157, complete sequence," Database EMBL 'Online! Database Entry AF074613 (1998) 1-54.
Burland, V. et al., "The complete DNA sequence and analysis of the large virulence plasmic of *Escherichia coli* 0157:H7," Nucleic Acids Res. (1998) 26(18):4196-4204.
Cai, S. et al., "Complement regulatory protein C1 inhibitor binds to selectins and interferes with endothelial-leukocyte adhesion," J. Immunol. (2003) 171:4786-4791.
Caldwell, E.E. et al., "Heparin binding and augmentation of C1 inhibitor activity," Arch. Biochem. Biophys. (1999) 361:215-222.
Caliezi, C. et al., "C1-esterase inhibitor: an anti-inflammatory agent and its potential use in the treatment of diseases other than hereditary angioedema," Pharmacol. Rev. (2000) 52:91-112.
Caprioli, A. et al., "Pheno-genotyping of verotoxin 2 (VT2)-producing *Escherichia coli* causing haemorrhagic colitis and haemolytic uraemic syndrome by direct analysis of patients' stools," J. Med. Microbiol. (1995) 43:348-353.
Catanese, J. et al., "Enzymatic intactivation of human plasma C1-inhibitor and alpha1 antichymotrypsin by pseudomonas aeruginosa proteinase and elastase," Biochim. Biophys. Acta (1984) 789:37-43.
Chan, J.Y. et al., "The inhibition of activated factor XII (Hageman factor) by antithrombin III: the effect of other plasma proteinase inhibitors," Biochim Biophys. Res. Commun. (1977) 74:150-158.
Cooper, N.R., "Complement evasion strategies of microorganisms," Immunol. Today (1991) 12:327-331.
Coutinho, M. et al., "Functional analysis of the serpin domain of C1 inhibitor," J. Immunol. (1994) 153:3648-3654.
Datsenko et al., "One-step inactivation of chromosomal genes in *Escherichia coli* K-12 using PCR products," PNAS (2000) 97:6640-6645.
De Agostini, A. et al., "Human plasma kallikrein and C1 inhibitor form a complex possessing an epitope that is not detectable on the parent molecules: demonstration using a monoclonal antibody," PNAS (1985) 82:5190-5193.
De Lorenzo, V.D. et al., "Analysis and construction of stable phenotypes in gram-negative bacteria with Tn5- and Tn10-derived minitransposons," Bacterial Pathogenesis, Clark & Bavoil, eds., Academic Press, San Diego (1994) 235:386-405.

(Continued)

*Primary Examiner*—Tekchand Saidha
(74) *Attorney, Agent, or Firm*—Michael Best & Friedrich LLP

(57) ABSTRACT

Disclosed is a pO157 plasmid-specified polypeptide found in *E. coli* EDL933 and other *E. coli* that binds to and cleaves C1-esterase inhibitor, and antibodies specific for the polypeptide. Also disclosed are methods employing the polypeptide for diagnosing enterohemorrhagic *E. coli* infection, identifying potential inhibitors of its activity, and reducing viscosity of material containing glycosylated polypeptides.

3 Claims, 23 Drawing Sheets

OTHER PUBLICATIONS

Dean-Nystrom, E. et al., "Vaccination of pregnant dams with intimin O157 protects suckling piglets from *Escherichia coli* O157:H7 infection," Inf. Immun. (2002) 70(5):2414-2418.

Deloney et al., "Role for phosphoglucomutase in vibrio fischeri-euprymna scolopes symbiosis," J. Bacteriol. (2002) 184(18):5121-5129.

Donnenberg, M.S. et al., "Methods for studying adhesion of diarrheagenic *Escherichia coli*," Meth. Enzym. (1992) 253:324-327.

Elson, C. et al., "Generalized systemic and mucosal immunity in mice after mucosal stimulation with cholera toxin," J. Immun. (1984) 132(6):2736-2741.

Elson, C. et al., "Cholera toxin feeding did not induce oral tolerance in mice and abrogated oral tolerance to an unrelated protein antigen," J. Immunol. (1984) 133(6):2892-2897.

Eriksson, K. et al., "Cholera toxin and its B subunit promote dendritic cell vaccination with different influences on Th1 and Th2 development," Inf. Immun. (2003) 71(4):1740-1747.

Frank, M.M. et al., "Complement," Fundamental Immunology, W.E. Paul, ed., Raven Press, NY (1989).

Frank, M.M., "The mechanism by which microorganisms avoid complement attack," Curr. Opin. Immunol. (1992) 4:14-19.

Frankel, G. et al., "Enteropathogenic and enterohaemorrhagic *Escherichia coli*: more subversive elements," Mol. Microbiol. (1998) 30:911-921.

Gadek, J.E. et al., "Replacement therapy in hereditary angioedema. Successful treatment of acute episodes of angioedema with partly purified C1 inhibitor," N. Engl. J. Med. (1980) 302:542-546.

Gigli, I. et al., "Modulation of the classical pathway C3 convertase by plasma proteins C4 binding protein and C3b inactivator," PNAS (1979) 76:6596-6600.

Grys, T.E. et al., "The StcE protease contributes to intimate adherence of enterohemorrhagic *Escherichia coli* O157:H7 to host cells," Inf. Immun. (2005) 73(3):1295-1303.

Harlow, E. et al., Antibodies: A Laboratory Manual, Cold Spring Harbor Laboratory Press, Cold Spring Harbor (1988).

Hauert, J. et al., "C1 inhibitor cross-linking by tissue transglutaminase," J. Biol. Chem. (2000) 275:14558-14562.

Hellwage, J. et al., "The complement regulator factor H binds to the surface protein OspE of borrelia burgdorferi," J. Biol. Chem. (2001) 276:8427-8435.

Hong, Y.Q. et al, "Effect of pseudomonas aeruginosa elastase and alkaline protease on serum complement and isolated components C1q and C3," Clin. Immun. Immunopath. (1992) 62:133-138.

Huntington, J.A. et al., "Structure of a serpin-protease complex shows inhibition by deformation," Nature (2000) 407:923-926.

Jiang, H. et al., "Complement 1 inhibitor is a regulator of the alternative complement pathway," J. Exp. Med. (2001) 194:1609-1616.

Jiang, W. et al., "Families of metalloendopeptidases and their relationships," FEBS Letters (1992) 312:110-114.

Judge, N. et al., "Plant cell-based intimin vaccine given orally to mice primed with intimin reduces time of *Escherichia coli* O157:H7 shedding in feces," Inf. Immun. (2004) 72(1):168-175.

Jung, C.-M. et al., "Identification of metal ligands in the clostridium histolyticum ColH collagenase," J. Bact. (1999) 181:2816-2822.

Karmali, M.A. et al., "Sporadic cases of haemolytic-uraemic syndrome associated with faecal cytotoxin and cytotoxin-producing *Escherichia coli* in stools," Lancet (1983) 1:619-620.

Knutton, S. et al., "Actin accumulation at sites of bacterial adhesion to tissue culture cells: basis of a new diagnostic test for enteropathogenic and enterohemorrhagic *Escherichia coli*," Inf. Immun. (1989) 1290-1298.

Kuno, K. et al., "ADAMTS-1 is an active metalloproteinase associated with the extracellular matrix," J. Biol. Chem. (1999) 274:18821-18826.

Lathem, W.W. et al, "StcE, a metalloprotease secreted by *Escherichia coli* O157:H7, specifically cleaves C1 esterase inhibitor," Mol. Microbiol. (2002) 45:277-288.

Lathem, W.W. et al., "A novel metalloprotease secreted by *Escherichia coli* O157HH7 cleaves C1 esterase inhibitor, a regulator of multiple proteolytic cascades,", Abstracts of the General Meeting of the American Society for Microbiology, Washington, DC (May 20-24, 2001) 101:113.

Lathem, W.W. et al., "Acquisition of StcE, a C1 esterase nihibitor-specific metalloprotease, during the evolution of *Escherichia coli* O157:H7," J. Infect. Dis. (2003) 187(12):1907-1914.

Lathem, W.W. et al., "Potentiation of C1 esterase inhibitor by StcE, a metalloprotease secreted by *Escherichia coli* 0157:H7," J. Exp. Med. (2004) 199(8):1077-1087.

Lee, G. et al., "Tau interacts with src-family non-receptor tyrosine kinases," J. Cell Sci. (1998) 111:3167-3177.

Li, Y. et al., "Human response to *Escherichia coli* O157:H7 infection: antibodies to secreted virulence factors," Inf. Immun. (2000) 68(9):5090-5095.

Makino et al., "Complete nucleotide sequences of 93-kb and 3.3-kb plasmics of an enterohemorrhagic *Escherichia coli* O157:H7 derived from sakai outbreak," DNA Research (1998) 5:1-9, {including sequence search alignment between T43121 and Seq ID No. 2}.

Matsunami, K. et al., "A surface-bound form of human C1 esterase inhibitor improves xenograft rejection," Transplantation (2000) 69:749-755.

Mayer, M.M., Experimental Immunochemistry, Kabat and Mayer, eds., Thomas, Springfield, IL (1961).

Minta, J.O., "The role of sialic acid in the functional activity and the hepatic clearance of C1-INH," J. Immunol. (1981) 126:245-249.

Molla, A. et al., "Inactivation of various proteinases inhibitors and the complement system in human plasma by the 56-kiladalton proteinase from serratia marcescens," Infect. Immun. (1989) 57:1868-1871.

Nataro, J.P. et al., "Diarrhaegenic *Escherichia coli*," Clin. Microbiol. Rev. (1998) 11:142-201.

Oda, T. et al., "Inactivation of chemotactic activity of C5a by the serratial 56-kilodalton protease," Infec. Immun. (1990) 58:1269-1272.

O'Farrell, P.H., "High resolution two-dimensional electrophoresis of proteins," J. Biol. Chem. (1975) 250:4007-4021.

Paton, A.W. et al., "Reactivity of convalescent-phase hemolytic-uremic syndrome patient sera with the megaplasmid-encoded TagA protein of shiga toxigenic *Escherichia coli* O157," J. Clin. Microbiol (2002) 40:1395-1399.

Patston, P.A. et al., "Regulation of C1-inhibitor function by binding to type IV collagen and heparin," Biochem. Biophys. Res. Commun. (1997) 230:597-601.

Patston, P.A. et al., "The effect of cleavage by a crotalus atrox alpha-proteinase fraction on the properties of C1-inhibitor," Toxicon (1995) 33:53-61.

Pensky, J. et al., "Human serum inhibitor of C'1 esterase: identity with alpha-2-neuraminoglycoprotein," Science (1969) 163:698-699.

Perna, N.T. et al., "Genome sequence of enterohaemorrhagic *Escherichia coli* 0157:H7," Nature (2001) 409:529-533.

Pierce, N.F., "The role of antigen form and function in the primary and secondary intestinal immune responses to cholera toxin and toxoid in rats," J. Exp. Med. (1978) 195-206.

Pixley, R.A. et al., "The regulation of human factor XIIa by plasma proteinase inhibitors," J. Biol. Chem. (1985) 260:1723-1729.

Plunkett, G. et al., "Sequence of shiga toxin 2 phage 933W from *Escericha coli* O157:H7: shiga toxin as a phage late-gene product," J. Bacteriol. (1999) 181:1767-1778.

Potempa, J. et al., "The serpin superfamily of proteinase inhibitors: structure, function and regulation," J. Biol. Chem. (1994) 269:15957-15960.

Potter, A. et al., "Decreased shedding of *Escherichia coli* O157:H7 by cattle following vaccination with type III secreted proteins," Vaccine (2004) 22:362-369.

Poulle, M. et al., "Large-scale preparation of highly purified human C1-inhibitor for therapeutic use," Blood Coagulation & Fibrinolysis (1994) 5:543-549.

Roesch, P.L. et al., "Leucine alters the interaction of the leucine-responsive regulatory protein (Lrp) with the fim switch to stimulate site-specific recombination in *Escherichia coli*," Mol. Microb. (1998) 27:751-761.

Schapira, M. et al., "Contribution of plasma protease inhibitors to the inactivation of kallikrein in plasma," J. Clin. Invest (1982) 69:462-468.

Schmaier, A.H. et al., "Expression of platelet C1 inhibitor," Blood (1993) 82:465-474.

Schmaier, A.H. et al., "Synthesis and expression of C1 inhibitor by human umbilical vein endothelial cells," J. Biol. Chem. (1989) 264:18173-18179.

Sequence search alignment between Q9ZAL1 (May 1, 1999) and SEQ ID No. 2 (residue 24-886).

Shreedhar, V. et al., "Cholera toxin induces migration of dendritic cells from the subepithelial dome region to T- and B-cell areas of peyer's patches," Inf. Immun. (2003) 71(1):504-509.

Siegler, R.L., "The hemolytic uremic syndrome," Pediatric Nephrology (1995) 42:1505.

Sim, R.B. et al., "Interaction of I125-labelled complement subcomponents C1r and C1s with protease inhibitors in plasma," FEBS Lett. (1979) 97-111-115.

Storm, D. et al., "C1 inhibitor-C1s complexes are internalized and degraded by the low density lipoprotein receptor-related protein," J. Biol. Chem. (1997) 272:31043-31050.

Te Loo, D.M. et al., "Binding and transfer of verocytotoxin by polymorphonuclear leukocytes in hemolytic uremic syndrome," Blood (2000) 95:3396-3402.

Te Loo, D.M. et al., "Detection of verocytotoxin bound to circulating polymorphonuclear leukocytes of patients with hemolytic uremic syndrome," J. Am. Soc. Nephrol. (2001) 12:800-806.

Thern, A. et al., "Ig-binding surface proteins of streptococcus pyogenes also bind human C4b-binding protein (C4BP), a regulatory component of the complement system," J. Immunol. (1995) 154:375-386.

Van Den Berg, R.H. et al., "Regulation of the function of the first component of complement by human C1q receptor," Eur. J. Immunol. (1995) 25:2206-2210.

Van Der Graaf, F. et al., "Inactivation of kallikrein in human plasma," J. Clin. Invest. (1983) 71:149-158.

Waytes, A.T. et al., "Treatment of hereditary angioedema with a vapor-heated C1 inhibitor concentrate," N. Engl. J. Med. (1996) 334:1630-1634.

Weiler, J.M. et al, "Control of the amplification convertase of complement by the plasma protein beta1H," PNAS (1976) 73:3268-3272.

Witowski, S.E. et al., "StcE, a novel metalloprotease from enterohemorrhagic *Escherichia coli*, is specific for pO157-containing strains of diarrheagenic *E. coli*," Abstracts of the General Meeting of the American Society for Microbiology, Washington DC (May 20-24, 2001) 101:113.

Wuillemin, W.A. et al, "Inactivation of factor Xia in human plasma assessed by measuring factor Xia-protease inhibitor complexes: major role of C1-inhibitor," Blood (1995) 85:1517-1526.

Wuillemin, W.A. et al., "Modulation of contact system proteases by glycosaminoglycans. Selective enhancement of the inhibition of factor Xia," J. Biol. Chem. (1996) 271:12913-12918.

Lysates of *E. coli* strains containing pO157 induce the aggregation of Jurkat cells, while non-pO157-containing *E. coli* lysates do not aggregate the same cells.

Purification of StcE-His from WAM2572

StcE is produced by strains of *E. coli* that carry pO157 but not in strains that lack pO157 or have a transposon insertion in *stcE*.

A)  B)

StcE – His interacts with a human serum protein(s) of approximately 105 kDa.

Figure 5. StcE-His cleaves C1 inhibitor in human serum.

Differential digestion patterns of C1-INH by StcE-His and *P. aeruginosa* elastase.

Detection of StcE in fecal filtrates from children with diarrhea.

StcE E435D-His lacks proteolytic activity against and the ability to bind to C1-INH.

Figure 9. PCR analysis of *stcE* in the DEC collection.

Detection of StcE in bacterial-conditioned culture supernatants.

Detection of C1-INH proteolytic activity in bacterial-conditioned culture supernatants.

A)

B)

SEQUENCE LISTING

```
<160> NUMBER OF SEQ ID NOS: 25

<210> SEQ ID NO 1
<211> LENGTH: 2798
<212> TYPE: DNA
<213> ORGANISM: Unknown
<220> FEATURE:
<223> OTHER INFORMATION: Description of Unknown Organism: E. coli
      O157:H7 plasmid pO157
<220> FEATURE:
<221> NAME/KEY: CDS
<222> LOCATION: (138)..(2798)
<223> OTHER INFORMATION:

<400> SEQUENCE: 1
tttacgaaac aggtgtaaat atgttataaa ataaccaac gactagtgaa taagtcgctc        60
ctgaaaaaat aaaatataga aatactgtta tatccggctg catgaacact aaaatgaatg       120
agagatggag aacaccg atg aaa tta aag tat ctg tca tgt acg atc ctt         170
                   Met Lys Leu Lys Tyr Leu Ser Cys Thr Ile Leu
                    1               5                  10 gcc cct ctg gcg att ggg gta ttt tct gca aca gct gct gat aat aat        218
Ala Pro Leu Ala Ile Gly Val Phe Ser Ala Thr Ala Ala Asp Asn Asn
            15                  20                  25 tca gcc att tat ttc aat acc tcc cag cct ata aat gat ctg cag ggt        266
Ser Ala Ile Tyr Phe Asn Thr Ser Gln Pro Ile Asn Asp Leu Gln Gly
        30                  35                  40 tcg ttg gcc gca gag gtg aaa ttt gca caa agc cag att tta ccc gcc        314
Ser Leu Ala Ala Glu Val Lys Phe Ala Gln Ser Gln Ile Leu Pro Ala
    45                  50                  55 cat cct aaa gaa ggg gat agt caa cca cat ctg acc agc ctg cgg aaa        362
His Pro Lys Glu Gly Asp Ser Gln Pro His Leu Thr Ser Leu Arg Lys
60                  65                  70                  75 agt ctg ctg ctt gtc cgt ccg gtg aaa gct gat gat aaa aca cct gtt        410
Ser Leu Leu Leu Val Arg Pro Val Lys Ala Asp Asp Lys Thr Pro Val
                80                  85                  90 cag gtg gaa gcc cgc gat gat aat aat aaa att ctc ggt acg tta acc        458
Gln Val Glu Ala Arg Asp Asp Asn Asn Lys Ile Leu Gly Thr Leu Thr
            95                 100                 105 ctt tat cct cct tca tca cta ccg gat aca atc tac cat ctg gat ggt        506
Leu Tyr Pro Pro Ser Ser Leu Pro Asp Thr Ile Tyr His Leu Asp Gly
        110                 115                 120 gtt ccg gaa ggt ggt atc gat ttc aca cct cat aat gga acg aaa aag        554
Val Pro Glu Gly Gly Ile Asp Phe Thr Pro His Asn Gly Thr Lys Lys
    125                 130                 135 atc att aat acg gtg gct gaa gta aac aaa ctc agt gat gcc agc ggg        602
Ile Ile Asn Thr Val Ala Glu Val Asn Lys Leu Ser Asp Ala Ser Gly
140                 145                 150                 155
```

```
agt tct att cat agc cat cta aca aat aat gca ctg gtg gag atc cat    650
Ser Ser Ile His Ser His Leu Thr Asn Asn Ala Leu Val Glu Ile His
            160                 165                 170 act gca aat ggt cgt tgg gta aga gac att tat ctg ccg cag gga ccc    698
Thr Ala Asn Gly Arg Trp Val Arg Asp Ile Tyr Leu Pro Gln Gly Pro
        175                 180                 185 gac ctt gaa ggt aag atg gtt cgc ttt gtt tcg tct gca ggc tat agt    746
Asp Leu Glu Gly Lys Met Val Arg Phe Val Ser Ser Ala Gly Tyr Ser
    190                 195                 200 tca acg gtt ttt tat ggt gat cga aaa gtc aca ctc tcg gtg ggt aac    794
Ser Thr Val Phe Tyr Gly Asp Arg Lys Val Thr Leu Ser Val Gly Asn
205                 210                 215 act ctt ctg ttc aaa tat gta aat ggt cag tgg ttc cgc tcc ggt gaa    842
Thr Leu Leu Phe Lys Tyr Val Asn Gly Gln Trp Phe Arg Ser Gly Glu
220                 225                 230                 235 ctg gag aat aat cga atc act tat gct cag cat att tgg agt gct gaa    890
Leu Glu Asn Asn Arg Ile Thr Tyr Ala Gln His Ile Trp Ser Ala Glu
                240                 245                 250 ctg cct gcg cac tgg atc gtg cct ggt tta aac ttg gtg att aaa cag    938
Leu Pro Ala His Trp Ile Val Pro Gly Leu Asn Leu Val Ile Lys Gln
            255                 260                 265 ggc aat ctg agc ggt cgc cta aat gat atc aag att gga gca ccg ggt    986
Gly Asn Leu Ser Gly Arg Leu Asn Asp Ile Lys Ile Gly Ala Pro Gly
        270                 275                 280 gag ctg ttg ttg cat aca att gat atc ggg atg ttg acc act ccc cgg   1034
Glu Leu Leu Leu His Thr Ile Asp Ile Gly Met Leu Thr Thr Pro Arg
    285                 290                 295 gat cgc ttt gat ttt gcc aaa gac aaa gaa gca cat agg gaa tat ttc   1082
Asp Arg Phe Asp Phe Ala Lys Asp Lys Glu Ala His Arg Glu Tyr Phe
300                 305                 310                 315 cag acc att cct gta agt cgt atg att gtt aat aat tat gcg cct cta   1130
Gln Thr Ile Pro Val Ser Arg Met Ile Val Asn Asn Tyr Ala Pro Leu
                320                 325                 330 cac cta aag gaa gtt atg tta cca acc gga gag tta ttg aca gat atg   1178
His Leu Lys Glu Val Met Leu Pro Thr Gly Glu Leu Leu Thr Asp Met
            335                 340                 345 gat cca gga aat ggt ggg tgg cat agt ggt aca atg cgt caa aga ata   1226
Asp Pro Gly Asn Gly Gly Trp His Ser Gly Thr Met Arg Gln Arg Ile
        350                 355                 360 ggt aaa gaa ttg gtt tcg cat ggc att gat aat gct aac tat ggt tta   1274
Gly Lys Glu Leu Val Ser His Gly Ile Asp Asn Ala Asn Tyr Gly Leu
    365                 370                 375 aat agt acc gca ggc tta ggg gag aat agt cat cca tat gta gtt gcg   1322
Asn Ser Thr Ala Gly Leu Gly Glu Asn Ser His Pro Tyr Val Val Ala
380                 385                 390                 395 caa tta gcg gca cat aat agc cgc ggt aat tat gct aat ggc atc cag   1370
Gln Leu Ala Ala His Asn Ser Arg Gly Asn Tyr Ala Asn Gly Ile Gln
                400                 405                 410 gtt cat ggt ggc tcc gga ggt ggg gga att gtt act tta gat tcc aca   1418
Val His Gly Gly Ser Gly Gly Gly Gly Ile Val Thr Leu Asp Ser Thr
            415                 420                 425 ttg ggg aat gag ttc agt cat gaa gtt ggt cat aat tat ggt ctt ggt   1466
Leu Gly Asn Glu Phe Ser His Glu Val Gly His Asn Tyr Gly Leu Gly
        430                 435                 440 cat tat gta gat ggt ttc aag ggt tct gta cat cgt agt gca gaa aat   1514
His Tyr Val Asp Gly Phe Lys Gly Ser Val His Arg Ser Ala Glu Asn
    445                 450                 455 aac aac tca act tgg gga tgg gat ggt gat aaa aaa cgg ttt att cct   1562
Asn Asn Ser Thr Trp Gly Trp Asp Gly Asp Lys Lys Arg Phe Ile Pro
460                 465                 470                 475
```

```
aac ttt tat ccg tct caa aca aat gaa aag agt tgt ctg aat aat cag    1610
Asn Phe Tyr Pro Ser Gln Thr Asn Glu Lys Ser Cys Leu Asn Asn Gln
                480                 485                 490 tgt caa gaa ccg ttt gat gga cac aaa ttt ggt ttt gac gcc atg gcg    1658
Cys Gln Glu Pro Phe Asp Gly His Lys Phe Gly Phe Asp Ala Met Ala
            495                 500                 505 gga ggc agc cct ttc tct gct gca aac cgt ttc aca atg tat act ccg    1706
Gly Gly Ser Pro Phe Ser Ala Ala Asn Arg Phe Thr Met Tyr Thr Pro
        510                 515                 520 aat tca tcg gct atc atc cag cgt ttt ttt gaa aat aaa gct gtg ttc    1754
Asn Ser Ser Ala Ile Ile Gln Arg Phe Phe Glu Asn Lys Ala Val Phe
    525                 530                 535 gat agc cgt tcc tcc acc ggc ttc agc aag tgg aat gca gat acg cag    1802
Asp Ser Arg Ser Ser Thr Gly Phe Ser Lys Trp Asn Ala Asp Thr Gln
540                 545                 550                 555 gaa atg gaa ccg tat gaa cac acc att gac cgt gcg gag cag att acg    1850
Glu Met Glu Pro Tyr Glu His Thr Ile Asp Arg Ala Glu Gln Ile Thr
                560                 565                 570 gct tca gtc aat gag cta agt gaa agc aaa atg gct gag ctg atg gca    1898
Ala Ser Val Asn Glu Leu Ser Glu Ser Lys Met Ala Glu Leu Met Ala
            575                 580                 585 gag tac gct gtc gtc aaa gtg cat atg tgg aac ggt aac tgg aca aga    1946
Glu Tyr Ala Val Val Lys Val His Met Trp Asn Gly Asn Trp Thr Arg
        590                 595                 600 aac atc tat atc cct aca gcc tcc gca gat aat aga ggc agt atc ctg    1994
Asn Ile Tyr Ile Pro Thr Ala Ser Ala Asp Asn Arg Gly Ser Ile Leu
    605                 610                 615 acc atc aac cat gag gcc ggt tat aat agt tat ctg ttt ata aat ggt    2042
Thr Ile Asn His Glu Ala Gly Tyr Asn Ser Tyr Leu Phe Ile Asn Gly
620                 625                 630                 635 gac gaa aag gtc gtt tcc cag ggg tat aaa aag agc ttt gtt tcc gat    2090
Asp Glu Lys Val Val Ser Gln Gly Tyr Lys Lys Ser Phe Val Ser Asp
                640                 645                 650 ggt cag ttc tgg aaa gaa cgt gat gtg gtt gat act cgt gaa gcg cgt    2138
Gly Gln Phe Trp Lys Glu Arg Asp Val Val Asp Thr Arg Glu Ala Arg
            655                 660                 665 aag cca gag cag ttt ggt gtt cct gtg acg acc ctg gtg ggg tat tac    2186
Lys Pro Glu Gln Phe Gly Val Pro Val Thr Thr Leu Val Gly Tyr Tyr
        670                 675                 680 gat ccg gaa ggc acg ctg tca agc tac atc tat cct gcg atg tat ggt    2234
Asp Pro Glu Gly Thr Leu Ser Ser Tyr Ile Tyr Pro Ala Met Tyr Gly
    685                 690                 695 gcc tat ggc ttc act tat tcc gat gat agt cag aat cta tcc gat aac    2282
Ala Tyr Gly Phe Thr Tyr Ser Asp Asp Ser Gln Asn Leu Ser Asp Asn
700                 705                 710                 715 gac tgc cag ctg cag gtg gat acg aaa gaa ggg cag ttg cga ttc aga    2330
Asp Cys Gln Leu Gln Val Asp Thr Lys Glu Gly Gln Leu Arg Phe Arg
                720                 725                 730 ctg gct aat cac cgg gct aac aac act gta atg aat aag ttc cat att    2378
Leu Ala Asn His Arg Ala Asn Asn Thr Val Met Asn Lys Phe His Ile
            735                 740                 745 aac gtg cca aca gaa agt cag ccc aca cag gcc aca ttg gtt tgc aat    2426
Asn Val Pro Thr Glu Ser Gln Pro Thr Gln Ala Thr Leu Val Cys Asn
        750                 755                 760 aac aag ata ctg gat acc aaa tcg ctc aca cct gcg cca gaa gga ctt    2474
Asn Lys Ile Leu Asp Thr Lys Ser Leu Thr Pro Ala Pro Glu Gly Leu
    765                 770                 775 acc tat act gta aat ggg cag gca ctt cca gca aaa gaa aac gag gga    2522
Thr Tyr Thr Val Asn Gly Gln Ala Leu Pro Ala Lys Glu Asn Glu Gly
```

-continued

```
        780             785             790             795
tgc atc gtg tcc gtg aat tca ggt aaa cgt tac tgt ttg ccg gtt ggt     2570
Cys Ile Val Ser Val Asn Ser Gly Lys Arg Tyr Cys Leu Pro Val Gly
            800             805             810 caa cgg tca gga tat agc ctt cct gac tgg att gtt ggg cag gaa gtc     2618
Gln Arg Ser Gly Tyr Ser Leu Pro Asp Trp Ile Val Gly Gln Glu Val
        815             820             825 tat gtc gac agc ggg gct aaa gcg aaa gtg ctg ctt tct gac tgg gat     2666
Tyr Val Asp Ser Gly Ala Lys Ala Lys Val Leu Leu Ser Asp Trp Asp
    830             835             840 aac ctg tcc tat aac agg att ggt gag ttt gta ggt aat gtg aac cca     2714
Asn Leu Ser Tyr Asn Arg Ile Gly Glu Phe Val Gly Asn Val Asn Pro
845             850             855 gct gat atg aaa aaa gtt aaa gcc tgg aac gga cag tat ttg gac ttc     2762
Ala Asp Met Lys Lys Val Lys Ala Trp Asn Gly Gln Tyr Leu Asp Phe
860             865             870             875 agt aaa cct agg tca atg agg gtt gta tat aaa taa                     2798
Ser Lys Pro Arg Ser Met Arg Val Val Tyr Lys
            880             885
```

<210> SEQ ID NO 2
<211> LENGTH: 886
<212> TYPE: PRT
<213> ORGANISM: Unknown
<220> FEATURE:
<223> OTHER INFORMATION: Description of Unknown Organism: E. coli
      O157:H7 plasmid pO157

<400> SEQUENCE: 2

```
Met Lys Leu Lys Tyr Leu Ser Cys Thr Ile Leu Ala Pro Leu Ala Ile
1               5                   10                  15

Gly Val Phe Ser Ala Thr Ala Ala Asp Asn Asn Ser Ala Ile Tyr Phe
            20                  25                  30

Asn Thr Ser Gln Pro Ile Asn Asp Leu Gln Gly Ser Leu Ala Ala Glu
        35                  40                  45

Val Lys Phe Ala Gln Ser Gln Ile Leu Pro Ala His Pro Lys Glu Gly
    50                  55                  60

Asp Ser Gln Pro His Leu Thr Ser Leu Arg Lys Ser Leu Leu Leu Val
65                  70                  75                  80

Arg Pro Val Lys Ala Asp Asp Lys Thr Pro Val Gln Val Glu Ala Arg
                85                  90                  95

Asp Asp Asn Asn Lys Ile Leu Gly Thr Leu Thr Leu Tyr Pro Pro Ser
            100                 105                 110

Ser Leu Pro Asp Thr Ile Tyr His Leu Asp Gly Val Pro Glu Gly Gly
        115                 120                 125

Ile Asp Phe Thr Pro His Asn Gly Thr Lys Lys Ile Ile Asn Thr Val
    130                 135                 140

Ala Glu Val Asn Lys Leu Ser Asp Ala Ser Gly Ser Ser Ile His Ser
145                 150                 155                 160

His Leu Thr Asn Asn Ala Leu Val Glu Ile His Thr Ala Asn Gly Arg
                165                 170                 175

Trp Val Arg Asp Ile Tyr Leu Pro Gln Gly Pro Asp Leu Glu Gly Lys
            180                 185                 190

Met Val Arg Phe Val Ser Ser Ala Gly Tyr Ser Ser Thr Val Phe Tyr
        195                 200                 205

Gly Asp Arg Lys Val Thr Leu Ser Val Gly Asn Thr Leu Leu Phe Lys
    210                 215                 220
```

-continued

```
Tyr Val Asn Gly Gln Trp Phe Arg Ser Gly Glu Leu Glu Asn Asn Arg
225                 230                 235                 240

Ile Thr Tyr Ala Gln His Ile Trp Ser Ala Glu Leu Pro Ala His Trp
            245                 250                 255

Ile Val Pro Gly Leu Asn Leu Val Ile Lys Gln Gly Asn Leu Ser Gly
        260                 265                 270

Arg Leu Asn Asp Ile Lys Ile Gly Ala Pro Gly Glu Leu Leu Leu His
    275                 280                 285

Thr Ile Asp Ile Gly Met Leu Thr Thr Pro Arg Asp Arg Phe Asp Phe
290                 295                 300

Ala Lys Asp Lys Glu Ala His Arg Glu Tyr Phe Gln Thr Ile Pro Val
305                 310                 315                 320

Ser Arg Met Ile Val Asn Asn Tyr Ala Pro Leu His Leu Lys Glu Val
                325                 330                 335

Met Leu Pro Thr Gly Glu Leu Leu Thr Asp Met Asp Pro Gly Asn Gly
            340                 345                 350

Gly Trp His Ser Gly Thr Met Arg Gln Arg Ile Gly Lys Glu Leu Val
        355                 360                 365

Ser His Gly Ile Asp Asn Ala Asn Tyr Gly Leu Asn Ser Thr Ala Gly
    370                 375                 380

Leu Gly Glu Asn Ser His Pro Tyr Val Ala Gln Leu Ala Ala His
385                 390                 395                 400

Asn Ser Arg Gly Asn Tyr Ala Asn Gly Ile Gln Val His Gly Gly Ser
                405                 410                 415

Gly Gly Gly Gly Ile Val Thr Leu Asp Ser Thr Leu Gly Asn Glu Phe
            420                 425                 430

Ser His Glu Val Gly His Asn Tyr Gly Leu Gly His Tyr Val Asp Gly
    435                 440                 445

Phe Lys Gly Ser Val His Arg Ser Ala Glu Asn Asn Asn Ser Thr Trp
450                 455                 460

Gly Trp Asp Gly Asp Lys Lys Arg Phe Ile Pro Asn Phe Tyr Pro Ser
465                 470                 475                 480

Gln Thr Asn Glu Lys Ser Cys Leu Asn Asn Gln Cys Gln Glu Pro Phe
                485                 490                 495

Asp Gly His Lys Phe Gly Phe Asp Ala Met Ala Gly Gly Ser Pro Phe
            500                 505                 510

Ser Ala Ala Asn Arg Phe Thr Met Tyr Thr Pro Asn Ser Ser Ala Ile
    515                 520                 525

Ile Gln Arg Phe Phe Glu Asn Lys Ala Val Phe Asp Ser Arg Ser Ser
530                 535                 540

Thr Gly Phe Ser Lys Trp Asn Ala Asp Thr Gln Glu Met Glu Pro Tyr
545                 550                 555                 560

Glu His Thr Ile Asp Arg Ala Glu Gln Ile Thr Ala Ser Val Asn Glu
                565                 570                 575

Leu Ser Glu Ser Lys Met Ala Glu Leu Met Ala Glu Tyr Ala Val Val
            580                 585                 590

Lys Val His Met Trp Asn Gly Asn Trp Thr Arg Asn Ile Tyr Ile Pro
    595                 600                 605

Thr Ala Ser Ala Asp Asn Arg Gly Ser Ile Leu Thr Ile Asn His Glu
610                 615                 620

Ala Gly Tyr Asn Ser Tyr Leu Phe Ile Asn Gly Asp Glu Lys Val Val
625                 630                 635                 640

Ser Gln Gly Tyr Lys Lys Ser Phe Val Ser Asp Gly Gln Phe Trp Lys
```

-continued

```
                645                 650                 655
Glu Arg Asp Val Val Asp Thr Arg Glu Ala Arg Lys Pro Glu Gln Phe
                660                 665                 670
Gly Val Pro Val Thr Thr Leu Val Gly Tyr Tyr Asp Pro Glu Gly Thr
            675                 680                 685
Leu Ser Ser Tyr Ile Tyr Pro Ala Met Tyr Gly Ala Tyr Gly Phe Thr
        690                 695                 700
Tyr Ser Asp Asp Ser Gln Asn Leu Ser Asp Asn Asp Cys Gln Leu Gln
705                 710                 715                 720
Val Asp Thr Lys Glu Gly Gln Leu Arg Phe Arg Leu Ala Asn His Arg
                725                 730                 735
Ala Asn Asn Thr Val Met Asn Lys Phe His Ile Asn Val Pro Thr Glu
            740                 745                 750
Ser Gln Pro Thr Gln Ala Thr Leu Val Cys Asn Asn Lys Ile Leu Asp
        755                 760                 765
Thr Lys Ser Leu Thr Pro Ala Pro Glu Gly Leu Thr Tyr Thr Val Asn
    770                 775                 780
Gly Gln Ala Leu Pro Ala Lys Glu Asn Glu Gly Cys Ile Val Ser Val
785                 790                 795                 800
Asn Ser Gly Lys Arg Tyr Cys Leu Pro Val Gly Gln Arg Ser Gly Tyr
                805                 810                 815
Ser Leu Pro Asp Trp Ile Val Gly Gln Glu Val Tyr Val Asp Ser Gly
            820                 825                 830
Ala Lys Ala Lys Val Leu Leu Ser Asp Trp Asp Asn Leu Ser Tyr Asn
        835                 840                 845
Arg Ile Gly Glu Phe Val Gly Asn Val Asn Pro Ala Asp Met Lys Lys
    850                 855                 860
Val Lys Ala Trp Asn Gly Gln Tyr Leu Asp Phe Ser Lys Pro Arg Ser
865                 870                 875                 880
Met Arg Val Val Tyr Lys
                885

<210> SEQ ID NO 3
<211> LENGTH: 11
<212> TYPE: PRT
<213> ORGANISM: Unknown Organism
<220> FEATURE:
<221> NAME/KEY: misc_feature
<223> OTHER INFORMATION: Description of Unknown Organism: E. coli
      O157:H7 plasmid pO157

<400> SEQUENCE: 3

His Glu Val Gly His Asn Tyr Gly Leu Gly His
1               5                   10

<210> SEQ ID NO 4
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 4
ccctcgagtt tacgaaacag gtgtaaat                                      28

<210> SEQ ID NO 5
<211> LENGTH: 30
<212> TYPE: DNA
<213> ORGANISM: Artificial Sequence
```

```
<220> FEATURE:
<223> OTHER INFORMATION: Synthetic Oligonucleotide

<400> SEQUENCE: 5
cctctagatt atttatatac aaccctcatt                              30

<210> SEQ ID NO 6
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 6
ccgagctccg atgaaattaa agtatctgtc                              30

<210> SEQ ID NO 7
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 7
cctcgagttt atatacaacc ctcattg                                 27

<210> SEQ ID NO 8
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 8
ccgctccggt gaactggaga ata                                     23

<210> SEQ ID NO 9
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 9
gaccataatt atgaccaaca tcatgactga                              30

<210> SEQ ID NO 10
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 10
ccttatctgc ggaggctgta ggg                                     23

<210> SEQ ID NO 11
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 11
tgagttcagt catgatgttg gtcataatta t                            31
```

-continued

<210> SEQ ID NO 12
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 12
gagaataatc gaatcactta tgctc                                          25

<210> SEQ ID NO 13
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 13
cggtggagga acggctatcg a                                              21

<210> SEQ ID NO 14
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 14
tttacgaaac aggtgtaaat atgttataaa                                     30

<210> SEQ ID NO 15
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 15
cagttcaccg gagcggaacc a                                              21

<210> SEQ ID NO 16
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 16
gcttcagcaa gtggaatgca gatac                                          25

<210> SEQ ID NO 17
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 17
ttatttatat acaaccctca ttgacctagg                                     30

<210> SEQ ID NO 18
<211> LENGTH: 2795
<212> TYPE: DNA
<213> ORGANISM: Unknown
<220> FEATURE:
<223> OTHER INFORMATION: Description of Unknown Organism: E. coli O157:H7 plasmid pO157
<220> FEATURE:
<221> NAME/KEY: CDS
<222> LOCATION: (138)..(2795)
<223> OTHER INFORMATION:

<400> SEQUENCE: 18

```
tttacgaaac aggtgtaaat atgttataaa aataaccaac gactagtgaa taagtcgctc      60
ctgaaaaaat aaaatataga aatactgtta tatccggctg catgaacact aaaatgaatg     120
agagatggag aacaccg atg aaa tta aag tat ctg tca tgt acg atc ctt       170
                   Met Lys Leu Lys Tyr Leu Ser Cys Thr Ile Leu
                    1               5                  10 gcc cct ctg gcg att ggg gta ttt tct gca aca gct gct gat aat aat      218
Ala Pro Leu Ala Ile Gly Val Phe Ser Ala Thr Ala Ala Asp Asn Asn
             15                  20                  25 tca gcc att tat ttc aat acc tcc cag cct ata aat gat ctg cag ggt      266
Ser Ala Ile Tyr Phe Asn Thr Ser Gln Pro Ile Asn Asp Leu Gln Gly
         30                  35                  40 tcg ttg gcc gca gag gtg aaa ttt gca caa agc cag att tta ccc gcc      314
Ser Leu Ala Ala Glu Val Lys Phe Ala Gln Ser Gln Ile Leu Pro Ala
     45                  50                  55 cat cct aaa gaa ggg gat agt caa cca cat ctg acc agc ctg cgg aaa      362
His Pro Lys Glu Gly Asp Ser Gln Pro His Leu Thr Ser Leu Arg Lys
 60                  65                  70                  75 agt ctg ctg ctt gtc cgt ccg gtg aaa gct gat gat aaa aca cct gtt      410
Ser Leu Leu Leu Val Arg Pro Val Lys Ala Asp Asp Lys Thr Pro Val
                 80                  85                  90 cag gtg gaa gcc cgc gat gat aat aat aaa att ctc ggt acg tta acc      458
Gln Val Glu Ala Arg Asp Asp Asn Asn Lys Ile Leu Gly Thr Leu Thr
             95                 100                 105 ctt tat cct cct tca tca cta ccg gat aca atc tac cat ctg gat ggt      506
Leu Tyr Pro Pro Ser Ser Leu Pro Asp Thr Ile Tyr His Leu Asp Gly
        110                 115                 120 gtt ccg gaa ggt ggt atc gat ttc aca cct cat aat gga acg aaa aag      554
Val Pro Glu Gly Gly Ile Asp Phe Thr Pro His Asn Gly Thr Lys Lys
    125                 130                 135 atc att aat acg gtg gct gaa gta aac aaa ctc agt gat gcc agc ggg      602
Ile Ile Asn Thr Val Ala Glu Val Asn Lys Leu Ser Asp Ala Ser Gly
140                 145                 150                 155 agt tct att cat agc cat cta aca aat aat gca ctg gtg gag atc cat      650
Ser Ser Ile His Ser His Leu Thr Asn Asn Ala Leu Val Glu Ile His
                160                 165                 170 act gca aat ggt cgt tgg gta aga gac att tat ctg ccg cag gga ccc      698
Thr Ala Asn Gly Arg Trp Val Arg Asp Ile Tyr Leu Pro Gln Gly Pro
            175                 180                 185 gac ctt gaa ggt aag atg gtt cgc ttt gtt tcg tct gca ggc tat agt      746
Asp Leu Glu Gly Lys Met Val Arg Phe Val Ser Ser Ala Gly Tyr Ser
        190                 195                 200 tca acg gtt ttt tat ggt gat cga aaa gtc aca ctc tcg gtg ggt aac      794
Ser Thr Val Phe Tyr Gly Asp Arg Lys Val Thr Leu Ser Val Gly Asn
    205                 210                 215 act ctt ctg ttc aaa tat gta aat ggt cag tgg ttc cgc tcc ggt gaa      842
Thr Leu Leu Phe Lys Tyr Val Asn Gly Gln Trp Phe Arg Ser Gly Glu
220                 225                 230                 235 ctg gag aat aat cga atc act tat gct cag cat att tgg agt gct gaa      890
Leu Glu Asn Asn Arg Ile Thr Tyr Ala Gln His Ile Trp Ser Ala Glu
                240                 245                 250 ctg cct gcg cac tgg atc gtg cct ggt tta aac ttg gtg att aaa cag      938
Leu Pro Ala His Trp Ile Val Pro Gly Leu Asn Leu Val Ile Lys Gln
            255                 260                 265
```

-continued

| | |
|---|---|
| ggc aat ctg agc ggt cgc cta aat gat atc aag att gga gca ccg ggt<br>Gly Asn Leu Ser Gly Arg Leu Asn Asp Ile Lys Ile Gly Ala Pro Gly<br>270                         275                    280 | 986 |
| gag ctg ttg ttg cat aca att gat atc ggg atg ttg acc act ccc cgg<br>Glu Leu Leu Leu His Thr Ile Asp Ile Gly Met Leu Thr Thr Pro Arg<br>285                     290                   295 | 1034 |
| gat cgc ttt gat ttt gcc aaa gac aaa gaa gca cat agg gaa tat ttc<br>Asp Arg Phe Asp Phe Ala Lys Asp Lys Glu Ala His Arg Glu Tyr Phe<br>300                     305                 310             315 | 1082 |
| cag acc att cct gta agt cgt atg att gtt aat aat tat gcg cct cta<br>Gln Thr Ile Pro Val Ser Arg Met Ile Val Asn Asn Tyr Ala Pro Leu<br>                  320                 325             330 | 1130 |
| cac cta aag gaa gtt atg tta cca acc gga gag tta ttg aca gat atg<br>His Leu Lys Glu Val Met Leu Pro Thr Gly Glu Leu Leu Thr Asp Met<br>              335                 340                345 | 1178 |
| gat cca gga aat ggt ggg tgg cat agt ggt aca atg cgt caa aga ata<br>Asp Pro Gly Asn Gly Gly Trp His Ser Gly Thr Met Arg Gln Arg Ile<br>350                     355                    360 | 1226 |
| ggt aaa gaa ttg gtt tcg cat ggc att gat aat gct aac tat ggt tta<br>Gly Lys Glu Leu Val Ser His Gly Ile Asp Asn Ala Asn Tyr Gly Leu<br>365                     370                 375 | 1274 |
| aat agt acc gca ggc tta ggg gag aat agt cat cca tat gta gtt gcg<br>Asn Ser Thr Ala Gly Leu Gly Glu Asn Ser His Pro Tyr Val Val Ala<br>380                     385                 390             395 | 1322 |
| caa tta gcg gca cat aat agc cgc ggt aat tat gct aat ggc atc cag<br>Gln Leu Ala Ala His Asn Ser Arg Gly Asn Tyr Ala Asn Gly Ile Gln<br>                  400                 405             410 | 1370 |
| gtt cat ggt ggc tcc gga ggt ggg gga att gtt act tta gat tcc aca<br>Val His Gly Gly Ser Gly Gly Gly Gly Ile Val Thr Leu Asp Ser Thr<br>Val His Gly Gly Ser Gly Gly Gly Gly Ile Val Thr Leu Asp Ser Thr<br>              415                 420                 425 | 1418 |
| ttg ggg aat gag ttc agt cat gat gtt ggt cat aat tat ggt ctt ggt<br>Leu Gly Asn Glu Phe Ser His Asp Val Gly His Asn Tyr Gly Leu Gly<br>430                     435                 440 | 1466 |
| cat tat gta gat ggt ttc aag ggt tct gta cat cgt agt gca gaa aat<br>His Tyr Val Asp Gly Phe Lys Gly Ser Val His Arg Ser Ala Glu Asn<br>445                     450                 455 | 1514 |
| aac aac tca act tgg gga tgg gat ggt gat aaa aaa cgg ttt att cct<br>Asn Asn Ser Thr Trp Gly Trp Asp Gly Asp Lys Lys Arg Phe Ile Pro<br>460                     465                 470             475 | 1562 |
| aac ttt tat ccg tct caa aca aat gaa aag agt tgt ctg aat aat cag<br>Asn Phe Tyr Pro Ser Gln Thr Asn Glu Lys Ser Cys Leu Asn Asn Gln<br>                  480                 485             490 | 1610 |
| tgt caa gaa ccg ttt gat gga cac aaa ttt ggt ttt gac gcc atg gcg<br>Cys Gln Glu Pro Phe Asp Gly His Lys Phe Gly Phe Asp Ala Met Ala<br>                    495                 500             505 | 1658 |
| gga ggc agc cct ttc tct gct gca aac cgt ttc aca atg tat act ccg<br>Gly Gly Ser Pro Phe Ser Ala Ala Asn Arg Phe Thr Met Tyr Thr Pro<br>510                     515                 520 | 1706 |
| aat tca tcg gct atc atc cag cgt ttt ttt gaa aat aaa gct gtg ttc<br>Asn Ser Ser Ala Ile Ile Gln Arg Phe Phe Glu Asn Lys Ala Val Phe<br>525                     530                 535 | 1754 |
| gat agc cgt tcc tcc acc ggc ttc agc aag tgg aat gca gat acg cag<br>Asp Ser Arg Ser Ser Thr Gly Phe Ser Lys Trp Asn Ala Asp Thr Gln<br>540                     545                 550             555 | 1802 |
| gaa atg gaa ccg tat gaa cac acc att gac cgt gcg gag cag att acg<br>Glu Met Glu Pro Tyr Glu His Thr Ile Asp Arg Ala Glu Gln Ile Thr<br>                  560                 565             570 | 1850 |
| gct tca gtc aat gag cta agt gaa agc aaa atg gct gag ctg atg gca<br>Ala Ser Val Asn Glu Leu Ser Glu Ser Lys Met Ala Glu Leu Met Ala | 1898 |

```
                    575                 580                 585
gag tac gct gtc gtc aaa gtg cat atg tgg aac ggt aac tgg aca aga       1946
Glu Tyr Ala Val Val Lys Val His Met Trp Asn Gly Asn Trp Thr Arg
        590                 595                 600 aac atc tat atc cct aca gcc tcc gca gat aat aga ggc agt atc ctg       1994
Asn Ile Tyr Ile Pro Thr Ala Ser Ala Asp Asn Arg Gly Ser Ile Leu
    605                 610                 615 acc atc aac cat gag gcc ggt tat aat agt tat ctg ttt ata aat ggt       2042
Thr Ile Asn His Glu Ala Gly Tyr Asn Ser Tyr Leu Phe Ile Asn Gly
620                 625                 630                 635 gac gaa aag gtc gtt tcc cag ggg tat aaa aag agc ttt gtt tcc gat       2090
Asp Glu Lys Val Val Ser Gln Gly Tyr Lys Lys Ser Phe Val Ser Asp
                640                 645                 650 ggt cag ttc tgg aaa gaa cgt gat gtg gtt gat act cgt gaa gcg cgt       2138
Gly Gln Phe Trp Lys Glu Arg Asp Val Val Asp Thr Arg Glu Ala Arg
            655                 660                 665 aag cca gag cag ttt ggt gtt cct gtg acg acc ctg gtg ggg tat tac       2186
Lys Pro Glu Gln Phe Gly Val Pro Val Thr Thr Leu Val Gly Tyr Tyr
        670                 675                 680 gat ccg gaa ggc acg ctg tca agc tac atc tat cct gcg atg tat ggt       2234
Asp Pro Glu Gly Thr Leu Ser Ser Tyr Ile Tyr Pro Ala Met Tyr Gly
    685                 690                 695 gcc tat ggc ttc act tat tcc gat gat agt cag aat cta tcc gat aac       2282
Ala Tyr Gly Phe Thr Tyr Ser Asp Asp Ser Gln Asn Leu Ser Asp Asn
700                 705                 710                 715 gac tgc cag ctg cag gtg gat acg aaa gaa ggg cag ttg cga ttc aga       2330
Asp Cys Gln Leu Gln Val Asp Thr Lys Glu Gly Gln Leu Arg Phe Arg
                720                 725                 730 ctg gct aat cac cgg gct aac aac act gta atg aat aag ttc cat att       2378
Leu Ala Asn His Arg Ala Asn Asn Thr Val Met Asn Lys Phe His Ile
            735                 740                 745 aac gtg cca aca gaa agt cag ccc aca cag gcc aca ttg gtt tgc aat       2426
Asn Val Pro Thr Glu Ser Gln Pro Thr Gln Ala Thr Leu Val Cys Asn
        750                 755                 760 aac aag ata ctg gat acc aaa tcg ctc aca cct gcg cca gaa gga ctt       2474
Asn Lys Ile Leu Asp Thr Lys Ser Leu Thr Pro Ala Pro Glu Gly Leu
    765                 770                 775 acc tat act gta aat ggg cag gca ctt cca gca aaa gaa aac gag gga       2522
Thr Tyr Thr Val Asn Gly Gln Ala Leu Pro Ala Lys Glu Asn Glu Gly
780                 785                 790                 795 tgc atc gtg tcc gtg aat tca ggt aaa cgt tac tgt ttg ccg gtt ggt       2570
Cys Ile Val Ser Val Asn Ser Gly Lys Arg Tyr Cys Leu Pro Val Gly
                800                 805                 810 caa cgg tca gga tat agc ctt cct gac tgg att gtt ggg cag gaa gtc       2618
Gln Arg Ser Gly Tyr Ser Leu Pro Asp Trp Ile Val Gly Gln Glu Val
            815                 820                 825 tat gtc gac agc ggg gct aaa gcg aaa gtg ctg ctt tct gac tgg gat       2666
Tyr Val Asp Ser Gly Ala Lys Ala Lys Val Leu Leu Ser Asp Trp Asp
        830                 835                 840 aac ctg tcc tat aac agg att ggt gag ttt gta ggt aat gtg aac cca       2714
Asn Leu Ser Tyr Asn Arg Ile Gly Glu Phe Val Gly Asn Val Asn Pro
    845                 850                 855 gct gat atg aaa aaa gtt aaa gcc tgg aac gga cag tat ttg gac ttc       2762
Ala Asp Met Lys Lys Val Lys Ala Trp Asn Gly Gln Tyr Leu Asp Phe
860                 865                 870                 875 agt aaa cct agg tca atg agg gtt gta tat aaa                           2795
Ser Lys Pro Arg Ser Met Arg Val Val Tyr Lys
                880                 885
```

-continued

<210> SEQ ID NO 19
<211> LENGTH: 886
<212> TYPE: PRT
<213> ORGANISM: Unknown
<220> FEATURE:
<223> OTHER INFORMATION: Description of Unknown Organism: E. coli
      O157:H7 plasmid pO157

<400> SEQUENCE: 19

Met Lys Leu Lys Tyr Leu Ser Cys Thr Ile Leu Ala Pro Leu Ala Ile
1               5                   10                  15

Gly Val Phe Ser Ala Thr Ala Ala Asp Asn Asn Ser Ala Ile Tyr Phe
            20                  25                  30

Asn Thr Ser Gln Pro Ile Asn Asp Leu Gln Gly Ser Leu Ala Ala Glu
        35                  40                  45

Val Lys Phe Ala Gln Ser Gln Ile Leu Pro Ala His Pro Lys Glu Gly
    50                  55                  60

Asp Ser Gln Pro His Leu Thr Ser Leu Arg Lys Ser Leu Leu Leu Val
65                  70                  75                  80

Arg Pro Val Lys Ala Asp Asp Lys Thr Pro Val Gln Val Glu Ala Arg
                85                  90                  95

Asp Asp Asn Asn Lys Ile Leu Gly Thr Leu Thr Leu Tyr Pro Pro Ser
            100                 105                 110

Ser Leu Pro Asp Thr Ile Tyr His Leu Asp Gly Val Pro Glu Gly Gly
        115                 120                 125

Ile Asp Phe Thr Pro His Asn Gly Thr Lys Lys Ile Ile Asn Thr Val
    130                 135                 140

Ala Glu Val Asn Lys Leu Ser Asp Ala Ser Gly Ser Ser Ile His Ser
145                 150                 155                 160

His Leu Thr Asn Asn Ala Leu Val Glu Ile His Thr Ala Asn Gly Arg
                165                 170                 175

Trp Val Arg Asp Ile Tyr Leu Pro Gln Gly Pro Asp Leu Glu Gly Lys
            180                 185                 190

Met Val Arg Phe Val Ser Ser Ala Gly Tyr Ser Ser Thr Val Phe Tyr
        195                 200                 205

Gly Asp Arg Lys Val Thr Leu Ser Val Gly Asn Thr Leu Leu Phe Lys
    210                 215                 220

Tyr Val Asn Gly Gln Trp Phe Arg Ser Gly Glu Leu Glu Asn Asn Arg
225                 230                 235                 240

Ile Thr Tyr Ala Gln His Ile Trp Ser Ala Glu Leu Pro Ala His Trp
                245                 250                 255

Ile Val Pro Gly Leu Asn Leu Val Ile Lys Gln Gly Asn Leu Ser Gly
            260                 265                 270

Arg Leu Asn Asp Ile Lys Ile Gly Ala Pro Gly Glu Leu Leu Leu His
        275                 280                 285

Thr Ile Asp Ile Gly Met Leu Thr Thr Pro Arg Asp Arg Phe Asp Phe
    290                 295                 300

Ala Lys Asp Lys Glu Ala His Arg Glu Tyr Phe Gln Thr Ile Pro Val
305                 310                 315                 320

Ser Arg Met Ile Val Asn Asn Tyr Ala Pro Leu His Leu Lys Glu Val
                325                 330                 335

Met Leu Pro Thr Gly Glu Leu Leu Thr Asp Met Asp Pro Gly Asn Gly
            340                 345                 350

Gly Trp His Ser Gly Thr Met Arg Gln Arg Ile Gly Lys Glu Leu Val
        355                 360                 365

-continued

```
Ser His Gly Ile Asp Asn Ala Asn Tyr Gly Leu Asn Ser Thr Ala Gly
370                 375                 380

Leu Gly Glu Asn Ser His Pro Tyr Val Val Ala Gln Leu Ala Ala His
385                 390                 395                 400

Asn Ser Arg Gly Asn Tyr Ala Asn Gly Ile Gln Val His Gly Gly Ser
                405                 410                 415

Gly Gly Gly Gly Ile Val Thr Leu Asp Ser Thr Leu Gly Asn Glu Phe
                420                 425                 430

Ser His Asp Val Gly His Asn Tyr Gly Leu Gly His Tyr Val Asp Gly
                435                 440                 445

Phe Lys Gly Ser Val His Arg Ser Ala Glu Asn Asn Ser Thr Trp
450                 455                 460

Gly Trp Asp Gly Asp Lys Lys Arg Phe Ile Pro Asn Phe Tyr Pro Ser
465                 470                 475                 480

Gln Thr Asn Glu Lys Ser Cys Leu Asn Asn Gln Cys Gln Glu Pro Phe
                485                 490                 495

Asp Gly His Lys Phe Gly Phe Asp Ala Met Ala Gly Gly Ser Pro Phe
                500                 505                 510

Ser Ala Ala Asn Arg Phe Thr Met Tyr Thr Pro Asn Ser Ser Ala Ile
                515                 520                 525

Ile Gln Arg Phe Phe Glu Asn Lys Ala Val Phe Asp Ser Arg Ser Ser
530                 535                 540

Thr Gly Phe Ser Lys Trp Asn Ala Asp Thr Gln Glu Met Glu Pro Tyr
545                 550                 555                 560

Glu His Thr Ile Asp Arg Ala Glu Gln Ile Thr Ala Ser Val Asn Glu
                565                 570                 575

Leu Ser Glu Ser Lys Met Ala Glu Leu Met Ala Glu Tyr Ala Val Val
                580                 585                 590

Lys Val His Met Trp Asn Gly Asn Trp Thr Arg Asn Ile Tyr Ile Pro
                595                 600                 605

Thr Ala Ser Ala Asp Asn Arg Gly Ser Ile Leu Thr Ile Asn His Glu
610                 615                 620

Ala Gly Tyr Asn Ser Tyr Leu Phe Ile Asn Gly Asp Glu Lys Val Val
625                 630                 635                 640

Ser Gln Gly Tyr Lys Lys Ser Phe Val Ser Asp Gly Gln Phe Trp Lys
                645                 650                 655

Glu Arg Asp Val Val Asp Thr Arg Glu Ala Arg Lys Pro Glu Gln Phe
                660                 665                 670

Gly Val Pro Val Thr Thr Leu Val Gly Tyr Tyr Asp Pro Glu Gly Thr
                675                 680                 685

Leu Ser Ser Tyr Ile Tyr Pro Ala Met Tyr Gly Ala Tyr Gly Phe Thr
690                 695                 700

Tyr Ser Asp Asp Ser Gln Asn Leu Ser Asp Asn Asp Cys Gln Leu Gln
705                 710                 715                 720

Val Asp Thr Lys Glu Gly Gln Leu Arg Phe Arg Leu Ala Asn His Arg
                725                 730                 735

Ala Asn Asn Thr Val Met Asn Lys Phe His Ile Asn Val Pro Thr Glu
                740                 745                 750

Ser Gln Pro Thr Gln Ala Thr Leu Val Cys Asn Asn Lys Ile Leu Asp
                755                 760                 765

Thr Lys Ser Leu Thr Pro Ala Pro Glu Gly Leu Thr Tyr Thr Val Asn
770                 775                 780

Gly Gln Ala Leu Pro Ala Lys Glu Asn Glu Gly Cys Ile Val Ser Val
```

```
                785                 790                 795                 800
Asn Ser Gly Lys Arg Tyr Cys Leu Pro Val Gly Gln Arg Ser Gly Tyr
                805                 810                 815

Ser Leu Pro Asp Trp Ile Val Gly Gln Glu Val Tyr Val Asp Ser Gly
                820                 825                 830

Ala Lys Ala Lys Val Leu Leu Ser Asp Trp Asp Asn Leu Ser Tyr Asn
                835                 840                 845

Arg Ile Gly Glu Phe Val Gly Asn Val Asn Pro Ala Asp Met Lys Lys
    850                 855                 860

Val Lys Ala Trp Asn Gly Gln Tyr Leu Asp Phe Ser Lys Pro Arg Ser
865                 870                 875                 880

Met Arg Val Val Tyr Lys
                885

<210> SEQ ID NO 20
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 20
ccgagctccg gctgataata attcagccat ttatttc                              37

<210> SEQ ID NO 21
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 21
cctcgagttt atatacaacc ctgattg                                         27

<210> SEQ ID NO 22
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 22
atgaaattaa agtatctgtc atgtacgatc cttgcccctt gtgtaggctg gagctgcttc     60

<210> SEQ ID NO 23
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 23
taatttatat acaaccctca ttgacctagg tttactgaag catatgaata tcctccttag     60

<210> SEQ ID NO 24
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 24
aagggcccct ctgaggtgtc tgttaaaccc gtgg                                 34
```

```
<210> SEQ ID NO 25
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 25
aaaaatggcc acgaagtggc cgcaccgtct cagg                              34
```

US 7,264,922 B2

METHOD OF REDUCING COMPLEMENT - MEDIATED DISRUPTION OF CELLS

CROSS-REFERENCE TO RELATED APPLICATIONS

This application is a continuation-in-part of U.S. application Ser. No. 10/786,445, filed Feb. 25, 2004, which is a continuation-in-part of U.S. application Ser. No. 10/002,309, filed Oct. 26, 2001, now U.S. Pat. No. 6,872,559, which claims priority to U.S. Provisional Application No. 60/243,675, filed Oct. 26, 2000. This application also claims priority to U.S. Provisional Application No. 60/633,583, filed Dec. 6, 2004 and U.S. Provisional Application No. 60/651,560, filed Feb. 10, 2005.

STATEMENT REGARDING FEDERALLY SPONSORED RESEARCH OR DEVELOPMENT

This invention was made with United States government support awarded by NIH AI051735.

INTRODUCTION

Enterohemorrhagic *Escherichia coli* (EHEC) serotype O157:H7 strain is a human enteric bacterial pathogen that causes diarrheal disease, hemorrhagic colitis, and hemolytic uremic syndrome (HUS). Each year in the United States, an estimated 20,000 people suffer from diarrheal disease associated with *E. coli* O157:H7 infection, which is typically contracted by ingesting contaminated foods, especially undercooked meat. Approximately 6% of infected individuals develop HUS, which can lead to renal failure and death. Young children and the elderly are particularly susceptible to developing HUS.

In general, bacterial infections are commonly treated by administering appropriate antibiotics. However, *E. coli* O157:H7 infection typically has a very rapid progression, and is consequently very difficult to treat. Often by the time the disease is diagnosed, the infected individual is severely ill and toxic proteins secreted by the bacteria may have damaged mucosal cells and entered the blood stream. Antibiotic treatment of patients infected with *E. coli* O157:H7 is generally not successful and, in fact, is believed to be contraindicated.

*E. coli* O157:H7 bacteria are very proficient at establishing an infection; ingestion of as few as 10 live bacteria is sufficient to establish an infection. The highly infective nature of *E. coli* O157:H7 and the devastating sequelae associated with infection by this bacteria, together with the extensive public attention given to outbreaks of hemorrhagic colitis, has generated a great deal of interest among medical professionals and the general public in developing the means for early diagnosis and treatment of the disease. The entire genome of the *E. Coli* O157:H7 EDL933W (ATCC 43895) was sequenced with the expectation that valuable information concerning the organism's pathogenicity would be uncovered, which may facilitate development of methods of preventing infections, or preventing or treating hemolytic uremic syndrome in individuals infected with of the organism. The DNA sequence of *E. coli* O157:H7 was compared with that of *E. coli* K12, a non-pathogenic strain commonly used in research. The genome of *E. coli* O157:H7 exceeds that of *E. coli* K-12 by more than a million base pairs and has up to 1000 genes not found on K-12. These additional gene sequences are distributed throughout more than 250 sites in islands, with each island containing from zero to sixty genes (1).

There is a need for improved methods of early detection of *E. coli* O157:H7 infections and for methods of preventing or treating individuals infected with *E. coli* O157:H7.

BRIEF SUMMARY OF THE INVENTION

In one aspect, the present invention provides a purified antibody that binds specifically to a polypeptide comprising SEQ ID NO:2.

In another aspect, the present invention includes a method of reducing colonization of epithelial cells by StcE producing bacteria comprising contacting the epithelial cells with an antibody that binds specifically to SEQ ID NO:2 or an inhibitor of StcE.

In yet another aspect, the invention provides a composition comprising a purified polypeptide comprising at least 25 consecutive amino acid residues of SEQ ID NO:2 and an adjuvant.

Also provided is a method of eliciting an immune response in an animal comprising inoculating the animal with a composition comprising a purified polypeptide comprising at least 25 consecutive amino acid residues of SEQ ID NO:2 and an adjuvant.

The present invention also provides a method of reducing complement-mediated disruption of cells comprising contacting the cells with a purified polypeptide comprising amino acid residues 24-886 of SEQ ID NO:2 or SEQ ID NO:19 so as to reduce complement-mediated disruption relative to that of untreated cells.

The invention further provides a method of reducing the viscosity of a material comprising a mucin or a glycosylated polypeptide comprising contacting the material with a viscosity reducing effective amount of StcE.

In another aspect, the invention provides a composition for enhancing delivery of a target antigen to mucosal cells comprising the target antigen and StcE.

The composition for enhancing delivery of a target antigen to mucosal cells may be used in a method of eliciting in an animal an immune response to a target antigen comprising contacting the mucosal cells of the animal with the composition.

The present invention provides a method of detecting StcE in a sample by detecting binding of an antibody with selectively for a polypeptide comprising SEQ ID NO:2 of claim 1 to a polypeptide in the sample.

In another aspect, the invention includes detecting StcE activity by contacting the sample with C1-INH under suitable conditions to allow cleavage of C1-INH by StcE, if present and detecting C1-INH cleavage.

The invention also provides a method of evaluating a test substance for the ability to inhibit StcE comprising contacting C1-INH with the test substance and StcE and detecting C1-INH cleavage.

BRIEF DESCRIPTION OF THE SEVERAL VIEWS OF THE DRAWINGS

FIG. 15A shows detection of erythrocyte binding by untreated C1-INH, or C1-INH treated with buffer alone ("mock treated") or StcE'-His as detected by flow cytometry. FIG. 15 C shows mean fluorescence detection of erythrocyte binding by C1-INH treated with StcE' E435D-His with increasing concentrations of C1-INH. FIG. 15D shows a blot of immunoprecipitated C1-INH untreated or treated with StcE'-His or StcE' E435D-His, separated by SDS-PAGE, transferred to nitrocellulose, and probed with an anti-StcE' Ab.

FIG. 17B shows electrophoretically separated $^{35}$S-methionine-labeled full length hC1-INH or C-serp(98), a recombinant C1-INH molecule truncated at amino acid 98, each untreated or treated with StcE'-His and immunoprecipitated with polyclonal anti-human C1-INH IgG-Protein A sepharose.

DETAILED DESCRIPTION OF THE INVENTION

Figure 1:
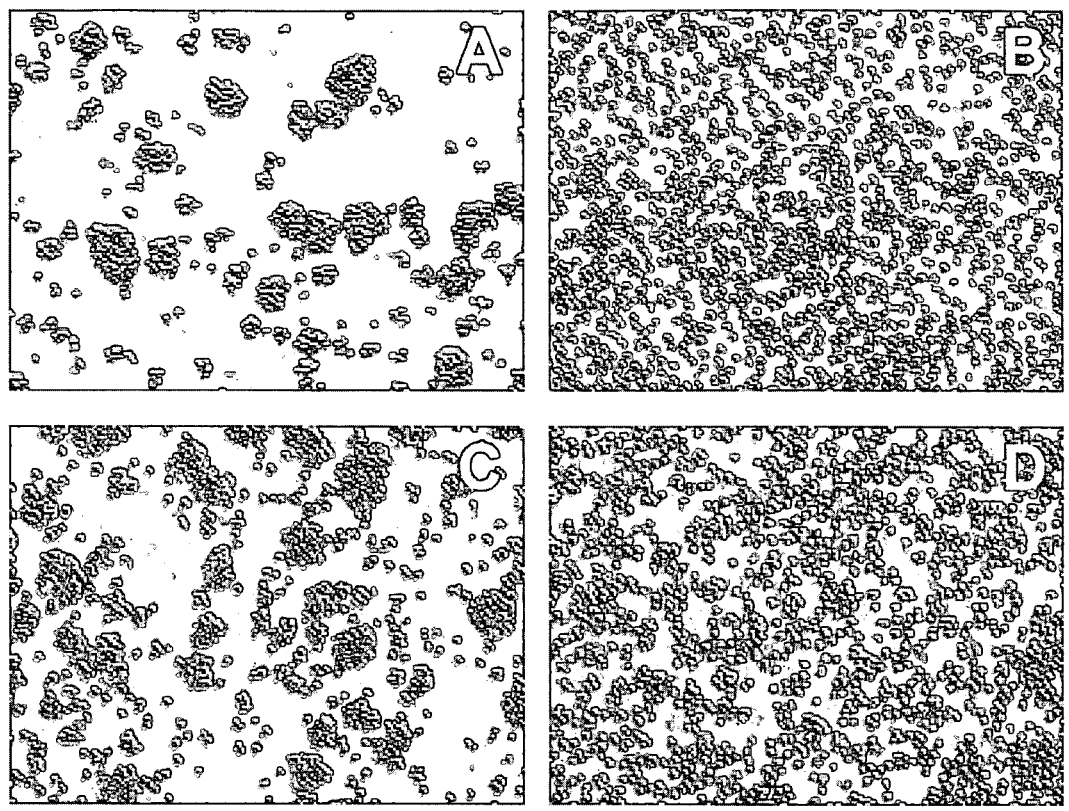
FIG. 1 shows the differential effect of *E. coli* strains containing (FIG. 1A and FIG. 1C) or lacking (FIG. 1B and FIG. 1D) the plasmid pO157 on aggregation of T cells.

Each of the publications or applications cited or listed herein is incorporated by reference in its entirety.

Strains of the serotype O157:H7 EDL933W contain a 92 kb plasmid designated pO157. As described in the Examples below, bacterial strains containing the plasmid cause the aggregation of two cultured human CD4$^+$ T cell lines, Jurkat and MOLT-4, but do not cause aggregation of a B cell lymphoma line (Raji), or of macrophage-like cell lines (U937 and HL-60). Aggregation of the CD4$^+$ T cells occurs in the presence of serum, but not in its absence. Strains lacking the plasmid do not cause aggregation of CD4$^+$ T cells.

We employed transposon mutagenesis to identify a gene on pO157 of previously unknown function whose product is associated with the observed aggregation effect. The coding sequence and the deduced amino acid sequence of the protein it encodes are shown in SEQ ID NO:1 and SEQ ID NO:2, respectively. The protein, designated "StcE", contains a putative cleavable N-terminal signal sequence. In cultures of bacteria expressing StcE, at least a portion of expressed StcE protein appears to be secreted into the culture medium, although StcE may also be associated with the cell surface.

A genetic construct expressing a His-tagged StcE protein was made by ligating the StcE coding sequence in frame to a sequence specifying a poly-His tail to permit expression and recovery of relatively large amounts of highly purified StcE protein, as described below.

In order to further evaluate the StcE protein for possible cytotoxic effects, variety of cell types were treated with StcE protein as described in the examples. Cells treated with StcE showed a high degree of aggregation in the presence of serum, but not in the absence of serum.

Because StcE-mediated aggregation occurred only in cells also treated with serum, the ability of StcE to bind to a specific serum protein was evaluated by Far Western blotting using the StcE protein as the probe. An acidic serum protein of about 105 kDa by SDS PAGE was identified as binding to StcE. The target protein was recovered, subjected to limited digestion by an endopeptidase, and the peptide products analyzed by mass spectrometry. The protein to which StcE binds was identified as C1-inhibitor (C1-INH), which serves as a critical inhibitor in the proteolytic cascade involved in complement activation.

The plasma protein C1-INH is a serpin (serine protease inhibitor) that controls the activation of C1, the first component of the complement cascade. The C1 component is made up of three subcomponents: C1q, C1r, and C1s. In the classical pathway of complement activation, C1 binds to an antigen-antibody complex or certain pathogens (e.g., HIV-1), which causes the proteolytic autoactivation of C1r, which in turn causes the proteolytic activation of C1s. C1-INH inhibits activation of the classical pathway by binding to C1 and inactivating C1r and C1s. In addition to its role in controlling activation of the classical complement pathway, C1-INH inhibits other serine proteases involved in the intrinsic coagulation pathway and kinin-forming system (reviewed in (3)).

Treatment of serum or purified C1-INH with purified StcE results in the apparent disappearance of C1-INH, presumably as a result of specific proteolytic cleavage of C1-INH by StcE. The predicted StcE amino acid sequence comprises the sequence HEVGHNYGLGH (SEQ ID NO:3) (residues 434-444 of SEQ ID NO:2), which corresponds to the histidine rich active site of metalloproteases (5). Further evidence that StcE may be a metalloprotease is provided by the observation that proteolysis of C1-INH by StcE is reduced in the presence of EDTA or BPS, which chelate divalent metal ions (e.g., $Zn^{2+}$) required for metalloprotease activity.

In U.S. application Ser. No. 10/002,309, filed Oct. 26, 2001, of which the present application is a continuation-in-part, we proposed that the putative protease StcE by enterohemorrhagic strains of *E. coli* EHEC may lead to proteolysis of C1-INH and reduction of C1-INH activity. Loss of C1-INH activity may result in unregulated pro-inflammatory or coagulation response that may be responsible for tissue damage in the intestine and kidney of persons infected with EHEC. It is also possible that the StcE serum-dependent cellular aggregation phenotype plays a role in the pathogenesis of HUS because one of the hallmarks of HUS is thrombocytopenia with an accumulation of a large number of platelets in renal microthrombi. The kidneys of those diagnosed with HUS also contain large amounts of deposited fibrin.

Deficiencies in C1-INH can lead to a variety of diseases. For example, a hereditary deficiency in C1-INH (hereditary angiodema) is characterized by transient, recurrent attacks of intestinal cramps, vomiting and diarrhea. Hereditary defects in production of a different inhibitor of the complement cascade, Factor H, are associated with a form of hemolytic uremic syndrome (HUS) similar to that described for EHEC-mediated HUS.

The proteolytic activity of StcE may be a common mode of pathogenesis among some diarrheagenic strains of *E. coli*. Colony blot analysis and amplification of *E. coli* DNA using oligomers specific to the pO157 version of stcE indicate that the stcE gene is common to all tested strains of *E. coli* associated with bloody colitis and HUS, but the stcE gene is not present in enteroinvasive, enterotoxigenic or uropathogenic strains of *E. coli*. However, some closely related strains of enteropathogenic *E. coli* contain stcE, which suggests that StcE may be more widely distributed among diarrheagenic *E. coli* than appreciated initially. Additionally, a search of the GenBank database has identified at least one distant homolog to StcE: a *Vibrio cholerae* protein (designated TagA) of unknown function. We envision methods to screen for similar virulence factors produced by other microbes.

We discovered that in the presence of cells, StcE surprisingly potentiates the ability of C1-INH to reduce complement-mediated disruption of cells. Rather than reducing or destroying C1-INH serpin activity, the interaction between cell-associated StcE and C1-INH appears to enhance the ability of C1-INH to inhibit the classical complement cascade, thereby protecting cells from the lytic effects of complement activity. As detailed in the Examples, the addition of StcE-treated C1-INH to opsonized sheep erythrocytes and human serum significantly decreases erythrocyte lysis below that of equivalent amounts of native C1-INH alone. A decrease in complement activity when human serum was treated with StcE prior to the addition of sheep erythrocytes was also observed, which is likely due to the activity of StcE on the endogenous C1-INH found in serum. Furthermore, analysis of complement component deposition on erythrocyte surfaces indicates that StcE-treated C1-INH continues to act on its natural targets C1r and/or C1s.

StcE is unable to potentiate C1-INH activity in the absence of cells. Rather than directly modifying C1-INH to increase its ability to inhibit the complement cascade, StcE potentiation of C1-INH in the presence of cells may be due to tethering C1-INH to the cell surface, effectively increasing the local concentration of C1-INH at the sites of potential lytic complex formation.

Cleavage of C1-INH by StcE does not appear to be a factor in StcE potentiation of C1-INH protection against complement activity, as is evidenced by the ability of StcE E435D-His, a mutant protein defective in proteolytic activity against C1-INH, to protect erythrocytes to a degree comparable to that observed with wild-type StcE in vitro. The interaction between StcE and erythrocytes is specific, saturating the cells at approximately $1.8 \times 10^6$ molecules of StcE per cell. In turn, this allows a high affinity interaction between C1-INH and erythrocytes, reaching $2.25 \times 10^6$ molecules of C1-INH per cell in the presence of one μg of StcE. This amount of C1-INH (0.1 IU) is well within the physiological concentration of C1-INH found in serum, suggesting that this interaction may be biologically relevant in vivo.

Without being limited as to theory, we propose a model of the mechanism by which StcE potentiates C1-INH-mediated inhibition of classical complement in which StcE first interacts with the cell surface, followed by binding of StcE to the N-terminal domain of C1-INH to sequester the serpin to the cell surface. Alternatively, StcE may interact with C1-INH before binding to the cell surface. Cell-bound C1-INH binds to C1r and/or C1s of the C1 complex via the RCL, inactivating the serine protease. StcE then cleaves within the N-terminus of C1-INH, releasing the serpin/serine protease complex and a smaller, amino-terminal cleavage fragment of C1-INH from the cell surface. StcE binds to another C1-INH molecule, and the cycle described above is repeated.

The concept of C1-INH turnover at the cell surface may explain the observation that more C1-INH bound to erythrocytes in the presence of the proteolytically inactive StcE mutant than was bound in the presence of StcE'-His. Thus, the relatively slow cleavage rate of C1-INH by StcE may actually be beneficial to the potentiation of the serpin, as a more rapid rate of catalysis might not allow enough time for the inactivation of the C1 complex to occur. Additionally, the interaction of StcE with the N-terminal region of C1-INH while bound to the cell surface likely permits continued access of the serpin domain to its targets without compromising its activity. The binding of StcE to host cells might also allow the protease to be carried to sites distal to *E. coli* O157:H7 colonization in a manner similar to the Shiga toxin, thereby affecting C1-INH-regulated processes outside the local environment of bacterial infection. Finally, the observation that cell-bound C1-INH might affect leukocyte adhesion suggests StcE could influence the migration of inflammatory mediators to the sites of EHEC colonization.

Sequestration of complement inhibitors to bacterial surfaces can reduce complement activity and promote serum resistance. As demonstrated in the Examples, StcE-treated C1-INH acts in a similar by providing increased serum resistance to *E. coli* over native C1-INH. By preventing complement activity at such an early stage in the pathway via the recruitment of C1-INH to cells, StcE may also reduce the opsonization of *E. coli* O157:H7 by C3b and the production of the chemoattractant anaphylatoxins C3a and C5a. Because StcE is a secreted protein, the protection against complement activation may extend to the colonic epithelial cells colonized by *E. coli* O157:H7.

Although the Examples indicate that StcE has no effect on C1-INH-mediated inhibition of kallikrein in the absence of cells, it is reasonably expected that StcE-treated C1-INH may downregulate contact activation pathway initiated upon the interaction of Factor XII and prekallikrein with negatively charged surfaces.

In addition to its ability to sequester C1-INH to cell surfaces and cleave in the N-terminal region of C1-INH, we have discovered that StcE is capable of cleaving heavily glycosylated polypeptides and mucins, such as those found in saliva or sputum, including, but not limited to, MUC7 and gp-340/DMBT1.

The ability of StcE to cleave glycosylated polypeptides may facilitate colonization of the gut by *E. coli* O157:H7. The Examples below show that a StcE knockout mutant has impaired ability to form pedestals, but pedestal formation is restored by supplementation with exogenous StcE.

Elucidation of StcE functions suggests that StcE plays a role in the establishment and progression of EHEC infection and associated disease processes. StcE is therefore a promising potential target for chemotherapeutic or immune-based prevention or treatment of EHEC diseases. Active or passive immune prophylaxis using StcE as an antigen or anti-StcE antibodies may prevent the serious sequalae associated with infections by enterohemorrhagic *E. coli*.

The development of an assay for StcE activity as described herein below will facilitate screening of potential therapeutics for the ability to inhibit cleavage of the C1-INH.

Preferably, purified polypeptides will be used in the methods of the present invention (i.e., to assay potential StcE inhibitors or to elicit an immune response in an animal). As used herein, a purified peptide is at least 95% pure, in that it contains no greater than 5% non StcE peptide sequences. More preferably, purified StcE polypeptides are at least 97% pure, or even as much as at least 99% or more pure. Purified polypeptides may be obtained by standard biochemical purification means, or by engineering recombinant proteins to include affinity tags that facilitate purification from complex biological mixtures.

In the examples below, polyclonal antibodies were raised against a His-tagged StcE protein that was first purified by immobilized metal affinity chromatography (IMAC) using nickel-agarose beads, followed by separation by SDS-PAGE, and excision of the band of the appropriate size from the gel. The antibodies were found to bind specifically to StcE polypeptide. One of skill in the art will appreciate that using standard methods, monoclonal antibodies useful in the practice of the present invention could be raised against a polypeptide comprising the amino acid sequence of amino acid residues 24-886 of SEQ ID NO:2 or against shorter consecutive peptide sequences thereof.

It is expected that antibodies directed against StcE will bind to and reduce StcE activity. For example, it is expected that including anti-StcE antibodies in assays of the ability of StcE-producing strains of *E. coli* to form pedestals would result in reduced pedestal formation. Similarly, anti-StcE antibodies could be expected to reverse StcE-potentiated C1-INH protection of cells from disruption by complement activation, to interfere with cleavage of StcE by C1-INH in a cell-free assay, and to interfere with the ability of StcE to cleave other heavily glycosylated polypeptides.

It is envisioned that an antibody preparation comprising at least one antibody that binds specification to a polypeptide comprising amino acid residues 24-886 of SEQ ID NO:2 could be used to passively immunize an animal at risk of infection by a bacterium expressing a StcE protein. This would be particularly useful for treating cows or humans believed to have been exposed to EHEC.

In view of the multiple functions that StcE appears to play in protecting the bacteria against or overcoming host defense mechanisms, purified polypeptides comprising a sequence of at least 17, 25, or 40 consecutive amino acids of SEQ ID NO:2 may be particularly useful as an immunogen for eliciting an immune response in cattle or humans. Suitably, the full length StcE or StcE E435D could be used as an immunogen.

The Examples below show that StcE is able to cleave mucins or other glycosylated polypeptides to reduce the viscosity of or solubilize the materials. It is specifically envisioned that the StcE could be used to cleave glycosylated polypeptides, thereby reducing the viscosity of the material comprising the polypeptides. The ability of StcE to cleave glycosylated polypeptides and reduce viscosity of sputum or pulmonary secretions would be of potential benefit to people with cystic fibrosis (CF). In a CF patient, the thickness of the mucus layer prevents clearance by normal mechanisms. It is envisaged that StcE cleavage of gp340 and MUC7 will reduce the aggregation activities of gp340 and MUC7, and aid mucus clearance in the CF patient. This may reduce the risk of infection and/or potentiate the efficacy of pharmaceuticals, e.g., antibiotics. Furthermore, potentiation of C1-INH-mediated inhibition of the inflammatory pathways by StcE may also benefit people with cystic fibrosis by reducing inflammation.

It is also envisioned that the ability of StcE to cleave glycosylated polypeptides and reduce the viscosity of saliva and other mucous materials would make it useful in a mucosal vaccine in conjunction with a target antigen of interest (i.e., an antigen against which one wishes to illicit an immune response in an animal) because it may enhance access of the target antigen to target cells.

As one of skill in the art would appreciate, a StcE protein comprising an amino acid sequence having minor substitutions, deletions, or additions from that of the SEQ ID NO:2 would be suitable in the practice of the present invention. Conservative amino acid substitutions are unlikely to perturb the protein's secondary structure and interfere with its activity. SEQ ID NO:2 includes the N-terminal signal sequence, which although expressed, is unlikely to be found on an isolated polypeptide. The expressed StcE protein likely undergoes post translational modification that results in cleavage of the N-terminal signal peptide. The N-terminus of secreted StcE was purified from supernatants of an *E. coli* K-12 strian carrying pO157 was sequenced. As predicted, the N-terminal residues of secreted StcE (designated StcE') correspond to residues 24-27 of SEQ ID NO:2.

It is specifically envisioned that isolated polypeptides having less than the full length sequence of amino acid residues 24-886 of SEQ ID NOL:2 will be useful in the practice of the present invention. StcE polypeptides that are truncated at the N-terminal or C-terminal regions or having minor sequence variations may retain the ability to bind to and/or cleave C1-INH, to promote pedestal formation, to potentiate C1-INH mediated protection of cells, or cleave other glycosylated polypeptides other than or in addition to C1-INH. Whether a protein retains binding or proteolytic activity of can be evaluated using the methods set forth herein in the Examples, or by any suitable method.

It is expected that purified StcE polypeptides that are truncated at the N-terminal or C-terminal regions or a polypeptide comprising an amino acid sequence comprising at least 17 consecutive amino acid residues of SEQ ID NO:2 may be used as an antigen against which antibodies specific for StcE may be raised. Preferably, the polypeptide comprises at least 25 consecutive amino acid residues of SEQ ID NO:2. More preferably still, the polypeptide comprises at least 40 consecutive amino acid residues of SEQ ID NO:2. One of ordinary skill in the art could easily obtain any of the various polypeptides comprising a portion of SEQ ID NO:2 by subcloning a sequence encoding the polypeptide into an expression vector, introducing the expression vector into a suitable host cell, culturing the cell, and isolating the expressed polypeptide using standard molecular biological techniques.

Using the teachings of the specification, one of skill in the art could readily obtain a polypeptides having at least 95% amino acid identity to amino acid residues 24-886 of SEQ ID NO:2. Suitably, the polypeptide comprises a sequence having at least 97% or at least 99% amino acid identity to amino acid residues 24-886 of SEQ ID NO:2.

The following non-limiting examples are intended to be purely illustrative.

EXAMPLES

Identification and Characterization of StcE

A list of bacterial strains and plasmids is found in Table 1. Strains were constructed and plasmids were maintained in either *E. coli* K-12 DH1 or C600 unless otherwise noted. Recombinant DNA manipulations were performed by standard methods.

Enterohemorrhagic *Escherichia coli* strains EDL933 and EDL933cu (lacking plasmid pO157) and WAM2371 (enteropathogenic *E. coli* strain E2348/69) were provided by Dr. Alison O'Brien of the Uniformed Services University. WAM2035 (C600/pO157) was provided by Dr. Hank Lockman of the Uniformed Services University. WAM2516 (*Citrobacter rodentium* strain DBS 100) was provided by Dr. David Schauer of the Massachusetts Institute of Technology. The Diarrheagenic *E. coli* (DEC) collection was a gift from Dr. Tom Whittam of the University of Pennsylvania. WAM2547 was created by transforming pLOF/Km (a gift from Dr. Victor De Lorenzo of the GBF-National Research Centre for Biotechnology, Germany) into the donor strain S17(λpir).

TABLE 1

Bacterial strains and plasmids used in this study.

| Strain | Relevant phenotype or plasmid genotype | Source |
|---|---|---|
| C600 | *E. coli* K-12 | this laboratory |
| DH1 | laboratory strain of *E. coli* | this laboratory |
| S17(⊠pir) | *E. coli* donor strain for conjugation | this laboratory |
| BL21(DE3) | *E. coli* strain for protein overexpression | Novagen |
| EDL933 | wild-type EHEC strain | A. O'Brien |
| EDL933cu | EHEC strain EDL933 cured of pO157 | A. O'Brien |
| WAM2371 | EPEC strain E2348/69 | A. O'Brien |
| WAM2516 | *C. rodentium* strain DBS100 | D. Schauer |
| DEC strains | Diarrheagenic *E. coli* collection | T. Whittam |
| WAM2035 | C600/pO157::Tn801 (amp$^r$) | H. Lockman |
| WAM2515 | C600/pO157::Tn801 (amp$^r$ nal$^r$) | this study |
| WAM2297 | DH1/pBluescript II SK+ (amp$^r$) | this laboratory |
| WAM2547 | S17(⊠pir)/pLOF/Km (amp$^r$ kan$^r$) | this study |
| WAM2553 | C600/pWL104 (amp$^r$ kan$^r$) | this study |
| WAM2562 | DH1/pWL105 (amp$^r$) | this study |
| WAM2572 | BL21(DE3)/pWL107 (kan$^r$) | this study |
| WAM2726 | BL21(DE3)/pTEG1 (kan$^r$) | this study |
| WAM2815 | EDL933 with stcE replaced by cat | this study |
| WAM2997 | WAM2815 strain with stcE at the Tn7att site | this study |
| pLOF/Km | pGP704 carrying miniTn10kan | V. De Lorenzo |
| pO157 | 92 kb plasmid of EDL933; Tn801 at base 5413 | H. Lockman |
| pBluescript II SK+ | cloning vector | Stratagene |
| pET24d(+) | 6xHis overexpression vector | Novagen |
| pWL104 | pO157::miniTn10kan inserted at base 23772 | this study |
| pWL105 | pBluescript II SK+/bases 1-2798 of L7031 | this study |
| pWL107 | pET24d(+)/bases 138-2795 of L7031 | this study |
| pTEG1 | pWL107 with amino acid change E435D | this study |

WAM2515 is a spontaneous nalidixic acid-resistant mutant of WAM2035. WAM2553 was created as described below, containing a mini-Tn10kan insertion at base 23772 of pO157 (accession #AF074613). This plasmid is designated pWL104. WAM2297 is pBluescript II SK+ in DH1. pWL105 was constructed by amplifying bases 1 to 2798 of the promoter and gene L7031/stcE from pO157 by polymerase chain reaction (PCR) using primer pairs 5'-CCCTC-GAGTTTACGAAACAGGTGTAAAT-3' (SEQ ID NO:4) and 5'-CCTCTAGATTATTTATATACAACCCTCATT-3' (SEQ ID NO: 5); and cloning the product into the XbaI-XhoI sites of pBluescript II SK+ (Stratagene); WAM2562 is DH1 containing pWL105. pWL107 was constructed by PCR amplification of bases 138 to 2798 of the promoter and gene L7031/stcE from pO157 by PCR using primer pairs 5'-CCGAGCTCCGATGAAATTAAAGTAT-CTGTC-3' (SEQ ID NO:6) and 5'-CCTCGAGTTTATATACAACCCT-CATTG-3' (SEQ ID NO:7); and cloning the PCR product into the SacI-XhoI sites of pET-24d(+) (Novagen);

WAM2572 is BL21(DE3) (Novagen) transformed with pWL107. The creation of WAM2726 is described below. All chemicals were purchased from Sigma (St. Louis, Mo.) unless stated otherwise.

Cell Lines

All cell lines were maintained in RPMI 1640 medium (Gibco) supplemented with 10% fetal bovine serum (HyClone) and 10 µg/ml gentamicin at 37° C. with 5% $CO_2$. The human T cell line Jurkat clone E6-1, the human promyelocytic leukemia line HL-60, and the human B cell lymphoma line Raji were obtained from ATCC, the human promyelocytic leukemia line U937 was a gift from Dr. Jon Woods of the University of Wisconsin-Madison, and the human T cell lymphoma line MOLT-4 was a gift from Dr. David Pauza of the University of Wisconsin-Madison.

Aggregation Assays.

Bacterial strains were grown overnight in Lennox L broth (with antibiotic selection when appropriate) at 37° C. with agitation. Cultures were washed once with phosphate buffered saline (PBS) and resuspended in 1/10 the original culture volume in PBS. Cultures were lysed in a French Press at 20,000 lbs/in². The resulting lysates were spun at 1000×g to remove debris and protein concentrations were determined by the Bradford protein assay (Bio-Rad). Tissue culture cells were suspended at $10^6$ cells/ml in RPMI 1640 and 50 µg/ml gentamicin with 10% FBS or human serum. Fifty µg/ml of lysates or 50-200 ng/ml purified StcE-His (see below) were added to cells and incubated for two hours at 37° C. in 5% $CO_2$. Cells were agitated for one minute to disrupt spontaneous aggregates before visualization. Similar assays were performed in the absence of serum or with ammonium sulfate-precipitated fractions of human serum (see below); cells were washed once in RPMI 1640 and resuspended at $1 \times 10^6$ cells/ml in RPMI 1640 with 50 µg/ml gentamicin (and human serum fractions, if indicated) before the addition of lysates or StcE-His. When indicated, ethylenediaminetetraacetic acid (EDTA) or bathophenanthroline-disulfonic acid (BPS) were added to the assays at a final concentration of 5 mM.

Identification of StcE

WAM2515 was mated with WAM2547 as described (7). Transconjugants were plated onto LB plates containing 100 µg/ml ampicillin, 50 µg/ml kanamycin, and 50 µg/ml nalidixic acid. Transconjugants were resuspended in 1×TES, washed once with 1×TES, and pO157/pO157::miniTn10kan were isolated by midi-prep (Qiagen). pO157/pO157::mini-Tn10kan were transformed into C600 and plated onto LB plates containing 100 µg/ml ampicillin and 50 µg/ml kanamycin. Transformants were grown overnight in Lennox L broth containing 100 µg/ml ampicillin and 50 µg/ml kanamycin at 37° C. with agitation and lysates were screened for the ability to aggregate Jurkat cells as described above. pO157::mini-Tn10kan was isolated from clones lacking the ability to aggregate Jurkat cells and the location of the transposable element was identified by sequence analysis. One clone unable to aggregate Jurkat cells was designated WAM2553.

Purification of Recombinant StcE-His

StcE-His was purified according to the manufacturer's instructions (Novagen). Briefly, WAM2572 was induced to produce StcE-His by the addition of IPTG to 1 mM at an O.D. of 0.5 followed by vigorous aeration at 37° C. for approximately three hours. The cells were lysed in a French Press at 20,000 lbs/in² and the resulting lysate was centrifuged at 20,000×g for 15 minutes. The insoluble pellet was resuspended in a buffer containing 5 mM imidazole and 6 M urea and the inclusion bodies were solubilized for one hour on ice. This fraction was incubated with nickel-agarose beads (Qiagen) overnight at 4° C., and the beads were washed three times with a buffer containing 60 mM imidazole and 6 M urea. Purified StcE-His was eluted from the beads with a buffer containing 300 mM imidazole and 6 M urea. Eluted StcE-His was dialyzed against three changes of PBS/20% glycerol at 4° C. to remove the imidazole and urea. Protein concentration was determined by SDS-PAGE using purified β-galactosidase as a standard. At our request, polyclonal antibodies to purified StcE-His were prepared in rabbits by Cocalico Biologicals, Inc. Briefly, purified StcE-His was electrophoresed on an 8% polyacrylamide gel and stained with Coomassie Brilliant Blue. StcE-His was excised from the gel and injected into rabbits. Rabbits were boosted with StcE-His once a month for six months prior to exsanguinations.

Two-Dimensional Gel Electrophoresis

Human serum was fractionated by ammonium sulfate precipitation, dialyzed against three changes of RPMI 1640 (Gibco) overnight at 4° C., and protein concentration was determined by Bradford assay (Bio-Rad). When indicated, protein A-sepharose was used to remove fractions of IgG. Two-dimensional electrophoresis was performed according to the method of O'Farrell (8) by Kendrick Labs, Inc. (Madison, Wis.) as follows: isoelectric focusing was carried out on 25 µg of 30-60% ammonium sulfate-fractionated human serum removed of IgG in glass tubes of inner diameter 2.0 mm using 2.0% pH 3.5-10 ampholines (Amersham Pharmacia Biotech) for 9600 volt-hrs. Fifty ng of an IEF internal standard, tropomyosin, was added to each sample. This protein migrates as a doublet with lower polypeptide spot of MW 33,000 and pI 5.2; an arrow on the stained gel marks its position. The enclosed tube gel pH gradient plot for this set of ampholines was determined with a surface pH electrode.

After equilibration for 10 min in buffer "O" (10% glycerol, 50 mM dithiothreitol, 2.3% SDS and 0.0625 M Tris, pH 6.8) each tube gel was sealed to the top of a stacking gel that is loaded on the top of a 8% acrylamide slab gel (0.75 mm thick). SDS slab gel electrophoresis was carried out for about 4 hrs at 12.5 mA/gel. The following proteins (Sigma) were added as molecular weight standards to a well in the agarose which sealed the tube gel to the slab gel: myosin (220 kDa), phosphorylase A (94 kDa), catalase (60 kDa), actin (43 kDa), carbonic anhydrase (29 kDa), and lysozyme (14 kDa). These standards appear as bands on the basic edge of the special silver-stained (O'Connell and Stults 1997) 8% acrylamide slab gel. The gel was dried between sheets of cellophane with the acidic edge to the left.

A similar gel was run as described above with the following differences: 250 µg of 30-60% ammonium sulfate-fractionated human serum was loaded onto the IEF gel; the second dimension was run on a 10% acrylamide slab gel and stained with Coomassie Brilliant Blue.

Far Western Blot Analysis

One hundred µg of 30-60% ammonium sulfate-fractionated human serum was run on a two-dimensional gel as described above but without staining. After slab gel electrophoresis the gel for blotting was transferred to transfer buffer (12.5 mM Tris, pH 8.8, 86 mM glycine, 10% methanol) and transblotted to PVDF membrane overnight at 200 mA and approximately 50 volts/gel. The PVDF membrane was blocked with 2% milk (Difco) in buffer AD (20 mM Tris, pH 7.5, 100 mM NaCl, 10% glycerol, 0.01% Tween-20) at 4° C. Two µg/ml purified StcE-His was added to the PVDF membrane and allowed to incubate two hours at 4° C. The membrane was washed with buffer AD and blocked with 2% milk in buffer AD. The membrane was reacted with polyclonal anti-His antibody conjugated with horse-radish peroxidase (Santa Cruz), washed with buffer AD, and developed with the LumiGlo chemiluminescence detection system (Kirkegaard & Perry Laboratories). The PVDF membrane was then stripped (62 mM Tris, pH 6.8, 2% SDS, 10 mM β-mercaptoethanol (β-ME), 30 min, 50° C.), washed with buffer AD, reacted as above with only the His-HRP antibody, and developed.

Mass Spectrometry

Of the three spots in human serum that reacted with purified StcE-His as identified by Far Western blotting, only the leftmost spot (the most acidic) of approximately 100 kDa was accessible for analysis by mass spectrometry. This spot was cut from the Coomassie Brilliant Blue-stained 10% slab gel and sent to the Protein Chemistry Core Facility at the Howard Hughes Medical Institute/Columbia University for analysis. The spot was digested with endoproteinase Lys-C and analyzed by MALDI-MS. The peptide pattern was compared against known human proteins in the SWISS-PROT database and was identified as plasma protease C1 inhibitor.

Electrophoresis and Immunoblot Analyses

Fifty μg whole and ammonium sulfate-precipitated human serum fractions were incubated with 500 ng purified StcE-His in 500 μl buffer AD for two hours at room temperature and precipitated with 10% trichloroacetic acid (TCA) on ice for one hour. Precipitates were collected by centrifugation, resuspended in 1× sample buffer (2% SDS, 10% glycerol, 5% β-ME, 1 mM bromophenol blue, 62 mM Tris, pH 6.8), and heated to 95-100° C. for 5 min prior to electrophoresis on 8% polyacrylamide gels. Separated proteins were transferred to Hybond ECL nitrocellulose (Amersham Pharmacia Biotech) as described (9) for immunoblot analysis. Blots were blocked with 5% milk in TBST (154 mM NaCl, 20 mM Tris, pH 7.6, 0.1% Tween-20), probed with a polyclonal anti-C1 inhibitor antibody (Serotec) and then with HRP-conjugated anti-rabbit secondary antibody (Bio-Rad) before developing as described above.

Sixteen μg purified C1 inhibitor (Cortex Biochem) were incubated with 4.8 μg purified StcE-His in 480 μl buffer AD at room temperature; 30 μl of the reaction were removed at various time points, suspended in 1× sample buffer, and heated to 95-100° C. for 5 min prior to electrophoresis on 8% polyacrylamide gels. Separated proteins were transferred to nitrocellulose and reacted with anti-C1 inhibitor antibody as described above.

EDL933, EDL933cu, WAM2035, and WAM2553 were grown in Lennox L broth at 37° C. overnight, centrifuged, and the culture supernatant was removed. The supernatant was precipitated with ammonium sulfate and the 0-60% fraction was resuspended at 1/100 the original culture volume and dialyzed against three changes of PBS overnight at 4° C. Twenty μl of the dialyzed supernatants and 30 μg of EDL933, EDL933cu, WAM2035, and WAM2553 lysates were suspended in 1× sample buffer and heated to 95-100° C. for 5 min prior to electrophoresis on 8% polyacrylamide gels. Separated proteins were transferred to Hybond ECL nitrocellulose and reacted with polyclonal anti-StcE-His antibody, followed by anti-rabbit-HRP secondary antibody.

Casein Proteolysis Assay

Various concentrations of StcE-His were incubated with BODIPY FL-conjugated casein for various times using the EnzChek Protease Assay Kit (Molecular Probes, Inc.) and the increase in fluorescence was measured with a fluorimeter as per the manufacturer's instructions.

Lysates of *E. coli* Strains Carrying pO157 Induce the Aggregation of Transformed Human T Cell Lines in a Serum-Dependent Manner.

To determine the consequence of pO157-containing *E. coli* products on Jurkat cells, a human T cell lymphoma line, 50 μg/ml of lysates of strains EDL933, EDL933cu, WAM2035, WAM2371, WAM2516, and C600 were applied to 1×10⁶ Jurkat cells/ml in RPMI 1640 with 10% FBS and 50 μg/ml gentamicin for two hours at 3° C. in 5% $CO_2$. After agitation for one minute to disrupt spontaneous aggregates, Jurkats were observed for the induction of aggregation. Lysates of *E. coli* strains carrying pO157 induced the aggregation of Jurkat cells while lysates of strains lacking pO157 did not (FIG. 1). Lysates of other pathogenic bacteria such as enteropathogenic *E. coli* strain E2348/69 (WAM2371) and *C. rodentium* (WAM2516) capable of inducing the attaching and effacing (A/E) phenotype on intestinal epithelial cells and carrying large virulence plasmids different from pO157 were unable to induce the aggregation of Jurkat cells. To determine whether this effect was specific for Jurkat cells or could induce the aggregation of a broader host cell range, 1×10⁶ cells/ml in RPMI 1640 with 10% FBS and 50 μg/ml gentamicin of another human T cell lymphoma line, MOLT-4, two human promyelocytic leukemia cell lines, HL-60 and U937, and a human B cell lymphoma line, Raji, were treated with 50 μg/ml of EDL933 and WAM2035 lysates for two hours at 3° C. in 5% $CO_2$. pO157-containing lysates aggregated MOLT-4 cells but not HL-60, U937, or Raji cells (data not shown), indicating T cell specificity for the phenotype.

To determine the serum requirement for the induction of aggregation, 50 μg/ml of lysates of EDL933 and WAM2035 were applied to 1×10⁶ Jurkat cells/ml with 10% human serum and 50 μg/ml gentamicin for two hours at 3° C. in 5% $CO_2$. As seen with FBS, pO157-containing lysates were able to induce the aggregation of Jurkat cells in the presence of human serum. However, EDL933 and WAM2035 lysates were unable to induce the aggregation of Jurkat cells under the same conditions in the absence of serum. To further characterize the component(s) of human serum responsible for mediating Jurkat cell aggregation in the presence of StcE, we fractionated human serum by ammonium sulfate precipitation followed by dialysis in RPMI 1640. We found that 0-30% and 30-60%, but not 60-100%, ammonium sulfate-precipitated human serum was able to mediate aggregation of Jurkat cells in the presence of StcE. This indicates a factor or factors in serum is required for the aggregation of Jurkat cells when treated with lysates of pO157-containing bacteria.

Identification and Cloning of stcE

To localize the gene(s) on pO157 responsible for the induction of aggregation of human T cell lines, we subjected pO157 to mutagenesis using a minitransposon. Lysates of recombinant strains of *E. coli* containing pO157 mutagenized with mini-Tn10kan were tested for the ability to aggregate Jurkat cells in RPMI 1640 with 10% FBS and 50 μg/ml gentamicin. pO157::mini-Tn10kan was isolated from clones whose lysates were unable to induce the aggregation of Jurkat cells. The location of the transposon insertion in WAM2553 was determined by sequence analysis and mapped to position 23772 of pO157. The open reading frame in which the transposon inserted was designated L7031 (10) and is located immediately 5' to the general secretory apparatus on pO157. L7031/stcE was amplified and cloned into the XbaI-XhoI sites of pBluescript II SK+. Lysates of WAM2562 induced aggregation of Jurkat cells in the presence of serum, whereas lysates of WAM2297 (DH1 carrying pBluescript II SK+) did not, which confirms that the stcE gene is responsible for the phenotype.

Figure 2:
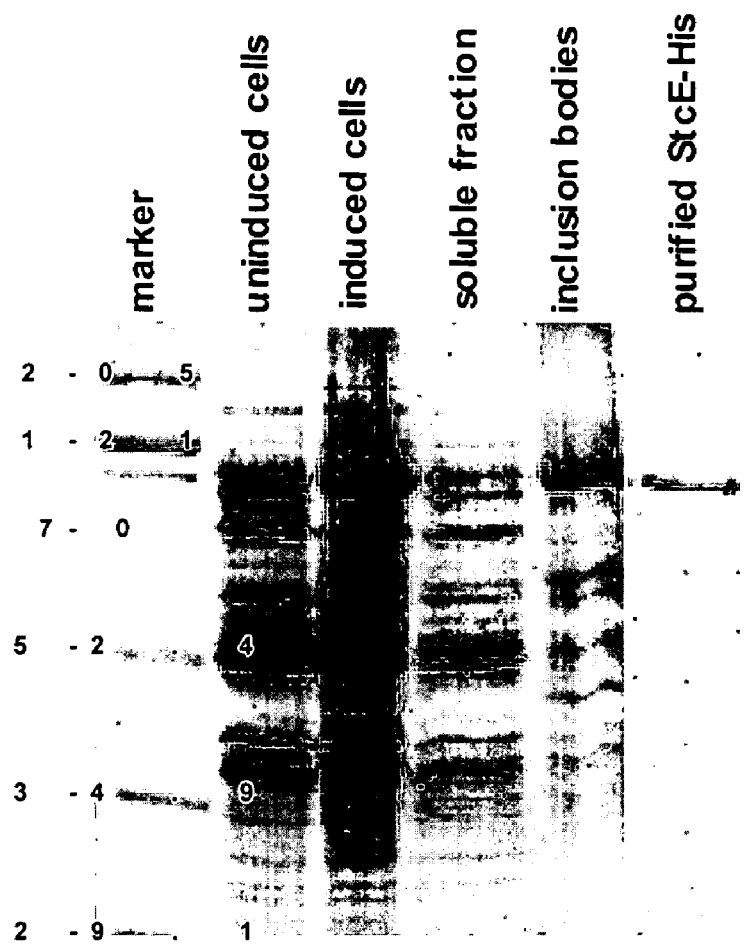
FIG. 2 shows stained proteins separated by SDS/PAGE.

Based on sequence analysis, we concluded that the translational start site for StcE was more likely to begin at base 138 than at base 102 (10). We therefore amplified the coding sequence for stcE from bases 138 to 2798 by PCR and cloned the gene in frame with a 6×His-tag at the 3' end of the fusion in pET24d(+). We were able to overexpress and purify a recombinant his-tagged form of StcE (StcE-His) (FIG. 2); this purified fusion protein was able to aggregate Jurkat cells in the presence of serum at a variety of concentrations (data not shown).

Localization and Characterization of StcE

Figure 3:
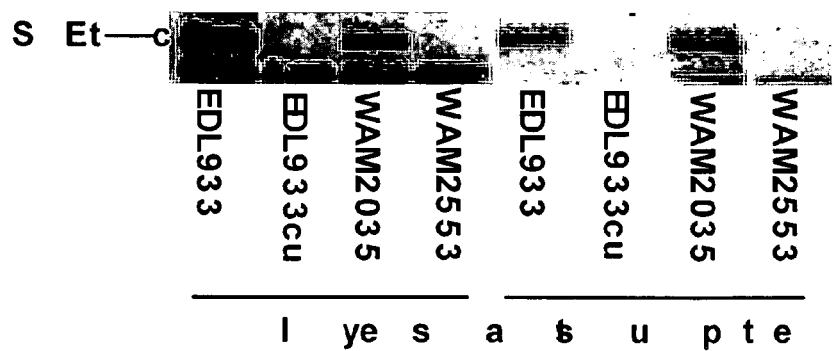
FIG. 3 shows that synthesis of StcE correlates with the presence of pO157.

Using antiserum to StcE-His, we performed immunoblot analysis to examine the expression and secretion of StcE by E. coli. StcE is expressed by E. coli strains carrying pO157 at 3° C. in Lennox L broth but not in strains lacking pO157 or harboring a transposon insertion in stcE (FIG. 3). Additionally, StcE is released into the culture supernatant by strains carrying pO157 under the same growth conditions (FIG. 3). As StcE contains a putative cleavable N-terminal signal sequence, it is possible that StcE is actively released from the bacterium by the general secretory apparatus encoded on pO157.

StcE-mediated Jurkat cell aggregation is inhibited by the addition of ion chelators such as EDTA, a broad chelator of divalent cations, and BPS, a chelator specific for zinc and iron ions (data not shown). This suggests that StcE has a requirement for one or more divalent cations, most likely zinc. This is supported by the presence of an exact match to the histidine-rich consensus active site for metalloproteases, which coordinate zinc ions for activity (see discussion).

StcE-His interacts with a human serum protein(s) of approximately 105 kDa. To identify the factor(s) in human serum responsible for mediating Jurkat cell aggregation in the presence of StcE, the 30-60% ammonium sulfate-precipitated fraction of human serum was separated on a two-dimensional gel and transferred to a PVDF membrane. Using purified StcE-His as a probe, we performed Far Western blot analysis on the PVDF membrane, detecting any interactions between StcE-His and human serum proteins with an HRP-conjugated anti-His antibody. We found that StcE-His interacts with three spots of approximately 105 kDa ranging from very acidic to very basic in isoelectric point (data not shown). Probing the same membrane with only the HRP-conjugated anti-His antibody revealed that the three spots of approximately 105 kDa were specific for StcE-His (data not shown).

To identify these proteins, the 30-60% ammonium sulfate-precipitated fraction of human serum was removed of IgG and separated on another two-dimensional gel and either special silver stained or stained by Coomassie Brilliant Blue. The most acidic of the three spots (the leftmost spot) was well isolated from other proteins and excised from the Coomassie Brilliant Blue-stained gel. This spot was digested by endoproteinase Lys-C and analyzed by MALDI-MS. A comparison of the resulting peptide pattern with known human proteins in the SWISS-PROT database revealed a match with human plasma protease C1 inhibitor.

Cleavage of C1 inhibitor by StcE-His

Figure 4:
FIG. 4 shows that C1 inhibitor in human serum is cleaved by StcE.
Figure 4:
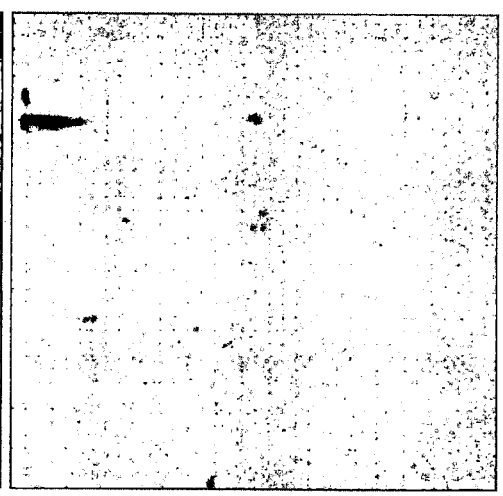

To confirm the interaction between StcE and human C1 inhibitor and to test the possibility that StcE may proteolyze C1 inhibitor, whole and ammonium sulfate-precipitated fractions of human serum were mixed with StcE-His, separated by SDS-PAGE, and transferred to nitrocellulose for immunoblot analysis. Using an anti-human C1 inhibitor antibody, we detected the presence of C1 inhibitor in samples lacking StcE-His and the absence of C1 inhibitor in samples containing StcE-His (FIG. 4). As predicted by Jurkat cell aggregation, the 0-30% and 30-60% ammonium sulfate-precipitated fractions of human serum were enriched for C1 inhibitor compared to the 60-100% fraction. After treatment with StcE-His, however, little to no C1 inhibitor could be detected in any of the fractions. The addition of EDTA or BPS to the mixture prevented the disappearance of C1 inhibitor from the serum samples, indicating a specific requirement for divalent cations, most likely zinc, for StcE activity (data not shown).

Figure 5:
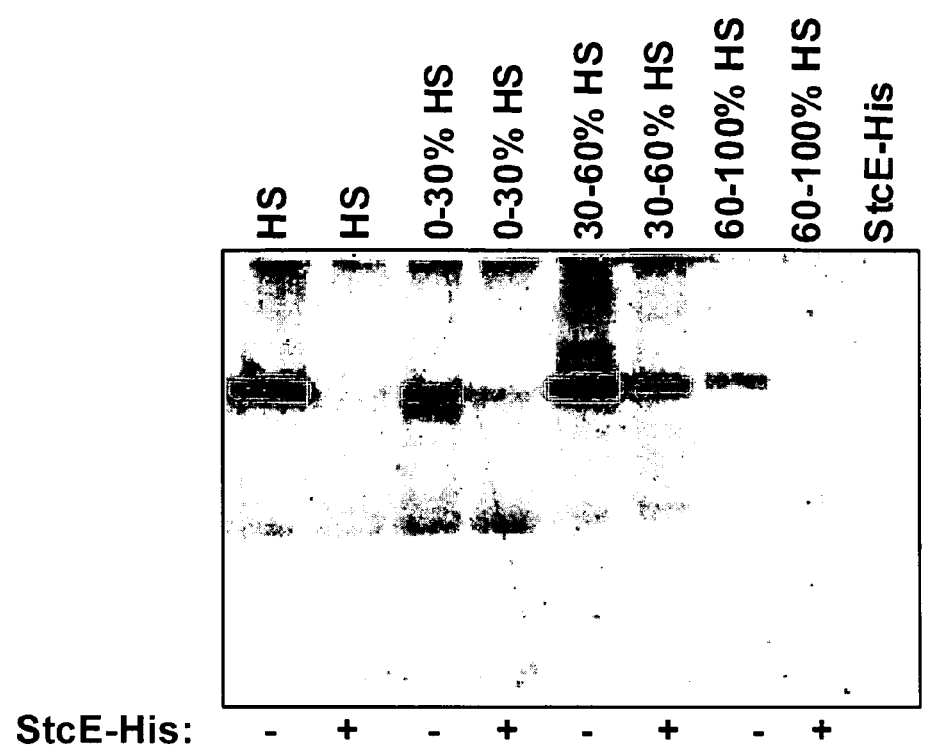
FIG. 5 shows cleavage of C1 inhibitor over time.

To confirm that the proteolysis of C1 inhibitor was a direct result of an interaction with StcE-His, we mixed purified human C1 inhibitor with StcE-His and removed aliquots of the reaction at various time points for analysis by immunoblot. Using an anti-human C1 inhibitor antibody, we detected the disappearance of a 105 kDa band corresponding to full-length C1 inhibitor and the appearance of an approximately 60 kDa cleavage product in a time-dependent manner (FIG. 5).

Examination of Patient Fecal Filtrates for StcE

Freshly passed stool samples from children with culture-positive E. coli O157:H7 (n=6), Campylobacter jejuni (n=2), Shigella B (n=2), or Clostridium difficile (n=2) infections were diluted 1:10 in PBS and passed through a 0.45 μm filter. Thirty μl of thawed filtrate was suspended in 1× sample buffer, heated (95-100° C. for 5 min) and electrophoresed on 8% polyacrylamide gels. Separated proteins were transferred to nitrocellulose and probed with a polyclonal antibody to StcE-His as described above. Twenty μl of the same samples was added to $1 \times 10^6$/ml Jurkat cells in 10% FCS and gentamicin (50 μg/ml) for 24 hours at 37° C. in 5% $CO_2$ to determine the ability of the filtrates to aggregate Jurkat cells.

Construction and Analyses of StcE E435D-His Mutant

The StcE E435D-His mutant was created using the PCR-based method of overlap extension (Horton et al. 1993). The first two PCR reactions were (i) stcE top strand primer 587 (5'-CCGCTCCGGTGAACTGGAGAATA-3') (SEQ ID NO:8) with its partner mutagenic primer 592 (5'-GACCAT-AATTATGACCAACATCATGACTGA-3') (SEQ ID NO:9) and (ii) stcE bottom strand primer 573 (5'-CCTTATCTGCG-GAGGCTGTAGGG-3') (SEQ ID NO:10) with its partner mutagenic primer 574 (5'-TGAGTTCAGTCATGATGTTG-GTCATAATTAT-3') (SEQ ID NO:11). Each reaction used 50 μM of each primer, about 100 ng of template DNA, and Deep Vent polymerase (New England Biolabs) in a 100 μl reaction. The reactions were run in a thermocycler under appropriate conditions (11) and the resulting products were purified on a 1% agarose gel using the QIA-quick Gel Extraction Kit (Qiagen). The next PCR reaction contained 5 μl each of the gel-purifed fragments, along with the stcE primers 587 and 573 and Deep Vent polymerase in a 100 μl reaction. The PCR products were gel-purified as above and cut with the restriction endonucleases PmeI and BsrG1. pWL107 was also cut with PmeI and BsrG1 and the mutant PCR product was ligated into pWL107, creating pTEG1. The base substitution was confirmed by sequence analysis. pTEG1 was transformed into E. coli strain BL21 (DE3) to create WAM2726 and StcE E435D-His (SEQ ID NO:19) was overexpressed and purified from this strain as described above. The purified protein was then analyzed for its ability to aggregate Jurkat cells as described above.

Purified C1-INH (one μg) was mixed with or without StcE-His (one μg) or StcE E435-His (one μg) overnight at room temperature in 500 μl buffer AD, precipitated with TCA (to 10%), electrophoresed on an 8% polyacrylamide gel, and transferred to nitrocellulose before analysis by immunoblot with an anti-C1-INH antibody as described above.

Purified C1-INH (500 ng) and human serum (50 µg) were electrophoresed on an 8% polyacrylamide gel in duplicate and the separated proteins were transferred to nitrocellulose for Far Western analysis. Essentially the same protocol was followed as described above with the following difference: one blot was probed with purified StcE-His (2 µg/ml) and the other with purified StcE E435D-His (2 µg/ml).

Colony Blot Analysis

A one kb fragment of stcE was PCR amplified from pO157 using the primers stcE5'846 (5'-GAGAATAATC-GAATCACTTATGCTC-3') (SEQ ID NO:12) and stcE3'1773 (5'-CGGTGGAGGAACGGCTATCGA-3') (SEQ ID NO:13) under standard reaction conditions. The PCR product was purified on a 1% agarose gel using the QIA-quick Gel Extraction Kit (Qiagen) and fluorescein-labeled using the ECL random prime labeling system (Amersham Life Science). Bacterial strains from the DEC collection, EDL933, and EDL933cu were patched onto sterile Magna Lift nylon transfer membranes (Osmonics) on LB plates and grown overnight at room temperature. Colonies were lysed by placing the membranes on 3MM Whatman paper soaked in 0.5 M NaOH. Neutralization was performed by placing the membranes first on 3MM Whatman paper soaked in 1 M Tris, pH 7.5 and then on 3MM Whatman paper soaked in 0.5 M Tris, pH 7.5/1.25 M NaCl. DNA was then crosslinked using a UV stratalinker. The blots were pre-hybridized in Church buffer (0.5 M dibasic sodium phosphate, pH 7.3, 7% SDS, 1% BSA, 1 mM EDTA) at 65° C. for one hour before the addition of the labeled probe. Hybridization proceeded overnight at 65° C. The membranes were then washed at 65° C. in 1×SSC/0.1% SDS for 15 minutes and then in 0.5×SSC/0.1% SDS for 15 minutes. The membranes were incubated with an anti-fluorescein labeled, HRP-conjugated antibody. The membrane was developed using the LumiGLO Chemiluminescent Substrate Kit (Kirkegaard and Perry Laboratories).

PCR Analysis of StcE

Oligonucleotides were designed to amplify by PCR regions of stcE to cover the length of the ~2.8 kbp promoter and gene. Primers stcE5'1 (5'-TTTACGAAACA-GGTG-TAAATATGTTATAAA-3') (SEQ ID NO:14) and stcE3'845 (5'-CAGTTCACCG-GAGCGGAACCA-3') (SEQ ID NO:15) covered the first third, stcE5'846 and stcE3'1773 covered the middle third, and stcE5'1774 (5'-GCTTCAGC-AAGTGGAATGCAGATAC-3') (SEQ ID NO:16) and stcE3'2798 (5'TTATTTAT-ATACAACCCTCATTGAC-CTAGG-3') (SEQ ID NO:17) covered the final third. Genomic DNA was isolated from *E. coli* strains DEC3A-E, DEC4A-E, DEC5A-E, EDL933, and EDL933cu using the Wizard Genomic DNA Purification Kit (Promega) as per the manufacturer's instructions. PCR was performed using 20 pM of each primer, about 100 ng of template DNA, and Deep Vent polymerase (New England Biolabs) in a 100 µl reaction. The reactions were run in a thermocycler under standard conditions. PCR products were electrophoresed on 1% agarose gels and visualized with ethidium bromide.

Isolation and Analyses of Bacterial Culture Supernatants

*E. coli* strains DEC3A-E, DEC4A-E, DEC5A-E, EDL933, and EDL933cu were grown in Lennox L broth at 37° C. overnight. Culture supernatants were harvested by centrifugation at 4° C. for 15 minutes at 10,000×g and filtered through a 0.45 µm filter. Supernatants were precipitated with ammonium sulfate to 75% saturation. The precipitates were centrifuged for 15 minutes at 16,000×g at 4° C. and resuspended in buffer AD. The resuspended precipitates were dialyzed against three changes of AD buffer overnight to remove residual ammonium sulfate.

Purified CI-INH (one µg) was mixed with 200 µl of ammonium sulfate-precipitated culture supernatants at room temperature overnight in a total volume of 500 µl buffer AD before precipitation with TCA (to 10%) and electrophoresis on 8% polyacrylamide gels. Separated proteins were transferred to nitrocellulose and immunoblot analysis was performed with an anti-C1-INH antibody as described above. Culture supernatants alone were separated on 8% polyacrylamide gels and transferred to nitrocellulose before immunoblot analysis was performed using an anti-StcE-His antibody as described above.

Specificity of StcE-His for C1-INH

To evaluate the specificity of StcE-His, potential target proteins (listed in Table 2), target protein (2 µg) was mixed with either StcE-His (1.28 µg) or *Pseudomonas aeruginosa* elastase (20 ng) (Calbiochem EC# 3.4.24.26) overnight at 37° C. in 500 µl buffer AD (20 mM Tris, pH 7.5, 100 mM NaCl, 10% glycerol, 0.01% Tween-20) and precipitated with TCA (to 10%) prior to electrophoresis on 8-10% polyacrylamide gels. Proteins in the gels were then Coomassie-stained or transferred to nitrocellulose for immunoblot analysis as above.

Figure 6:
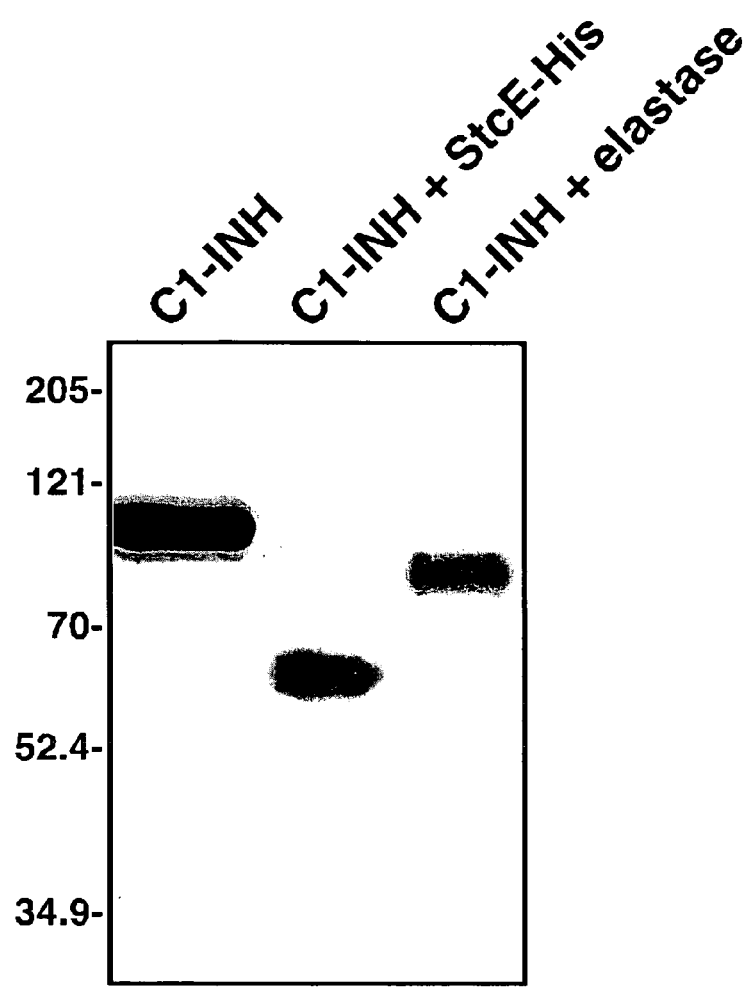
FIG. 6 shows differential cleavage of C1-INH by StcE and elastase.

StcE is able to cleave both purified and serum-associated C1-INH. Only C1-INH was cleaved by StcE-His; the sizes and staining intensities of all other potential substrates were the same in the presence and absence of StcE-His. In contrast, elastase degraded most of the proteins tested. Elastase treatment of C1-INH normally produces an inactive 95 kDa product (12), whereas treatment of C1-INH with StcE-His results in ~60-65 kDa C1-INH fragment(s) (FIG. 6). This indicates that the StcE cleavage site of C1-INH is distinct from that used by elastase. We employed a sensitive fluorimetric assay based on the digestion of a BODIPY FL-labeled casein substrate (EnzChek, Molecular Probes) to analyze further the ability of StcE-His to act as a non-specific endoprotease. Serial two-fold dilutions of StcE-His or *P. aeruginosa* elastase were mixed with the casein substrate per the manufacturer's instructions before fluorescent measurement of casein degradation. StcE-His was unable to degrade casein even at high protein concentrations (up to 6.4 µg/unit of volume), while elastase was able to act on casein at lower concentrations (range: 0.5 ng to 1 µg/unit of volume) (data not shown).

TABLE 2

Proteolysis of substrates incubated with StcE-His or *P. aeruginosa* elastase

| Substrate | StcE | Elastase |
| --- | --- | --- |
| C1 inhibitor (Cortex Biochem, San Leandro, CA) | + | + |
| α2-antiplasmin (Calbiochem, San Diego, CA) | − | + |
| α1-antitrypsin (Sigma, St. Louis, MO) | − | + |
| α1-antichymotrypsin (Sigma, St. Louis, MO) | − | + |
| antithrombin (Enzyme Research Labs, South Bend, IN) | − | + |
| α2-macroglobulin (Calbiochem, San Diego, CA) | − | + |
| von Willebrand factor (gift from Dr. D. Mosher, UW-Madison) | − | N.D. |
| collagen IV (Rockland, Gilbertsville, PA) | − | − |
| fibronectin (Calbiochem, San Diego, CA) | − | + |
| serum albumin (New England Biolabs, Beverly, MA) | − | N.D. |
| IgA1 (Cortex Biochem, San Leandro, CA) | − | + |
| Elastin (Sigma, St. Louis, MO) | − | + |
| Gelatin (BioRad, Hercules, CA) | − | + |

N.D. = not done

Two µg of the indicated protein substrates were mixed with 1.28 µg StcE-His or 20 ng *P. aeruginosa* elastase overnight at 37° C. prior to electrophoresis by SDS-PAGE and staining with Coomassie Brilliant Blue. StcE was unable to digest any of the proteins tested other than C1-INH, while *P. aeruginosa* elastase had activity against a broad range of targets.

Detection of StcE in Feces.

Figure 7:
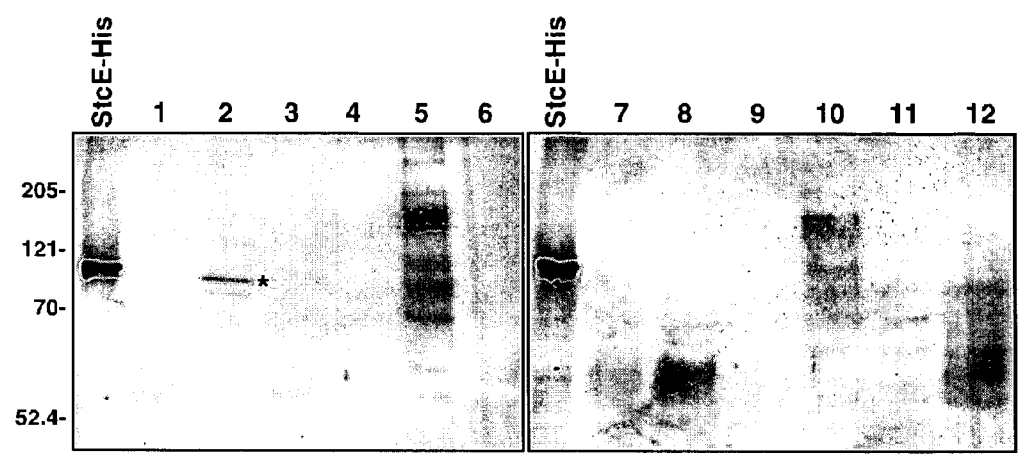
FIG. 7 is an immunoblot showing a StcE-reactive band in fecal filtrates.

The Shiga-like toxin has been identified in the feces of patients infected with *E. coli* O157:H7 (13, 14). To demonstrate that StcE is produced in vivo during an *E. coli* O157:H7 infection, we examined fecal filtrates collected from patients with *E. coli* O157:H7 and non-*E. coli* O157:H7-mediated diarrhea for the presence of StcE antigen and activity. Twelve fecal samples were diluted in PBS and filtered before analysis by immunoblot with polyclonal antibodies to StcE-His. A strongly reactive band with a molecular weight similar to StcE was present in the filtrate from one child infected with *E. coli* O157:H7 (FIG. 7, sample 2). Because StcE is able to mediate the aggregation of T cells, we examined the ability of the twelve fecal filtrates to aggregate Jurkat cells. Twenty µl of each filtrate was added to 5×10$^5$ Jurkat cells in the presence of 10% FCS. The one sample that contained a StcE-reactive species aggregated Jurkat cells to the same extent as 50 ng/ml purified StcE-His; all other samples were negative in this assay, even after 24 hours of incubation (data not shown).

StcE Contains a Zinc Metalloprotease Active Site.

Figure 8:
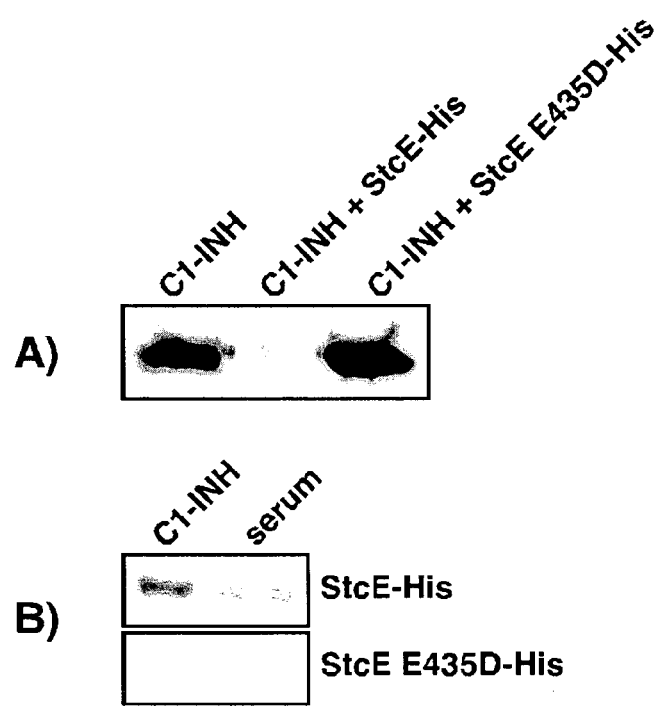
FIG. 8A shows that StcE E435D-His is unable to cleave C1-INH.
FIG. 8B shows that StcE E435D-His is unable to bind C1-INH.

As the predicted StcE amino acid sequence has a consensus $Zn^{2+}$-ligand binding site of metalloproteases (434: HEVGHNYGLGH) (SEQ ID NO:3), we examined the possibility that the glutamic acid residue at position 435 is critical for the proteolysis of C1-INH. This amino acid in other zinc metalloproteases acts as the catalytic residue for proteolysis (15) (16), and other researchers have shown that a conservative amino acid substitution from glutamic to aspartic acid disrupts the activity of the protease while maintaining its structure (15). By introducing a single change in the sequence of stcE at base 1442 from an A to a T, we created the same mutation and examined the ability of the recombinant mutant (StcE E435D-His) to digest C1-INH. While StcE-His is able to degrade C1-INH, we observed no such cleavage with the mutant protein (FIG. 8A) under the same conditions. The results of Far Western analysis (FIG. 8B) suggested that StcE E435D-His is unable to bind to C1-INH (or a similarly sized protein in human serum), which seemed to suggest that glutamic acid 435 is necessary for both binding and cleavage of C1-INH. The StcE-mediated aggregation of Jurkat cells was also affected by the E435D mutation. Jurkat cells will aggregate in response to StcE-His at concentrations as low as 1 ng/ml, while cells treated with as much as 200 ng/ml StcE E435D-His did not aggregate (data not shown). Thus, the glutamic acid residue at position 435 is critical for StcE-mediated aggregation of Jurkat cells, as well as proteolysis of C1-INH. However, based on subsequent results of studies involving StcE potentiation of C1-INH-mediated protection of cells, described in detail below, it appears that StcE E435D-His can in fact interact with C1-INH.

Detection of StcE Among Diarrheagenic *E. coli* Strains.

In order to establish the prevalence of stcE among other pathogenic strains of *E. coli*, we examined the Diarrheagenic *E. coli* (DEC) collection, a reference set of 78 *E. coli* strains provided by Dr. Tom Whittam of the University of Pennsylvania, for the presence of stcE. This collection contains a variety of enterohemorrhagic, enteropathogenic, and enterotoxigenic *E. coli* strains of different serotypes isolated from humans, non-human primates, and other mammals that are associated with disease symptoms, including diarrhea, hemorrhagic colitis, or HUS. The DEC collection is divided into 15 subgroups based on electrophoretic type, which is indicative of the genetic similarity of one strain to another. By using colony blot analysis, we found that all O157:H7 strains of *E. coli* (DEC3 and DEC4) contain DNA that hybridizes with an internal one kb region of stcE (Table 3). Surprisingly, three of five enteropathogenic O55:H7 strains of *E. coli* (DEC5A, C, & E) also hybridized with the stcE probe. Because O157:H7 strains are thought to have evolved from an O55:H7 predecessor, this result suggests a source of the stcE gene for current O157:H7 strains of *E. coli*. None of the other strains in the DEC collection hybridized with the stcE probe by colony blot analysis.

Figure 9:
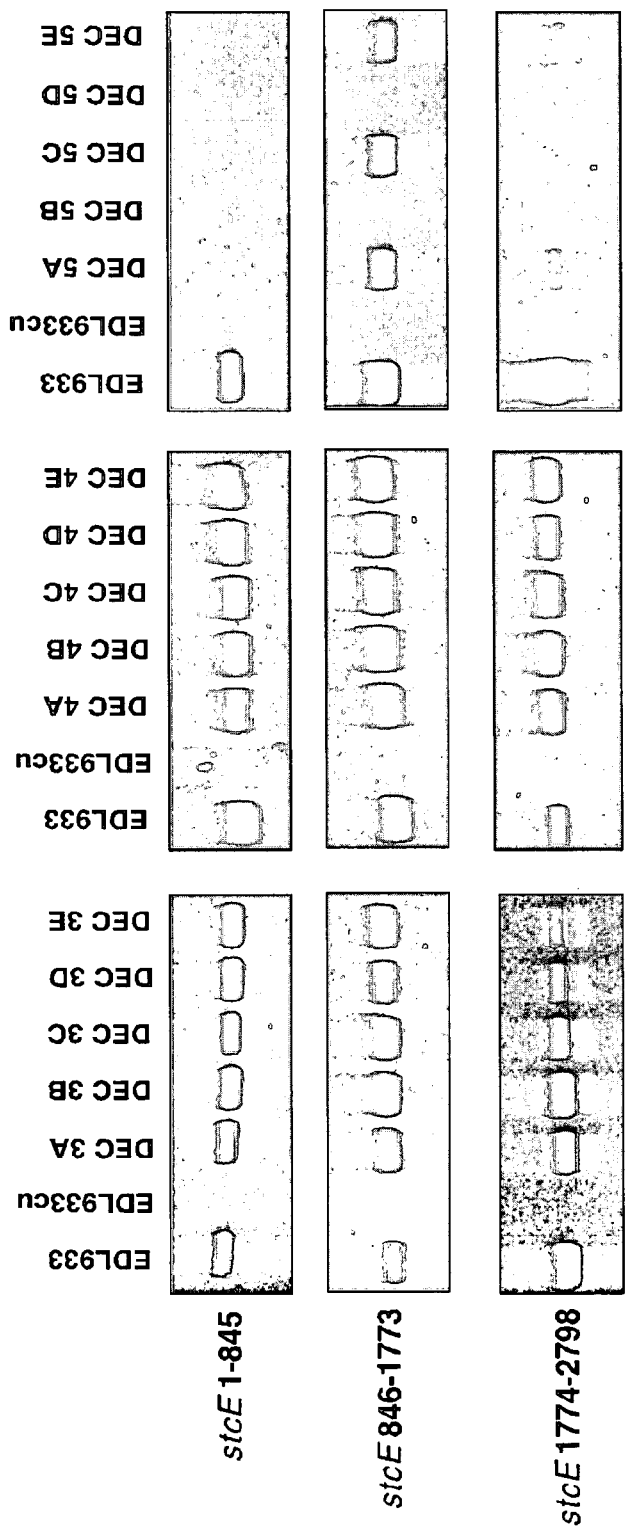
FIG. 9 shows amplification of three stcE-specific sequences from all E. Coli isolates containing the pO157, and amplification of two of the three stcE-specific sequences.

To confirm the presence of the gene among the stcE-positive groups in the DEC collection, we isolated genomic DNA from DEC3A-E, DEC4A-E, DEC5A-E, EDL933, and EDL933cu and used oligonucleotide pairs designed to amplify regions of stcE by PCR. Three primer sets were chosen to amplify stcE and its promoter from bases 1-845, 846-1773, and 1774-2798. An appropriately-sized PCR product was amplified with all three primer pairs from EDL933, DEC3A-E, and DEC4A-E (FIG. 9). Appropriately sized products were obtained with primer pairs 846-1773 and 1774-2798 for DEC5 A, C, and E, but there were no products with primer pair 1-845 from these strains. It is possible that this region of stcE, which includes the putative promoter, is sufficiently different from stcE found on pO157 to prevent priming and amplification. DEC5B and D were negative for all three reactions.

TABLE 3

Incidence of *stcE* and its product in the DEC collection

| DEC Number | Predominant Serotype | Disease Category | Number of stcE positive | Number of StcE positive |
|---|---|---|---|---|
| 1A-E | O55:H6 | EPEC | 0/5 | ND |
| 2A-E | O55:H6 | EPEC | 0/5 | ND |
| 3A | O157:H7 | EHEC | + | + |
| 3B | O157:H7 | EHEC | + | + |
| 3C | O157:H7 | EHEC | + | + |
| 3D | O157:H7 | EHEC | + | + |
| 3E | O157:H7 | EHEC | + | + |
| 4A | O157:H7 | EHEC | + | + |
| 4B | O157:H7 | EHEC | + | + |
| 4C | O157:H7 | EHEC | + | + |
| 4D | O157:H7 | EHEC | + | + |
| 4E | O157:H7 | EHEC | + | + |
| 5A | O55:H7 | EPEC | + | + |
| 5B | O55:H7 | EPEC | − | − |
| *5C* | *O55:H7* | *EPEC* | *+* | *−* |
| 5D | O55:H7 | EPEC | − | − |
| 5E | O55:H7 | EPEC | + | + |
| 6A-E | O111:H12 | EPEC | 0/5 | ND |
| 7A-E | O157:H43 | ETEC | 0/5 | 0/5 |
| 8A-E | O111:H8 | EHEC | 0/5 | ND |
| 9A-E | O26:H11 | EHEC | 0/5 | ND |
| 10A-E | O26:H11 | EHEC | 0/5 | ND |
| 11A-E | O128:H2 | EPEC | 0/5 | ND |
| 12A-E | O111:H2 | EPEC | 0/5 | ND |
| 13A-E | O128:H7 | ETEC | 0/5 | ND |
| 14A-E | O128:H21 | EPEC | 0/5 | ND |
| 15A-E | O111:H21 | EPEC | 0/5 | ND |

Using a one kb probe internal to *stcE*, colony blot analyses were performed to determine which strains in the DEC collection contained *stcE*. Strains that were positive for the gene were checked for secretion of StcE as well proteolytic activity against C1-INH. Strains in bold contained the gene and produced the protein. Strains in italics contained the gene but lacked detectable protein. All other strains in the DEC collection were negative for *stcE*.
ND = not done.

Figure 10:
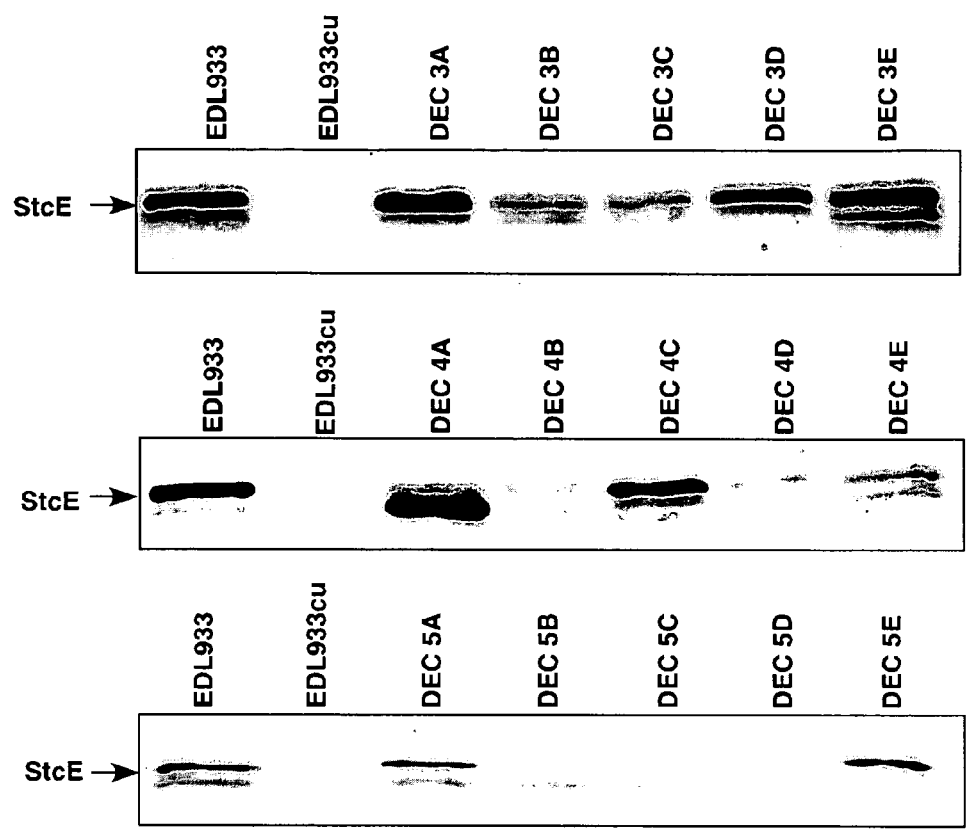
FIG. 10 shows an immunoblot of culture supernatants probed with a polyclonal antibody to StcE.
Figure 11:
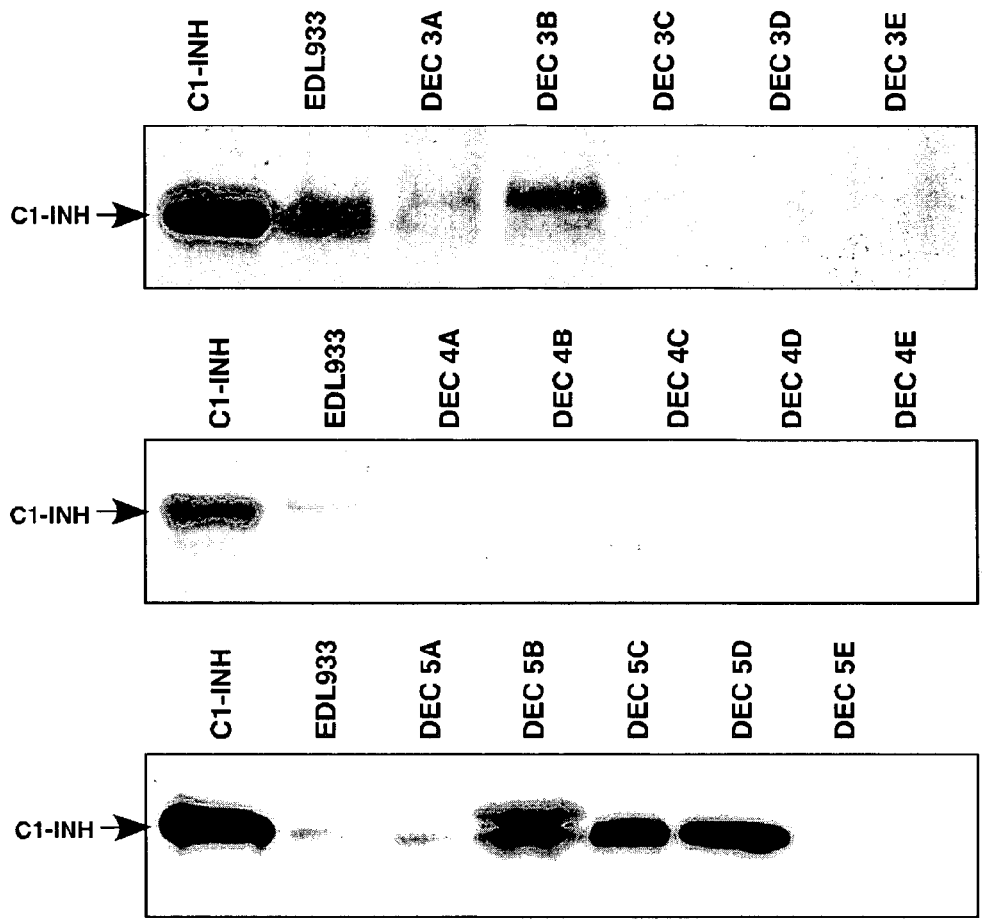
FIG. 11 shows an immunoblot of C1-INH following incubation with culture supernatants, probed with anti-C1-INH antibody.

Because previous experiments showed that StcE is released into the culture medium by EDL933 (FIG. 3), we examined whether the stcE-positive strains from the DEC collection also release StcE into the culture medium. We grew DEC3A-E, DEC4A-E, DEC5A-E, EDL933, and EDL933cu overnight in Lennox L broth at 37° C., harvested and concentrated the culture supernatants 100-fold. By immunoblot analysis we were able to detect StcE-reactive antigen in the supernatants of all stcE-positive strains and DEC5C (FIG. 10). The intensity of the reactive band varied from strain to strain and seemed to be stronger in the DEC3 group. To test if the bacterial-conditioned culture supernatants contained C1-INH proteolytic activity, we mixed purified C1-INH with the supernatants overnight and examined substrate cleavage by immunoblot. Again, all stcE-positive strains except DEC5C were able to degrade C1-INH (FIG. 11). Interestingly, DEC5B converted C1-INH from a single band to a doublet; this is unlikely to be related to StcE activity and the significance of this is unknown. It appears that DEC5C is unable to release StcE into the culture medium, although it contain stcE-like DNA. This may be due to a lack of expression of the gene or release of the protein from the cell.

II. Potentiation of C1-INH by StcE

Bacterial strains, buffers, and materials.

All chemicals were purchased from Sigma (St. Louis, Mo.) unless otherwise indicated. Buffers used were PBS (10 mM sodium phosphate, 140 mM NaCl, pH 7.4), TBS (20 mM Tris, 150 mM NaCl, pH 7.5), VBS (5 mM veronal, 145 mM NaCl, pH 7.4), VBS$^{2+}$ (VBS containing 0.15 mM CaCl$_2$ and 0.5 mM MgCl$_2$), and VBS containing 10 mM EDTA. Recombinant DNA manipulations were performed by standard methods. pTB4 was constructed by amplifying bases 207-2795 of the stcE gene from pO157 by PCR with the primers stcESac5'207 (5'-CCGAGCTC-CGGCT-GATAATAATTCAGCCATTTATTTC-3') (SEQ ID NO:20) and stcE3'Xba2795 (5'-CCTCGAGTTTATATACAACCCT-GATTG-3') (SEQ ID NO:21) and cloning the product into the SacI-XhoI sites of pET24d(+) (Novagen, Madison, Wis.). WAM2751 is *E. coli* strain BL21(DE3) (Novagen) transformed with pTB4. pTB5 was constructed in the same manner as pTB4 by amplifying the equivalent bases of the stcE E435D mutant from pTEG1, as described above. WAM2804 is *E. coli* strain BL21(DE3) transformed with pTB5. StcE'-His, lacking the StcE N-terminal signal sequence and containing a 6×His tag at the C-terminus, and StcE' E435D-His, a similar protein with a single amino acid change at residue 435 (glutamic to aspartic acid) that disrupts the catalytic activity of the protease, were purified from WAM2751 and WAM2804, respectively, as described above and dialyzed into VBS, pH 6.5. Purified C1-INH was obtained from Advanced Research Technologies (San Diego, Calif.) and both purified kallikrein and C1s from Calbiochem (San Diego, Calif.). All proteins were stored at −80° C. Monoclonal antibodies (mAbs) 3C7 and 4C3 were generous gifts from Dr. Philip A. Patston (University of Illinois at Chicago, Ill.).

Hemolytic Assays.

Sheep erythrocytes were prepared according to Mayer (42). Erythrocytes were opsonized with an anti-sheep red blood cell Ab for 10 min prior to use. Human serum (0.5%) was mixed with opsonized erythrocytes (1×10$^7$ in 50 µl) in VBS$^{2+}$ to a total volume of 200 µl for one hour at 37° C. before the addition of one ml VBS+10 mM EDTA to stop complement activity. To measure the amount of hemoglobin released by lysed cells, erythrocytes were pelleted and the O.D.$_{412}$ of the supernatant was measured in a spectrophotometer. The percent lysis was determined by subtracting the O.D.$_{412}$ in the absence of serum and dividing by the maximum possible O.D.$_{412}$ obtained by lysis of erythrocytes in water. Where indicated, increasing concentrations of StcE'-His or bovine serum albumin (BSA) were incubated with serum overnight at room temperature before the start of the assay. To determine the effect of StcE-treated C1-INH on erythrocyte lysis, increasing concentrations of StcE'-His or BSA were mixed with C1-INH (16 µg), or increasing concentrations of C1-INH were mixed with StcE'-His (one µg) or StcE' E435D-His (one µg) in a total volume of 149 µl VBS$^{2+}$ overnight at room temperature before the start of the assay. Statistical analyses were performed by the unpaired t test.

Flow Cytometry.

C1-INH (8 µg) was untreated or treated with StcE'-His (one µg) in a total volume of 149 µl VBS$^{2+}$ as described above before the addition of opsonized sheep erythrocytes and human serum deficient in complement component C5 (Quidel, San Diego, Calif.). Erythrocytes were incubated for 10 minutes at 37° C. before the addition of VBS+10 mM EDTA. Cells were washed with VBS$^{2+}$ and incubated on ice for 30 min with polyclonal goat-anti-human IgG against C1-INH (Cedarlane Laboratories). Erythrocytes were washed, incubated on ice for 30 min with FITC-conjugated rabbit-anti-goat IgG, and resuspended in VBS$^{2+}$ for analysis by flow cytometry using a fluorescence-activated cell sorter (FACSCalibur, Becton Dickinson, San Jose, Calif.). Where indicated, StcE'-His was removed from the assay mixture by adsorption to Ni-NTA agarose beads (Qiagen, Valencia, Calif.) in the presence of 50 mM imidazole prior to the addition of sheep erythrocytes. To measure StcE-treated C1-INH saturation kinetics of erythrocytes, increasing concentrations of C1-INH were mixed with StcE' E435D-His (one µg) before the addition of sheep erythrocytes (1×10$^7$) as described above in the absence of human serum and analyzed by flow cytometry.

To determine if StcE binds sheep erythrocytes, StcE'-His was labeled via its primary amines with the Alexa Fluor 488 dye as described by the manufacturer (Molecular Probes, Eugene, Oreg.). Sheep erythrocytes (5×10$^6$) were opsonized as described above, pelleted, and resuspended in 500 µl VBS$^{2+}$ before the addition of StcE'-His or Alexa-labeled StcE'-His (250 ng) for 10 minutes at 37° C. Erythrocytes were pelleted and washed with VBS$^{2+}$ before analysis by flow cytometry. To measure the point at which erythrocytes become saturated with StcE, increasing concentrations of Alexa-labeled StcE'-His were added to sheep erythrocytes (1×10$^7$) for 10 minutes at 37° C. before analysis by flow cytometry as described above.

Immunoblot Analyses.

Purified, activated C1s (1.5 µg) was untreated, treated with C1-INH (100 ng), or treated with C1-INH in the presence of StcE'-His or StcE' E435D-His (50 ng each) for one hour at 37° C. in a total volume of 30 µl VBS$^{2+}$. An equal volume of non-reducing sample buffer was then added, the samples were heated to 95-100° C. for 5 minutes, and the proteins separated on an 8% SDS-PAGE gel. Proteins were transferred to nitrocellulose and analyzed by immunoblot as described using a polyclonal goat anti-C1s Ab (Calbiochem).

In other experiments, mAb 4C3 was coupled to Protein A-sepharose beads as described (43) and used to remove trace amounts of reactive center loop (RCL)-cleaved C1-INH from the purified C1-INH preparation. Virgin C1-INH (one µg) was then incubated with or without StcE'-His (one µg) or kallikrein (2 µg) for 18 hours at room temperature before electrophoresis on an 8% reducing SDS-PAGE gel. Separated proteins were transferred to nitrocellulose and analyzed by immunoblot as described using a polyclonal anti-human C1-INH Ab (Serotec, Raleigh, N.C.), mAb 3C7, or mAb 4C3.

Cell Culture.

COS-7 cells (a gift from Dr. Donna Paulnock, University of Wisconsin, Madison, Wis.) were cultured in DMEM (Invitrogen, Carlsbad, Calif.) with 10% heat-inactivated fetal calf serum (FCS) (Mediatech, Herndon, Va.), non-essential amino acids, and penicillin/streptomycin/amphotericin B (Invitrogen). Cells were transfected with either hC1-INH/pcDNA3.1(−) or C-serp(98)/pcDNA3.1(−) (generous gifts from Dr. Alvin E. Davis, Harvard University, Cambridge, Mass.) using cationic lipids (Lipofectamine PLUS, Invitrogen). After transfection, cells were cultured in the presence of G418 (Invitrogen). Recombinant proteins were metabolically labeled with [$^{35}$S]-methionine (Amersham Biosciences, Piscataway, N.J.) for 24 hours before immunoprecipitation.

Immunoprecipitation.

Culture supernatants (100 µl) from C1-INH-transfected COS-7 cells were treated with StcE'-His (10 µg) overnight at room temperature before incubation with polyclonal goat anti-human C1-INH IgG (Cedarlane Laboratories, Ontario, Canada) and Protein A-sepharose (2 hours, room temperature). Pellets were washed three times with TBS, resuspended in sample buffer, and electrophoresed on 10% reducing SDS-PAGE gels. Gels were fixed, dried, and visualized with a phosphorimager (Typhoon 8600, Amersham Biosciences). In other experiments, C1-INH (5 µg) was untreated or treated with StcE'-His or StcE' E435D-His (5 µg each) for 10 minutes at 37° C. in 500 µl of buffer (100 mM Tris, pH 8.0) before the addition of polyclonal goat anti-human C1-INH IgG. The mixture was rotated for 30 minutes at 4° C., after which 20 µl of a Protein A-sepharose slurry was added for 2 hours. The Protein A-sepharose beads were subsequently washed three times in buffer before immunoblot analysis with an anti-StcE Ab.

Kallikrein Activity Assay.

Increasing concentrations of C1-INH were mixed with StcE'-His (250 ng) in a total volume of 100 µl assay buffer (50 mM Tris, pH 8.0, 100 mM NaCl) at room temperature overnight after which EDTA was added to 5 mM to stop the reaction. Purified kallikrein was diluted to 100 ng in 50 µl assay buffer and mixed with C1-INH for one hour at 37° C. before adding the chromogenic substrate S-2302 (Chromogenix, Milan, Italy) to each tube. Tubes were incubated at room temperature for 30 minutes before determining the absorbance of the substrate at 410 nm in a spectrophotometer. Percent kallikrein activity was determined by subtracting the $O.D._{410}$ in the absence of kallikrein and dividing by the maximum possible $O.D._{410}$ obtained by kallikrein activity in the absence of C1-INH.

Serum Resistance.

C1-INH (8 µg) was untreated or treated with StcE'-His (one µg) in a total volume of 176 µl VBS$^{2+}$ overnight at room temperature, after which human serum was added to 2%. E. coli K-12 strain C600 was grown to an $O.D._{595}$ of 0.5 in LB broth at 37° C. with aeration before being washed once and resuspended with an equivalent volume of VBS$^{2+}$. Bacteria (20 µl) were added to the reactions, incubated at 37° C. for one hour, and 10 µl aliquots were mixed with VBS+10 mM EDTA to stop complement activity. Ten-fold serial dilutions of bacteria were plated on LB agar and percent survival was determined by dividing CFUs by the total number of bacteria after one hour in the absence of serum. Statistical analysis was performed by the unpaired t test.

Inhibition of Classical Complement-Mediated Erythrocyte Lysis by StcE.

Previous research from our laboratory demonstrated that StcE, a metalloprotease secreted by E. Coli O157:H7, cleaves the serum protein C1-INH from its apparent $M_r$ of 105 kDa to produce ~60-65 kDa species. Because C1-INH is an essential regulator of the classical complement pathway, we examined the effect of StcE on the classical complement-mediated lysis of sheep erythrocytes. Human serum was mixed overnight with increasing concentrations of StcE or the control protein BSA before adding to opsonized sheep erythrocytes for one hour at 37° C. The reaction was stopped with EDTA and the amount of hemoglobin released by lysed erythrocytes into the supernatant was measured.

Figure 12:
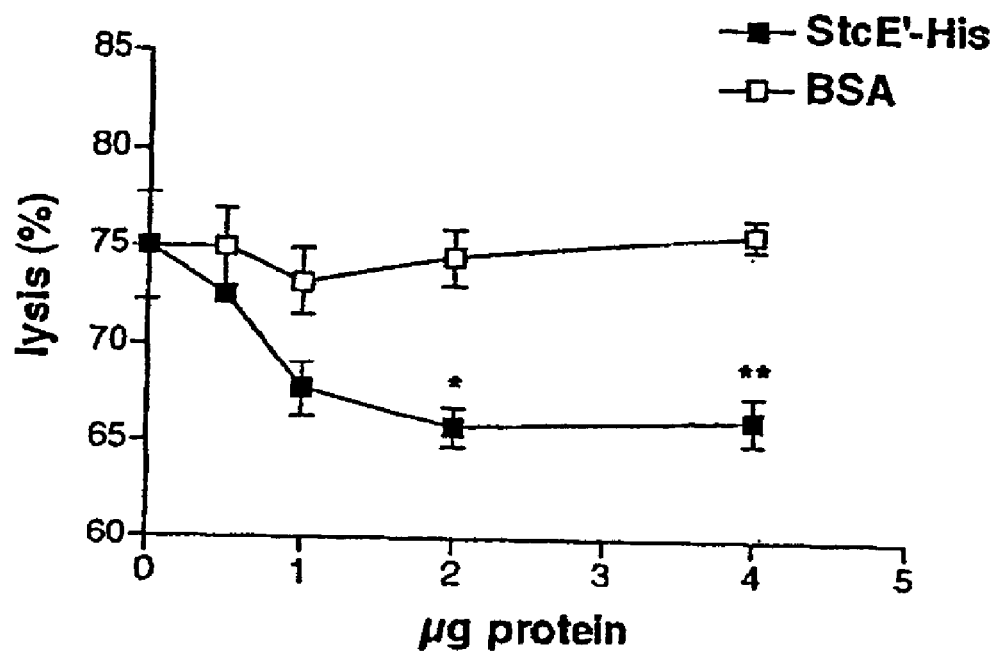
FIG. 12 shows the percent lysis of erythrocytes in classical complement-mediated erythrocyte lysis by human serum as a function of StcE (solid squares) or BSA (open squares) concentration.

Serum alone lysed 75.0% (±2.7% SEM) of erythrocytes, and BSA had no effect on the ability of serum to lyse erythrocytes (FIG. 12). At higher concentrations, StcE significantly reduced classical complement-mediated erythrocyte lysis compared to equivalent amounts of BSA (2 µg, p<0.01; 4 µg, p<0.005).

StcE Potentiates C1-INH-Mediated Inhibition of Classical Complement.

Although StcE cleaves the serum component C1-INH, the data represented in FIG. 12 does not implicate the serpin directly in StcE-mediated classical complement inhibition. To examine if StcE-treated C1-INH plays a role in this process, we mixed purified C1-INH with increasing concentrations of StcE or BSA overnight and added this mixture to human serum and opsonized sheep erythrocytes for one hour at 37° C. As before, the reaction was stopped with EDTA and the amount of hemoglobin released by lysed erythrocytes into the supernatant was measured. The addition of 0.4 IU untreated C1-INH to the assay decreased erythrocyte lysis from 82.9% (±1.1% SEM) to 33.7% (±1.8% SEM) (FIG. 13 A), demonstrating the effective role of C1-INH in the inhibition of classical complement activity. Whereas BSA-treated C1-INH was unchanged in inhibitory activity, 0.4 IU StcE-treated C1-INH reduced erythrocyte lysis to between 1.5% (±0.5% SEM) and 0.1% (±0.1% SEM) of total.

Figure 13:
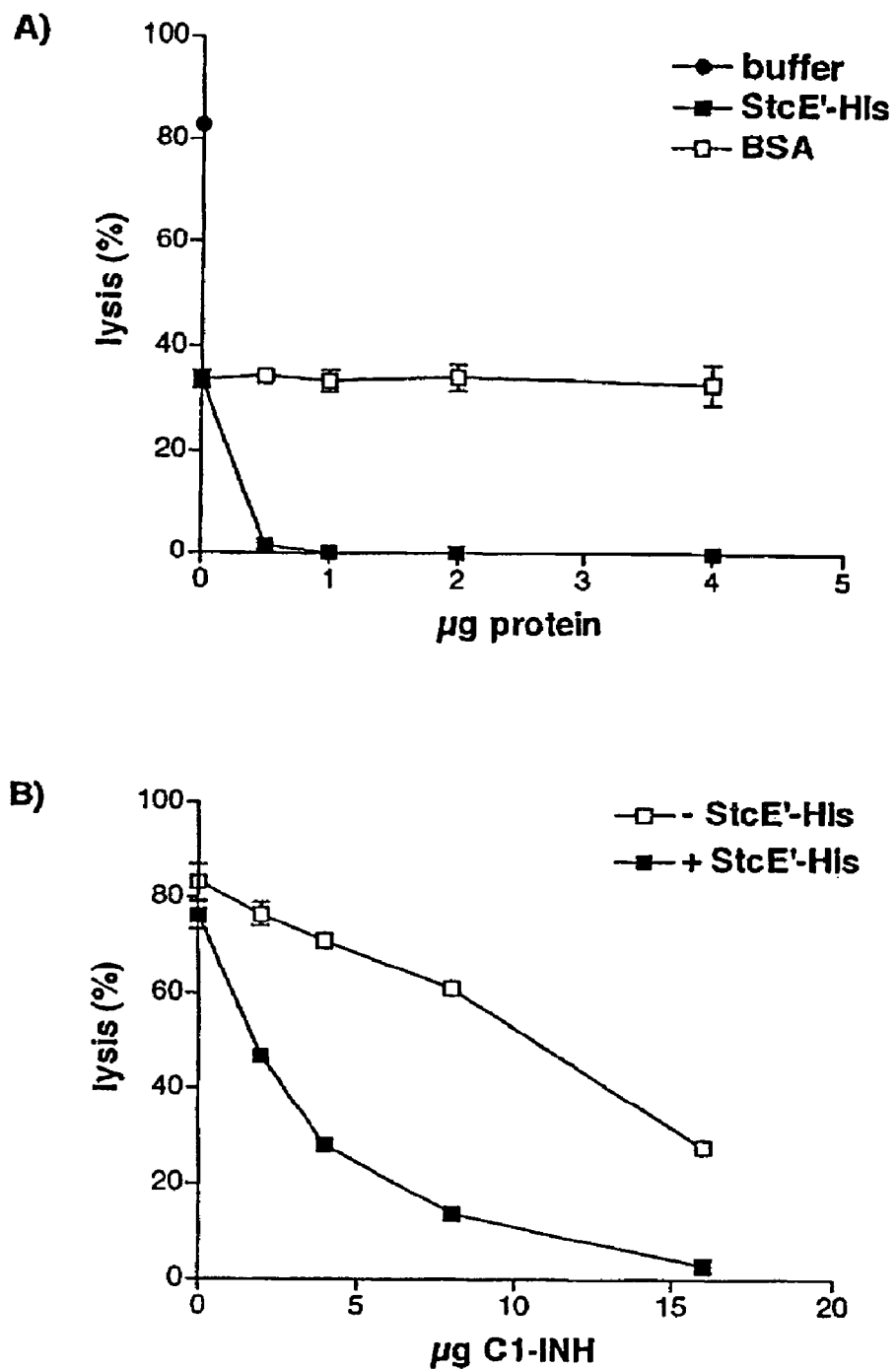
FIG. 13A shows the percent lysis of erythrocytes contacted with C1-INH treated with increasing concentrations of StcE'-His (closed squares) or BSA (open squares) prior to adding human serum. The point indicated by a circle lacked C1-INH.
FIG. 13B shows the percent lysis of erythrocytes contacted with C1-INH treated StcE'-His (closed squares) or BSA(open squares) prior to adding human as a function of C1-INH concentration.

To confirm the effect of StcE on C1-INH-mediated inhibition of erythrocyte lysis, increasing concentrations of C1-INH were untreated or treated with StcE'-His overnight prior to the addition of human serum and opsonized sheep erythrocytes. Increasing concentrations of untreated C1-INH (0.05 to 0.4 IU) resulted in a dose-dependent decrease in erythrocyte lysis, ranging from 76.5% (±2.4% SEM) to 27.5% (±1.1% SEM) (FIG. 13 B). However, in the presence of one µg StcE'-His, the same concentrations of C1-INH significantly reduced lysis below that of untreated C1-INH (ranging from 46.7% (±1.5% SEM) lysis to 2.8% (±1.3% SEM) lysis, all p values<0.0005). These results demonstrate the direct role of StcE-treated C1-INH in the decrease of classical complement-mediated erythrocyte lysis. Additional experiments confirm that StcE-treated C1-INH continues to react with its natural targets C1r and/or C1s to mediate the inhibition of classical complement, maintaining the target specificity of the serpin (data not shown).

StcE Binds Erythrocyte Surfaces.

Figure 14:
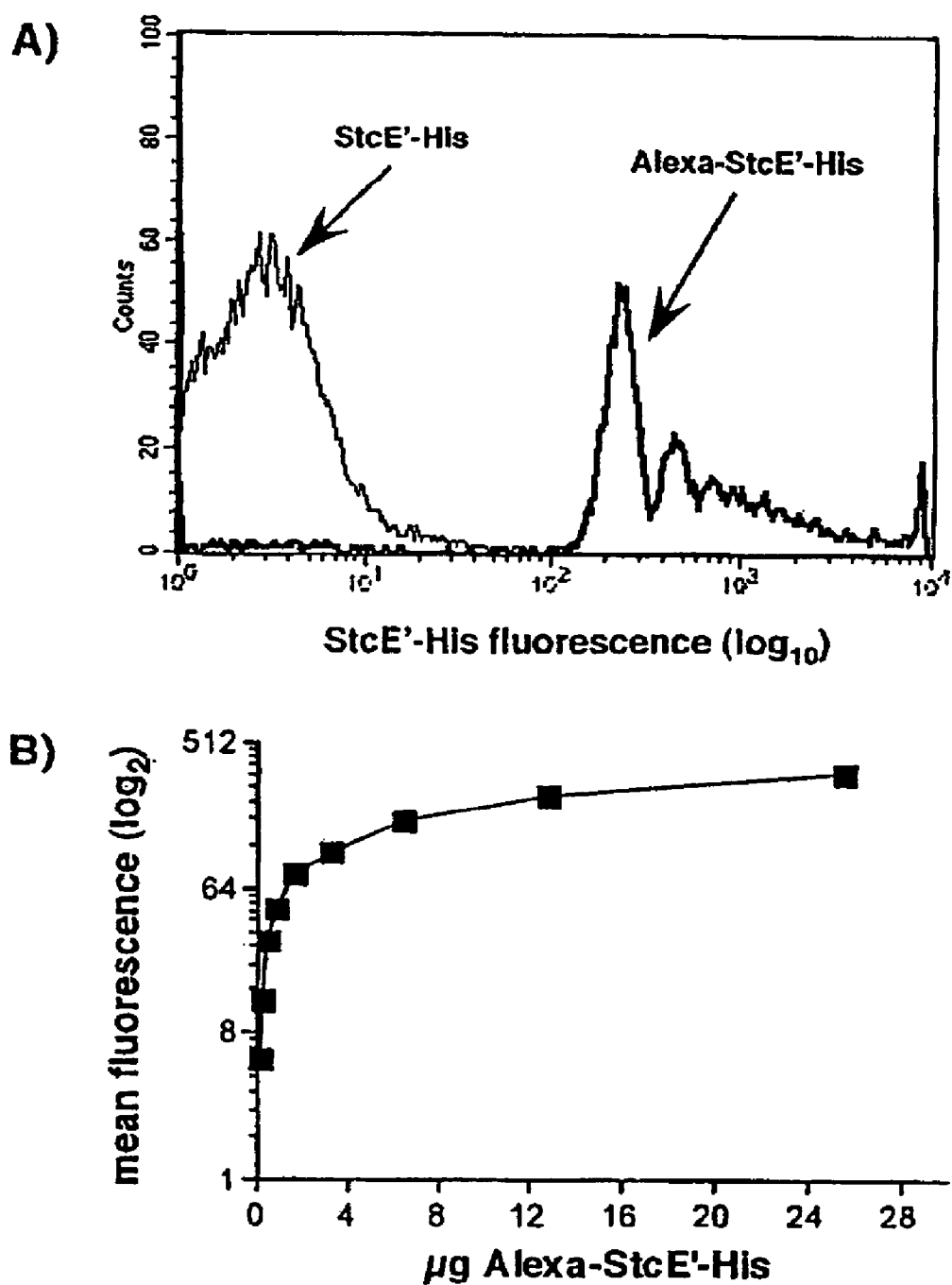
FIG. 14A shows binding of StcE'-His or Alexa-StcE'-His to erythrocytes as detected by flow cytometry.
FIG. 14B shows mean fluorescence of erythrocytes detected by flow cytometry as a function of increasing concentrations of Alexa-StcE'-His.

In order to understand how StcE might potentiate C1-INH, we asked if StcE could interact with erythrocytes, thereby acting as a binding protein for C1-INH on cell surfaces. Unlabeled StcE'-His or a form of StcE'-His fluorescently labeled via its primary amines with the Alexa Fluor 488 dye (Alexa-StcE'-His) (250 ng each) were added to opsonized sheep erythrocytes for 10 minutes at 37° C. Erythrocytes were pelleted and washed with VBS$^{2+}$ before analysis by flow cytometry. Erythrocytes treated with Alexa-labeled StcE'-His showed 80-fold greater mean fluorescence compared to cells treated with unlabeled StcE'-His (FIG. 14 A), demonstrating a direct interaction between these cells and the protease. Furthermore, we observed that StcE continues to bind sheep erythrocytes even at lower temperatures (0-4° C.), suggesting that this interaction is not mediated by an active cellular process (data not shown). To determine if the interaction between erythrocytes and StcE is specific and therefore saturable, we mixed increasing concentrations of Alexa-labeled StcE'-His with sheep erythrocytes ($1 \times 10^7$) as described above. We observed that this number of erythrocytes becomes saturated with StcE'-His at 3.2 µg of the protease in 500 µl (FIG. 14 B). Based on the calculated molecular weight of StcE'-His, at this concentration we estimate approximately $1.8 \times 10^6$ molecules of StcE are bound per erythrocyte.

StcE Localizes C1-INH to Erythrocyte Surfaces.

Figure 15:
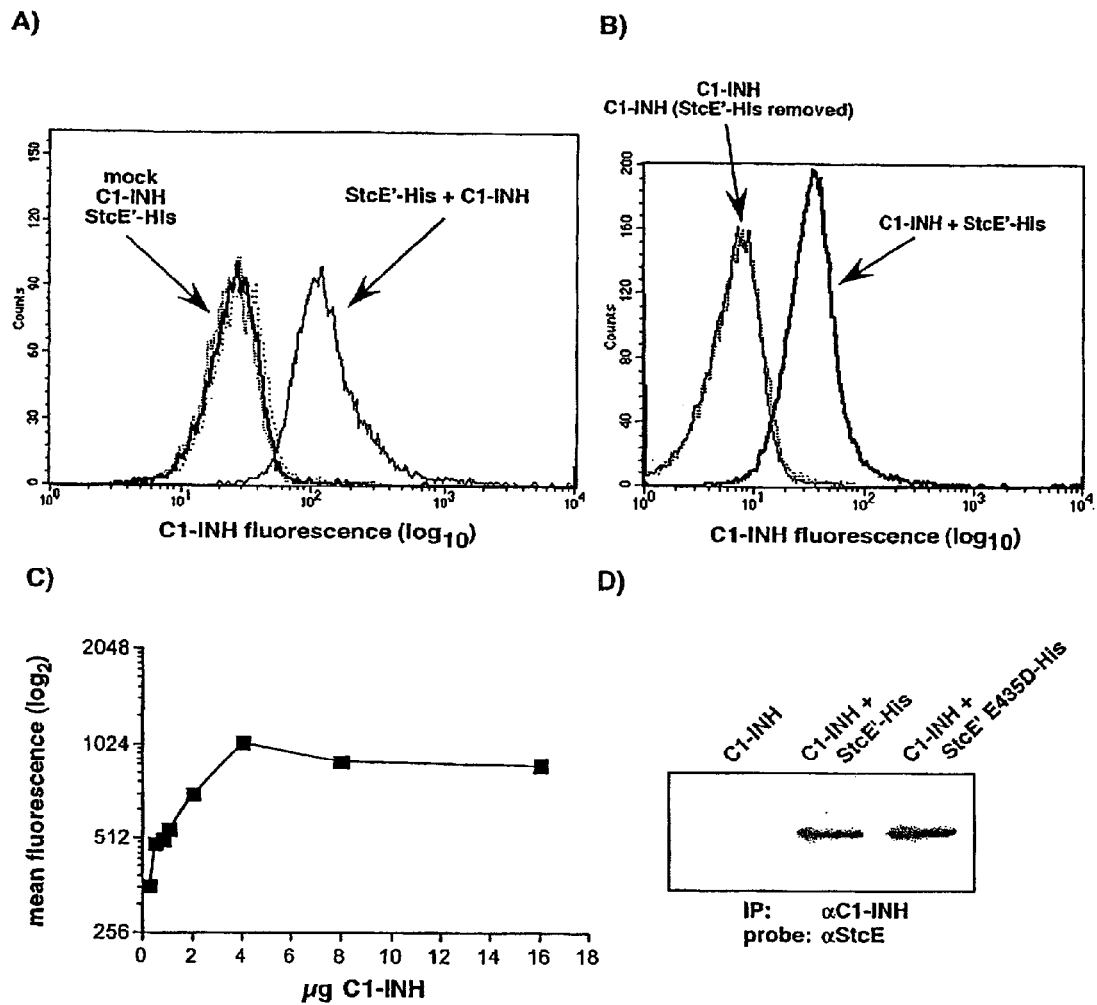
FIG. 15 B shows detection of erythrocyte binding by C1-INH treated with StcE'-His, with or without subsequent removal of StcE'-His, as detected by flow cytometry.

Based on the ability of StcE to directly bind erythrocytes, we asked if StcE could localize C1-INH to erythrocyte surfaces, thereby possibly increasing the local concentration of inhibitor at the site of potential lytic complex formation. C1-INH was untreated or treated with StcE'-His overnight before the addition of opsonized sheep erythrocytes and C5-deficient human serum (to prevent formation of the membrane attack complex and lysis of the cells) for 10 min at 37° C. Erythrocytes were washed, treated with an Ab against C1-INH and washed again prior to the addition of a FITC-conjugated secondary Ab. Deposition of C1-INH was subsequently analyzed by flow cytometry. Little to no C1-INH binding was measured on erythrocytes treated with only StcE'-His or native C1-INH compared to mock-treated cells (FIG. 15 A). Increased deposition of C1-INH was detected on erythrocytes mixed with 0.2 IU StcE-treated C1-INH, however. Similar results were observed in the absence of human serum, indicating that serum components or complement activation are not required for the localization of StcE-treated C1-INH to erythrocyte surfaces. As we observed with the interaction between StcE and sheep erythrocytes, StcE-treated C1-INH continues to bind the cells at 0-4° C. (data not shown).

The results suggest that StcE may directly mediate the binding of C1-INH to the cell surface. To test this possibility, C1-INH was incubated with or without StcE'-His overnight as described earlier, following which Ni-NTA agarose beads were added to the samples in the presence of 50 mM imidazole to specifically remove the 6xHis-tagged StcE protein from the assay. The agarose beads were pelleted and the supernatants were mixed with sheep erythrocytes and analyzed by flow cytometry as described above. In the absence of the protease, StcE-treated C1-INH no longer binds to erythrocyte surfaces (FIG. 15 B), indicating that StcE itself is required to sequester C1-INH to erythrocytes. The absence of StcE'-His from the Ni-NTA agarose-treated samples and the presence of equivalent amounts of C1-INH between Ni-NTA agarose-treated and untreated samples were confirmed by immunoblot analyses (data not shown).

To determine the level at which erythrocytes become saturated with StcE-treated C1-INH, we mixed StcE' E435D-His (a mutant form of the protein containing a single amino acid change from glutamic to aspartic acid at position 435 that is unable to cleave C1-INH with increasing concentrations of C1-INH (from 0.25-16 µg) before the addition of opsonized sheep erythrocytes as described above. We chose to use StcE' E435D-His in this experiment so as to measure the saturation of sheep erythrocytes with C1-INH without the creation of StcE-cleaved C1-INH, which might reduce the levels of the serpin bound to the cell surface, thereby increasing the amount needed to saturate the cells. We observed that, in the presence of one µg StcE' E435D-His, this number of erythrocytes becomes saturated with C1-INH at 4 µg, or 0.1 IU, of the serpin (FIG. 15 C). Based on the observed molecular weight of mature C1-INH and assuming uniform binding of the primary and secondary antibodies to their antigens, at this concentration we estimate approximately $2.25 \times 10^6$ molecules of C1-INH are bound per erythrocyte. Finally, to determine if C1-INH and StcE can interact in solution (prior to binding erythrocytes), C1-INH was mixed with either StcE'-His or StcE' E435D-His for 10 min at 37° C. before immunoprecipitating the mixture with an anti-C1-INH Ab. After separating the immunoprecipitated proteins by SDS-PAGE and transferring them to nitrocellulose, both StcE'-His and StcE' E435D-His were detected with an anti-StcE'-His Ab, demonstrating that a complex of StcE and C1-INH can be formed in solution (FIG. 15 D).

Cleavage of C1-INH by StcE is not Necessary to Protect Cells Against Complement Activity.

Figure 16:
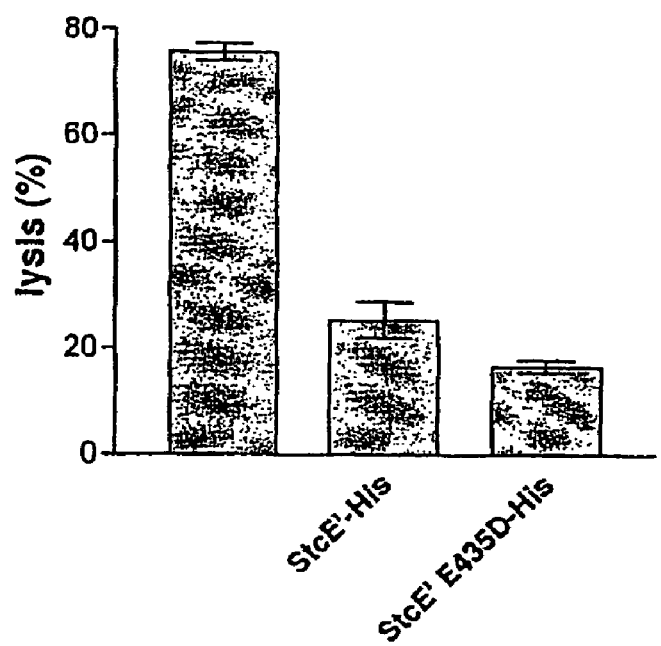
FIG. 16A shows the percent lysis of erythrocytes in classical complement-mediated erythrocyte lysis by human serum following pretreatment with C1-INH, C1-INH and StcE'-His, or C1-INH and StcE' E435D-His.
FIG. 16B shows binding of C1-INH was untreated or treated with StcE'-His or StcE' E435D-His before the addition of sheep erythrocytes as detected by flow cytometry.
Figure 16:
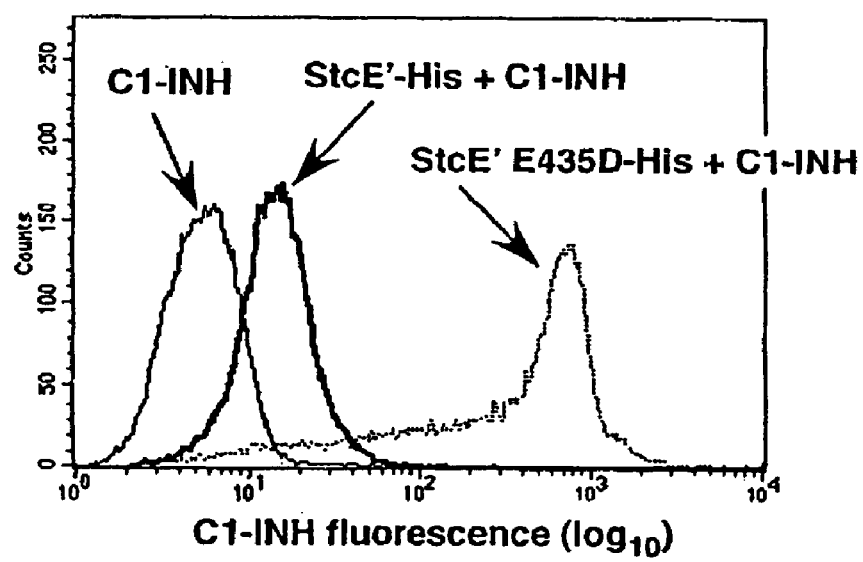

To test if the proteolysis of C1-INH by StcE is necessary to provide erythrocytes increased protection against classical complement activity over that of untreated C1-INH, we mixed C1-INH with either StcE'-His or the proteolytically inactive StcE' E435D-His. After overnight incubation, the samples were added to human serum and opsonized sheep erythrocytes for one hour at 37° C. before determining the amount of hemoglobin released into the supernatant by the lysed cells as described above. In the presence of 0.2 IU C1-INH, human serum lysed 75.8% (±1.5% SEM) of the erythrocytes, whereas StcE'-His-treated C1-INH significantly decreased erythrocyte lysis to 25.4% (±3.5% SEM, p<0.005) (FIG. 16 A). Interestingly, the cleavage of C1-INH by StcE is not required for the protection of erythrocytes from complement activity, as StcE' E435D-His-treated C1-INH was able to significantly reduce the lysis of the cells to 16.7% (±1.3% SEM, p<0.005). The difference in the extent of erythrocyte lysis between the StcE'-His-treated and the StcE' E435D-His-treated C1-INH samples was not significant (p>0.05).

To determine if the subsequent cleavage of C1-INH by StcE affects the binding of the serpin to erythrocytes, we incubated C1-INH (2 µg) with StcE'-His or StcE' E435D-His (one µg each) overnight before assessing the levels of surface-associated C1-INH by flow cytometry as described above. Indeed, the levels of C1-INH in the presence of StcE' E435D-His on erythrocyte surfaces are 22-fold higher than in the presence of StcE'-His (FIG. 16 B), suggesting that, cleaved C1-INH binds erythrocytes less efficiently than intact C1-INH. In total, the data presented in FIGS. 4 and 5 demonstrate that the increased protection of erythrocytes by StcE-treated C1-INH is dependent upon the physical presence of StcE and not the cleavage of C1-INH by the protease.

StcE is Unable to Potentiate C1-INH in the Absence of Cells.

Figure 17:
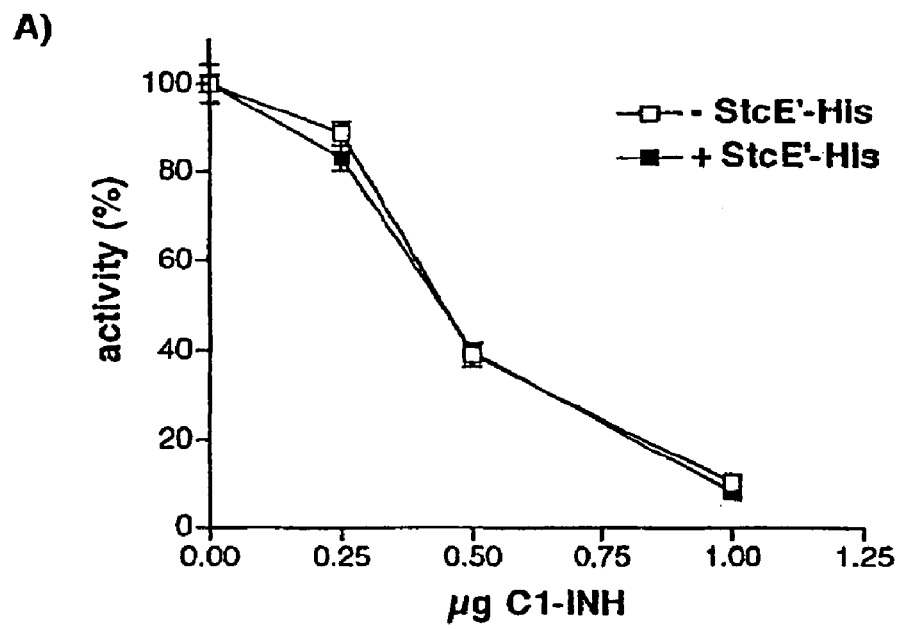
FIG. 17A shows the relative kallikrein activity in the presence of increasing concentrations of C1-INH in the presence or absence of StcE'-His.
FIG. 17B shows an immunoblot of C1s untreated or treated with C1-INH in the absence or presence of StcE'-His or StcE' E435D-His.
Figure 17:
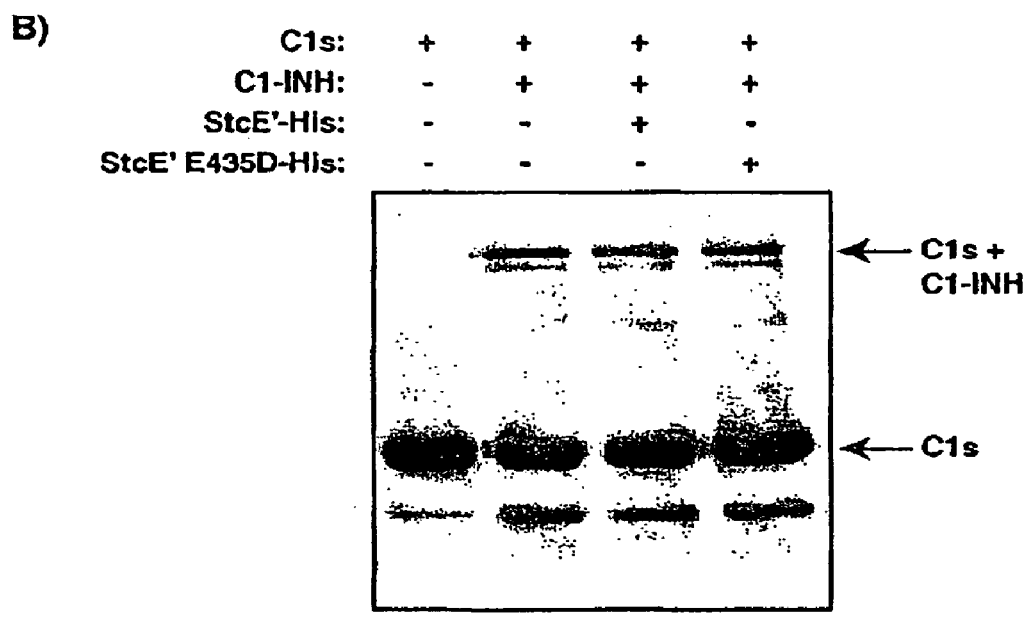

Data presented so far demonstrate the ability of StcE to localize C1-INH to erythrocytes, thereby providing increased complement-inhibiting activity at the cell surface. To determine if this potentiation can occur in solution (i.e. in the absence of cells), we measured whether StcE affects the ability of C1-INH to inhibit kallikrein, another C1-INH-regulated molecule, by monitoring the cleavage of a chromogenic substrate of kallikrein, S-2302 (H-D-Prolyl-L-phenylalanyl-L-arginine-p-nitroaniline dihydrochloride). Increasing concentrations of C1-INH were untreated or treated with StcE'-His overnight at room temperature, after which the samples were allowed to react with kallikrein for one hour at 37° C. The C1-INH/kallikrein mixtures were subsequently incubated with S-2302 for 30 min at room temperature before determining total kallikrein activity by measuring the change in absorbance of the samples in a spectrophotometer. For the purpose of this assay, kallikrein in the absence of C1-INH was considered to be 100% active. As expected, increasing concentrations of C1-INH resulted in a dose-dependent decrease in kallikrein activity, ranging from 88.8% (±2.6% SEM) to 10.3% (±1.3% SEM) activity (FIG. 17 A). The addition of StcE-treated C1-INH to the assay did not significantly alter the inactivation of kallikrein compared to untreated C1-INH.

We also examined the ability of StcE-treated C1-INH to interact with an excess of C1s in solution, thereby forming an SDS-insoluble complex. Purified, activated C1s (1.5 µg) was mixed with C1-INH (100 ng) and StcE'-His or StcE' E435D-His (50 ng each) for one hour at 37° C. before separating the proteins by non-reducing SDS-PAGE and analyzing the mixture by immunoblot with an anti-C1s Ab. The high molecular weight band in samples containing C1-INH that are absent from the sample containing C1s alone are indicative of the C1s-C1-NH interaction. If StcE were able to potentiate C1-INH in solution, an increase in the intensity of the C1s-C1-INH band would be visible; however, this does not appear to be the case (FIG. 17 B). Thus, the mechanism of StcE-mediated potentiation of C1-INH is dependent on the presence of cell surfaces upon which the protease-serpin complex can bind.

Interaction of StcE with the N-Terminus of C1-INH.

Figure 18:
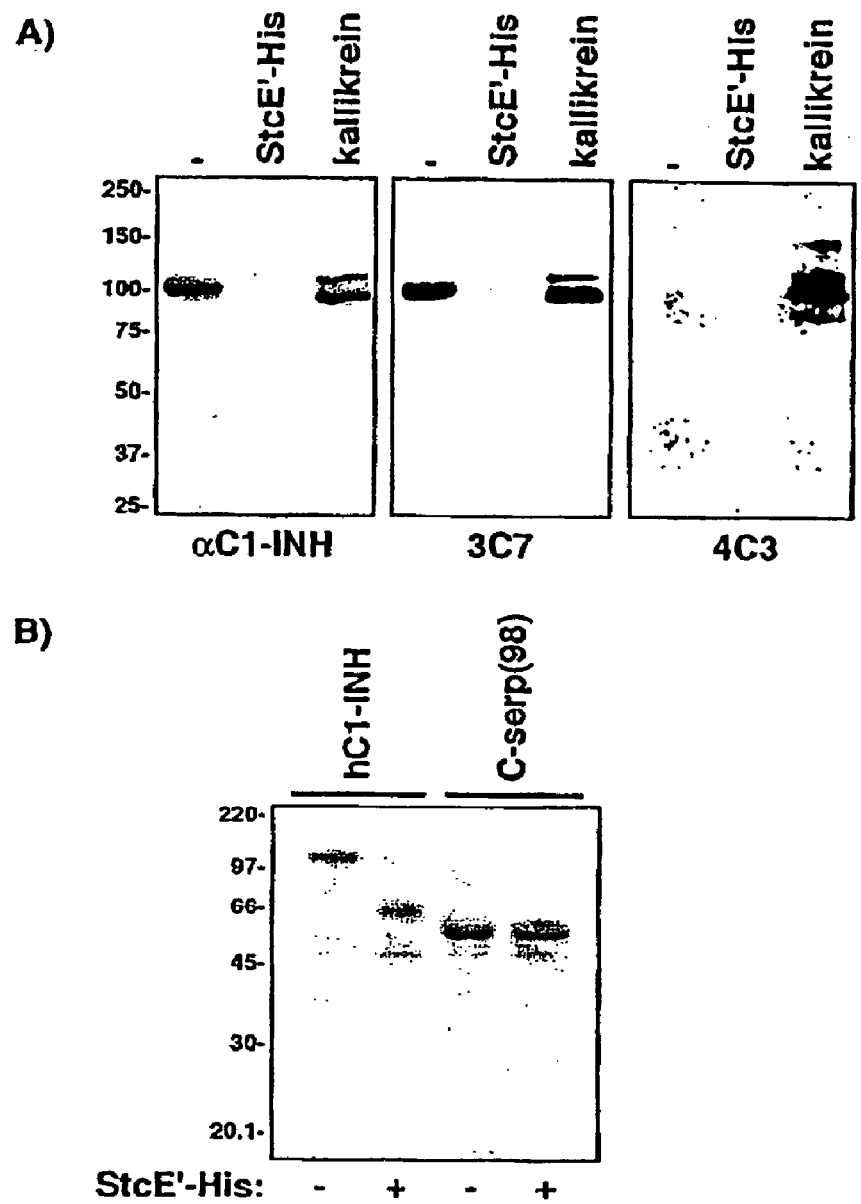
FIG. 18A shows blots of C1-INH untreated or treated with StcE'-His or kallikrein and probed with a polyclonal anti-human C1-INH Ab (left panel), mAb 3C7 (middle panel), or mAb 4C3 (right panel).

The ability of StcE to interact with C1-INH while maintaining the inhibitory activity of the molecule suggests that StcE may bind C1-INH in the heavily glycosylated N-terminal domain, leaving the serpin domain unaffected. Therefore, to further characterize the site(s) of cleavage by StcE, we examined StcE-treated C1-INH with the monoclonal antibodies 3C7 and 4C3, directed against the amino terminus of C1-INH (44) and the RCL-inserted form of C1-INH (45), respectively. As most preparations of purified C1-INH contain trace amounts of RCL-cleaved C1-INH, we removed this species of C1-INH from the mixture by immunoprecipitation with mAb 4C3 prior to analysis. Virgin C1-INH was treated with StcE or kallikrein, a serine protease inactivated by C1-INH via its interaction with and cleavage of the RCL, prior to analysis by immunoblot with a polyclonal anti-human C1-INH Ab (FIG. 18 A, left panel), 3C7 (FIG. 18 A, middle panel), or 4C3 (FIG. 18 A, right panel). As expected, analysis with 3C7 detected both virgin C1-INH and kallikrein-reacted C1-INH, but did not detect StcE-cleaved C1-INH, indicating a modification of the C1-INH N-terminus by StcE. Additionally, analysis with 4C3 detected RCL-inserted C1-INH produced upon interaction with kallikrein, but not virgin C1-INH or StcE-treated C1-INH.

To confirm that StcE interacts with the N-terminal domain of C1-INH, we examined the ability of StcE to cleave a recombinant C1-INH protein lacking this region. Coutinho et al. demonstrated that C-serp(98), a recombinant C1-INH molecule lacking the N-terminal amino acids 1-97 and containing only the serpin domain, binds its serine protease substrates identically to wild-type C1-INH and is effective in inhibiting C1 activity in hemolytic assays (31). We expressed recombinant, full-length human C1-INH (hC1-INH) and C-serp(98) in COS-7 cells and harvested the culture media after 24 hours in the presence of [$^{35}$S]-methionine. Samples were untreated or treated with StcE'-His overnight before immunoprecipitating metabolically labeled protein with polyclonal anti-human C1-INH IgG. Both hC1-INH and C-serp(98) migrated at the appropriate molecular weights on a reducing SDS-PAGE gel, however, only hC1-INH was cleaved by StcE'-His; C-serp(98) was unaffected by the protease (FIG. 18 B). These analyses further support the evidence that StcE does not inactivate C1-INH, but instead interacts with the heavily glycosylated N-terminal domain of C1-INH, leaving the serpin domain available for interaction with C1-INH targets.

Increased Bacterial Serum Resistance in the Presence of StcE-Treated C1-INH.

Figure 19:
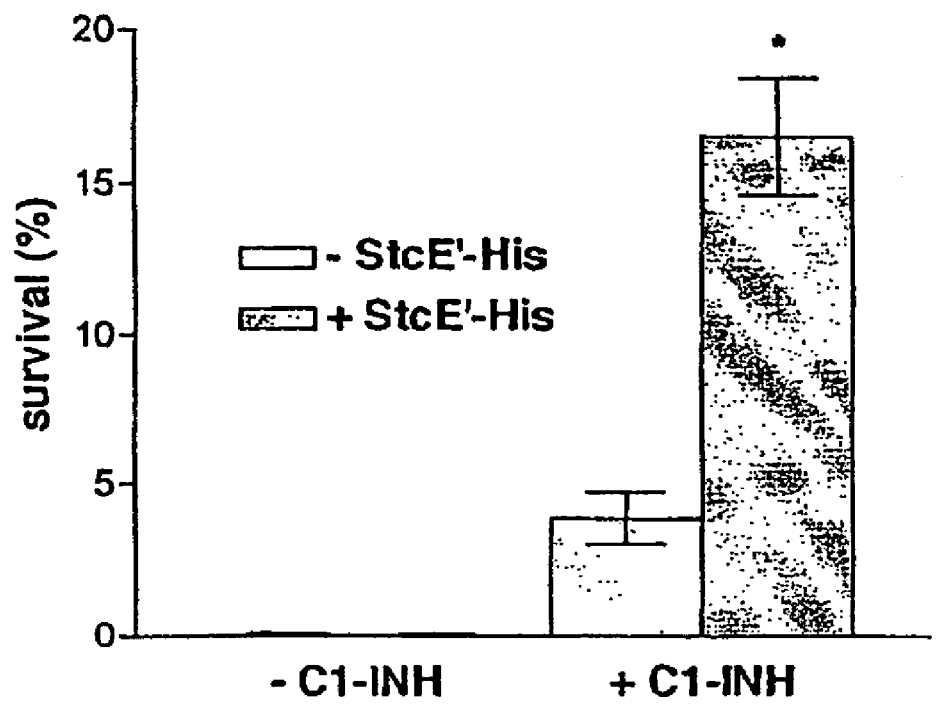
FIG. 19 shows the percent survival of serum sensitive bacteria in the presence of serum and of C1-INH, StcE'-His, C1-INH and StcE'-His, or no additional protein.

StcE is secreted by *E. coli* O157:H7, a human pathogen that may come in contact with blood or blood products during the course of an infection. Based on its ability to enhance C1-INH-mediated inhibition of classical complement, we examined if StcE could provide serum resistance to *E. coli*. As *E. Coli* O157:H7 is naturally serum resistant and contains a variety of factors that could contribute to its protection from complement (1), we chose to assess the role of StcE-treated C1-INH in the survival of a serum-sensitive strain of *E. coli*. *E. coli* K-12 strain C600 was grown to mid-log phase, pelleted, and resuspended in an equivalent amount of VBS$^{2+}$ before the addition of human serum and 0.2 IU C1-INH or StcE-treated C1-INH. Bacteria were incubated at 37° C. for one hour, serially diluted and plated onto LB agar to determine the numbers of surviving CFUs. In the presence of human serum alone, 0.07% (±0.06% SEM) of bacteria survived, demonstrating the exquisite serum sensitivity of *E. coli* strain C600 (FIG. 19). The addition of StcE'-His to bacteria at the beginning of the assay had no significant effect on survival (0.04% survival, ±0.03% SEM). As expected, the addition of untreated C1-INH increased survival of bacteria to 3.9% (±0.9% SEM). The addition of StcE-treated C1-INH to the assay, however, caused a significant increase in bacterial survival over untreated C1-INH (16.5% survival, ±1.9% SEM; p<0.005), indicating a contribution to complement resistance by StcE.

III. Further Characterization of StcE and its Role in Pedestal Formation Construction of StcE Knockout and Restored Strains Construction of EDL933 ΔStcE::cm (WAM 2815).

Construction of EDL933 ΔstcE::cm (WAM 2815). A deletion mutant of stcE from EDL933 was constructed by the linear recombination (λ Red) method of Datsenko and Wanner (77). Briefly, the oligonucleotides 5' 707 (5'-ATG AAATTAAAGTATCTGTCATGTACGATC-CTTGCCCCTTGTGTAGGCTGGAGC TGCTTC-3') (SEQ ID NO:22) and 3' 708 (5'-TAATTTATATACAACCCTCATT GACCTAGGTTTACTGAAGCATAT-GAATATCCTCCTTAG-3') (SEQ ID NO:23) were used to amplify by PCR the chloramphenicol resistance cassette from the non-polar (in frame, with added ribosome binding site) plasmid template pKD3. The resulting product was then transformed by electroporation into WAM2806 (EDL933 carrying pKD46, grown at 30° C. in the presence of 10 mM arabinose). Transformants cured of pKD46 and lacking the stcE coding sequence were selected by growth on LB agar containing chlormaphenicol (20 µg/ml) at 42° C. and were confirmed by PCR. More than 95% of the coding sequence of stcE was deleted, leaving behind the 5' and 3' ends of the gene encoded by the oligonucleotides.

A StcE complemented strain having the stcE gene restored was created using a Tn7 transposase system similar to that described by DeLoney et al. (77). The stcE gene was PCR amplified using primers 5'1135 (5'-AAG GGC CCC TCT GAG GTG TCT GTT AAA CCC GTG G-3') (SEQ ID NO:24) and 5'1136 (5'-AAA AA TGG CCA CGA AGT GGC CGC ACC GTC TCA GG-3') (SEQ ID NO:25). The gene was put into the ApaI-MscI sites of pEVS 107 and electroporated into the mating strain WAM1301, E. coli 517λpir, creating a strain called WAM2980. The strains WAM2980, WAM2815, and WAM2871 (E. coli carrying the helper plasmid pUX-BF13 which has the Tn7 transposase genes tnsABCDE), were mated. This resulted in strain WAM2997, which is the WAM2815 ΔstcE::cm strain that carries a single copy of stcE on the chromosome and has restored StcE expression.

Production of an Untagged, Purified StcE Protein

Recombinant, untagged StcE protein was created using the IMPACT protein expression system from NEB (New England Biolabs, Beverly, Mass.). Briefly, the stcE gene was amplified by PCR using Deep Vent polymerase (NEB) and purified pO157 plasmid DNA as a template. The gene was then inserted into pTYB1 (NEB) at the NheI and SapI restriction sites of the multiple cloning site, creating pTEG11. This plasmid created a fusion gene of stcE with sequences encoding a chitin binding domain and an intein protease. The plasmid was moved into the expression strain ER2566 (NEB). The chitin-binding domain of the expressed protein allowed affinity purification on a chitin-sepharose column, while the intein protease allows the target protein to be released from the two fusion domains. The result was a StcE protein that had three extra residues (Met-Ala-Ser) at its N-terminus, but is otherwise identical to StcE secreted from strains carrying the pO157 plasmid. This same protocol can be used to express a proteolytically inactive form of rStcE called E435D, which has a mutation of a glutamate to aspartate residue at the zinc metalloprotease.

Tissue Culture of HEp-2 Cells.

HEp-2 cells, which are derived from a contaminant of the human cervical epithelial cell line HeLa, were maintained in Eagle's modified medium (Mediatech Herndon, Va.) supplemented with 10% FBS (Atlanta Biologicals, Norcross, Ga.), 10 mM sodium pyruvate, penicillin, streptomycin, and amphotericin B. Cells were passed after achieving confluence by lifting with 0.25% Trypsin-EDTA (Mediatech) and diluting to 1:5 or 1:10

Microscopic Analysis of Pedestal Formation

Evaluation of pedestal formation was adapted from Knutton et al. Infection & Immunity 57: 1290 (1989) and *Methods in Enzymology* 253: 324.

Bacterial strains were inoculated from a single colony on an LB plate into Lennox broth (2 ml) at 37° C., without shaking and grown to stationary phase (12-18 hours). The media used for infection was Dubelco's modified MEM medium supplemented as above. The overnight bacterial culture was diluted 1:25 in this media, for an average inoculation of $8 \times 10^6$ CFU/ml. HEp-2 cells from a confluent dish were diluted 1:5 or 1:10 and grown in 4 or 8 well slides (Nalge Nunc International, Naperville, Ill.) for 24 to 48 hours (50-80% confluent). Cells were washed three times in PBS to remove any residual antibiotics in the media. Then the DMEM-bacterial mixture was placed on the cells, 0.5 ml for 4 well slide, 0.25 ml for 8 well slide, and incubated at 37° C. for 6-7 hours, with or without simultaneous addition of recombinant StcE (2 μg). Media was removed at midpoint of incubation and replaced with fresh media and no additional bacteria.

After infection, cells were washed thoroughly (5-6 times) with PBS and fixed in paraformaldhehyde (3% for 10 minutes). Cells were washed with PBS (three times for two to three minutes) after fixation. A 15 minute blocking step with antibody dilution solution (2% BSA, 0.1% Triton X-100 in PBS) was used to inhibit non-specific staining. Bacteria were stained with a monoclonal antibody recognizing the O157 antigen (US Biologicals, Swampscott, Mass.) for 30 minutes in a 1:200 dilution. After washing in PBS, cells were stained with the secondary antibody solution containing goat anti-rabbit conjugated to Alexa488, 1:1000 (Molecular Probes, Netherlands), and Phalloidin conjugated to Alexa594 1:400 (Molecular Probes).

Samples were analyzed using a Zeiss (Carl Zeiss Micro-Imaging Inc., Thornwood, N.Y.) fluorescent microscope using a 40× plan apochromat NA 1.3 objective. Images were acquired with a Axiocam monochrome CCD camera and Openlab software (Improvision, Lexington, Mass.). Random fields from blinded sample wells were selected out-of-focus on the phalloidin channel such that no actin pedestals were discernible that might bias selection. Number of foci that had formed pedestals were counted in each field after 10 (8 well slides) or 20 (4 well slides) fields were imaged of each sample. Foci were defined as either a single bacterium or a cluster of bacteria separated from other foci by more than the length of a bacterium.

Figure 20:
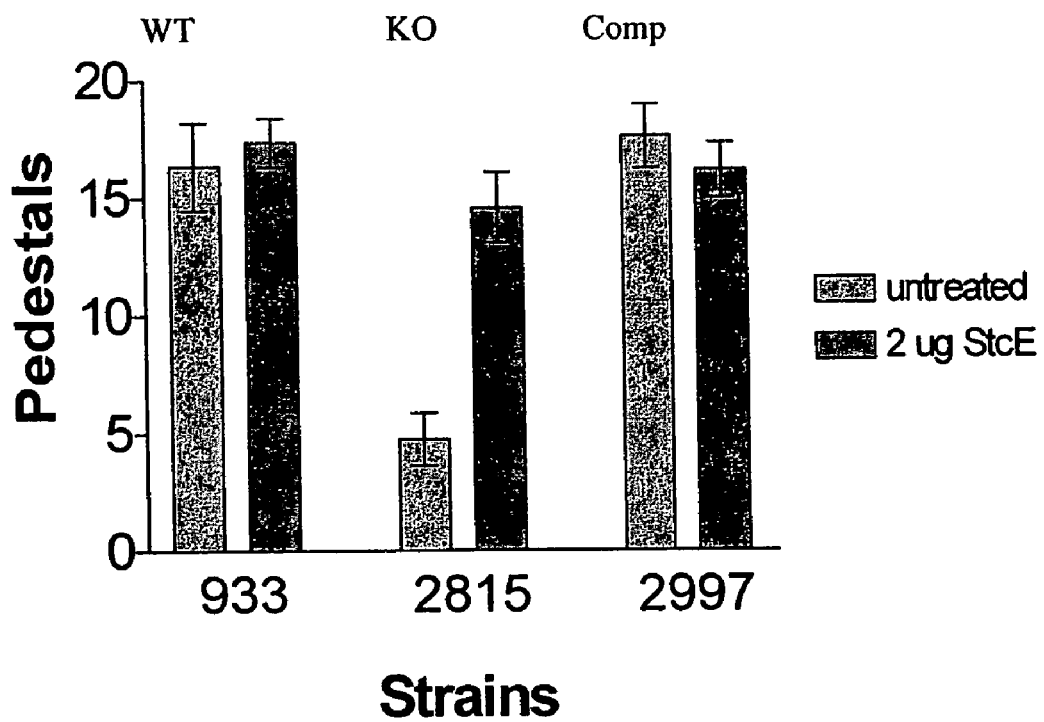
FIG. 20 compares the number of pedestals per field formed for wild type, StcE knockout, and complemented E. coli O157:H7 strains on HEp-2 cells in the presence or absence of exogenous StcE.

The results indicate that the StcE knockout mutant has a lower capacity for forming pedestals than the wild type or the complemented strain, but the ability is restored by supplementation with exogenous StcE (FIG. 20).

StcE Reduces Viscosity of Saliva and Solubilizes Mucus

Because StcE has the capacity to cleave a heavily glycosylated, mucin-like region of C1-INH, studies were undertaken to determine whether StcE was capable of cleaving other substrates. Human saliva and sputum, which are good sources of mucins and glycoproteins, were evaluated as follows.

Figure 21:
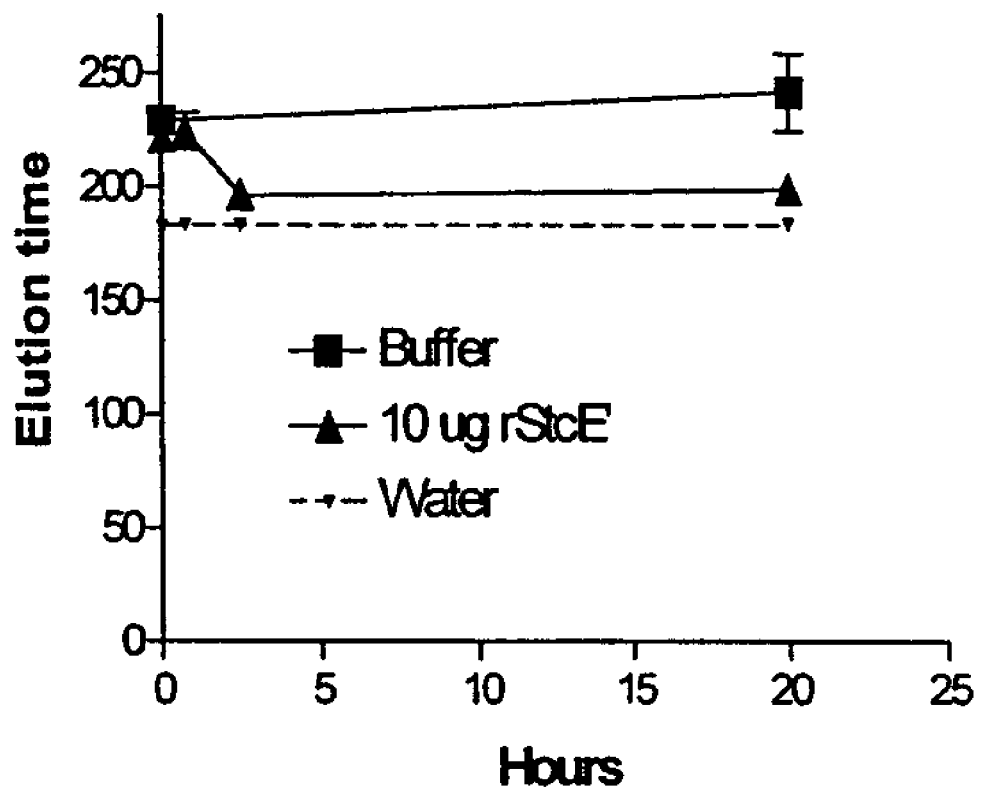
FIG. 21 compares the viscosity of saliva before (zero hour) and after incubation in buffer (squares) or in StcE (triangles) relative to water (dashed line) as measured by elution time as a function of incubation time.

Whole human saliva was collected and split into 10 ml samples. The viscosity of the samples was measured before and after a 3 hour treatment with rStcE or buffer. Both the treatment and measurements took place at 37° C. Relative viscosity was measured in a Cannon-Fenske Routine Viscometer (range: 0.5 to 4 cP) (Cannon Instrument Company, State College, Pa.), and elution time was measured, with less viscous solutions that travel through the viscometer relatively quickly having shorter elution times than more viscous solutions. Treatment with StcE was found to reduce the viscosity of saliva by about 66% (FIG. 21).

Mucus from a person with a cold was expectorated into a sample tube. Aliquots (1 ml) were transferred into a 10 ml glass tube using a blue tip (made for a p-1000 pipette) with the tip cut off, creating a wider bore. One tube was untreated and to the other StcE (40 μg) was added. Both were vortexed briefly (setting 4 of 9) and incubated 3 days at room temperature. The samples were then vortexed briefly and tested for ability to be pipetted by a blue tip with a 1000 μl pipet and for ability to flow freely in the 10 ml sample tube. The StcE treated sample was free-flowing and easily pipetted while the untreated sample was still thick and viscous, and would get stuck in a blue tip.

Identification of Saliva Proteins Cleaved by StcE

Figure 22:
FIG. 22 shows human salival proteins separated by SDS-PAGE and stained with Coomassie.
Figure 23:
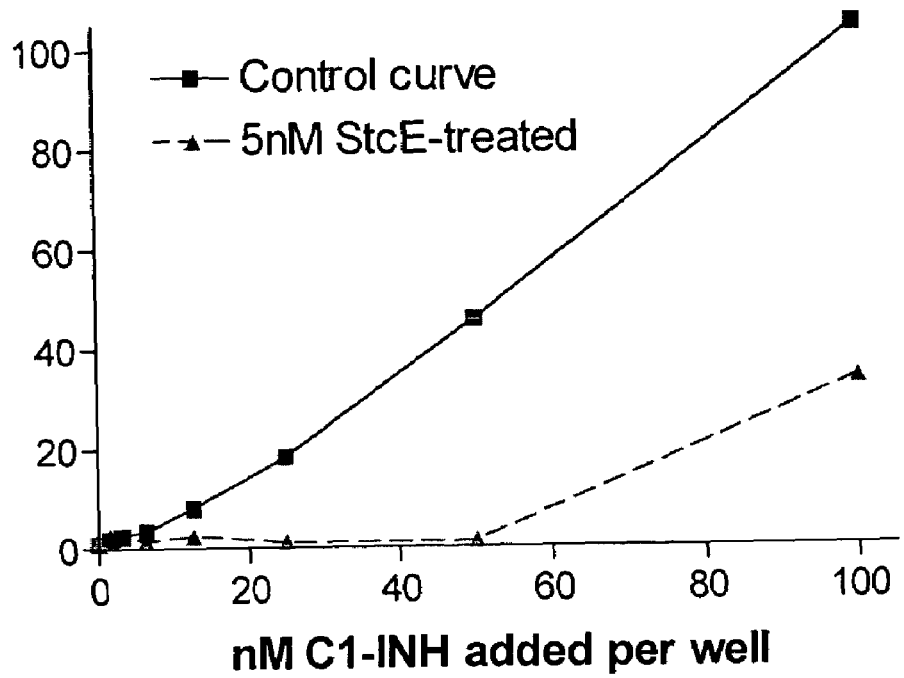
FIG. 23 is a graph showing the concentration of detectable C1-INH in a well as a function of the amount of C1-INH added to the well for samples treated with StcE in the presence (squares) or absence (triangles) of EDTA.

Whole human saliva was collected and treated with rStcE (1 μg) or untreated for one hour at room temperature. Proteins were separated by SDS-PAGE (8% acrylamide) and stained with Coomassie R-250. With reference to FIG. 22, lane 1 includes rStcE-His; lane 2 includes untreated saliva; and lane 3 contains saliva treated with rStcE-His. Proteins of interest (indicated with arrows) were excised from the gel, digested with trypsin and analyzed by MADLI-TOF mass spectrometry. Peptide masses were compared to the Protein-Prospector database (University of California at San Francisco) for identification. The proteins were found to be MUC7 and gp-340/DBMT1.

ELISA for C1-INH Cleavage by StcE

An enzyme-linked immunosorbant assay (ELISA) was used to test for StcE protease activity toward C1-INH in a 96 well format. The primary antibody 3C7 (gift of Phil Patston, University of Illinois at Chicago) binds only uncut C1-INH, but does not bind to either fragment produced by StcE cleavage. The antibody is thought to bind somewhere in the N-terminal 100 amino acids of C1-INH, but the binding site is presumed to be destroyed by StcE cleavage.

First, 0.1 to 10 mmol C1-INH was mixed with 0-5 mmol StcE in a total volume of 100 µl PBS (phosphate buffered saline) in a round bottom microtitre plate (Sarstedt). After 1 hour at 37° C., an EDTA solution (10 mM in PBS, 50 µl) was added to stop the reaction. The reaction mixtures were transferred to an ELISA plate (Dynatech flatbottom Immulon plates, Alexandria, Va.) and held at room temperature (RT) for 2 hours to allow binding of proteins to the plate. The wells were emptied, bovine serum albumin (BSA, 1% in PBS, 100 µl) was added to each well and incubated for 30 minutes to block non-specific binding. The wells were then washed three times for one minute each with PBST (PBS with 0.05% Tween-20, 200 µl). The primary antibody was diluted 1:1500 in blocking solution and 100 µl was added to each well and incubated at RT for 60 minutes. Wells were again washed, and then the secondary antibody (goat anti-mouse conjugated to horseradish peroxidase, BioRad, Hercules, Calif.) was diluted 1:3000 in blocking solution and 100 µl added to each well and incubated at RT for 30 minutes. After a final wash, substrate solution (100 µl TMB, BioRad) was added to each well. After a ten-minute incubation while rocking at RT, stop solution was added (100 µl 1N sulfuric acid). Absorbance at 450 nm was read and used to calculate the C1-INH remaining in the wells. C1-INH remaining was plotted as a function of the amount of C1-INH added to the well (FIG. 24). The results indicate that the amount of detectable (i.e., intact) C1-INH is reduced in the presence of StcE.

This method provides a means of detecting the presence of StcE activity in a test sample. In addition, the method provides a means for evaluating the ability of a test substance to inhibit cleavage of C1-INH in the presence of StcE.

Proposed ELISA for Detection of StcE Protein in Mixtures or Clinical Samples

StcE is expressed in enterohemorrhagic *E. coli* infections, although it is presently known whether the protein is expressed early or late in the course of colonization and infection. If it expressed early, detection of StcE could be a valuable tool for early detection of infection.

A clinical sample such as a fecal filtrate or bacterial supernatant is adsorbed onto an untreated ELISA plate. After a block and wash step, the wells are probed with an antibody against the StcE protein. Following another wash, a secondary antibody (e.g., anti-mouse conjugated to horseradish peroxidase, BioRad) is added to the wells. After a final wash, a substrate solution, such as TMB substrate (BioRad), is cleaved by the horseradish peroxidase, and its product is detected, indicating the presence of StcE.

Alternatively, a sandwich ELISA method is employed in which the ELISA plate is be pre-adsorbed with antibodies to StcE. The subsequent steps are the same as those outlined in the preceding method.

Model of StcE Role in EHEC Colonization of Host Cells

We propose a model in which the StcE-mediated increase in pedestal formation is due to cleavage of proteins from the glycocalyx and/or cell surface, allowing a closer interaction of bacterium and host cell. Cleavage of these proteins may also lead to decreased adherence of normal flora, which would compete with EHEC for space and resources. Addition of StcE to cell extracts prepared from uninfected HEp-2 cells showed that StcE changed the banding pattern of proteins separated via SDS-PAGE. This data supports the model that host cell proteins are being cleaved or modified in a way that is favorable to intimate adherence by EHEC. It is expected that most of these proteins are cell-surface proteins, and identification of these potential substrates is underway.

StcE Reduces Viscosity of Cystic Fibrosis Sputum

Expectorated sputum samples collected for routine bacterial culture from Cystic Fibrosis (CF) patients were obtained (IRB approval granted). Specimens were divided into equal portions in 1.5 ml microcentrifuge tubes and treated with StcE (14 µg) in PBS, E435D StcE in PBS, or PBS alone. The samples were incubated at 37° C. and periodically inverted to observe viscosity. In 78% of CF sputum samples (n=18) treated with StcE, reduced viscosity was observed. In contrast, no change in viscosity was observed in sputum samples treated with E435D StcE or PBS. Reduced viscosity was generally observed 20-30 minutes post-treatment, and often the effect was enhanced by longer incubation, such as for 1-2 hours.

StcE Degrades gp340 and MUC7 in Cystic Fibrosis Sputum

Expectorated sputum samples collected for routine bacterial culture from CF patients were obtained (IRB approval granted). Samples were vortexed for 60 seconds in PBS to extract mucous material and centrifuged. Supernatants were treated with PBS, StcE, or E435D StcE at 37° C. for 60 minutes, then boiled in SDS-PAGE sample buffer and separated on 1% agarose gels in TAE+0.1% SDS. Gels were blotted to nitrocellulose membranes by capillary transfer and the proteins were probed with antibodies or antisera to gp340 (1:5000, mouse anti-human, MBL, Woburn, Mass.), MUC7 (1:1000, rabbit anti-human, gift of J. G. M. Bolscher), MUC5AC (1:500, mouse anti-human, U.S. Biological, Swampscott, Mass.), MUC5B (mouse anti-human, 1:500, U.S. Biological), and MUC2 (rabbit anti-human, 1:500, Biomeda, Foster City, Calif.), followed by secondary antibodies conjugated to horseradish peroxidase.

Immunoblots of protein extracts from cystic fibrosis sputum samples demonstrated that a band identified via monoclonal antibody against gp340 showed degradation following incubation with StcE. No degradation of gp340 was observed in samples incubated with buffer or E435D StcE. Antisera against MUC7 showed a breakdown of MUC7 following incubation with StcE, in one sample. No degradation of MUC7 was observed in samples incubated with buffer or E435D StcE. Antibodies against mucins commonly found in CF sputum secretions, including MUC5B, MUC5AC, and MUC2, were used to probe immunoblots of the samples. None of the bands recognized by the mucin antibodies was altered by StcE treatment.

REFERENCES

1. Perna, N. T., Plunkett III, G., Burland, V., Mau, B., Glasner, J. D., Rose, D. J., Kirkpatrick, H. A., Postal, G., Hackett, J., Klink, S., Boutin, A., Shao, Y., Miller, L., Grotbeck, E. J., Davis, N. W., Lim, A., Dimalanta, E. T., Potamousis, K. D., Apodaca, J., Anantharaman, T. S., Lin, J., Yen, G., Schwartz, D. C., Welch, R. A. & Blattner, F. R. (2001) *Nature* 409, 529-533.

2. Waytes, A. T., Rosen, F. S. & Frank, M. M. (1996) *N. Engl. J. Med.* 334, 1630-1634.

3. Caliezi, C., W. A. Wuillemin, S. Zeerleder, M. Redondo, B. Eisele, and C. E. Hack. (2000) C1-Esterase inhibitor: an anti-inflammatory agent and its potential use in the treatment of diseases other than hereditary angioedema. *Pharmacol Rev* 52:91-112.

4. Poulle, M., Burnouf-Radosevich, M. & Burnouf, T. (1994) *Blood Coagulation & Fibrinolysis* 5, 543-9.

5. Kuno, K., Terashima, Y. & Matsushima, K. (1999) *Journal of Biological Chemistry* 274, 18821-6.

6. Gadek, J. E., Hosea, S. W., Gelfand, J. A., Santaella, M., Wickerhauser, M., Triantaphyllopoulos, D. C. & Frank, M. M. (1980) *N. Engl. J. Med.* 302, 542-546.

7. Lorenzo, V. D. & Timmis, K. N. (1994) in Bacterial Pathogenesis, eds. Clark, V. L. & Bavoil, P. M. (Academic Press, San Diego), Vol. 235, pp. 386-405.

8. O'Farrell, P. H. (1975) *J Biol Chem* 250, 4007-21.

9. Bauer, M. E. & Welch, R. A. (1996) *Infect. Immun.* 64, 167-175.

10. Burland, V., Shao, Y., Perna, N. T., Plunkett, G., Sofia, H. J. & Blattner, F. R. (1998) *Nucleic Acids Research* 26, 4196-4204.

11. Roesch, P. L. & Blomfield, I. C. (1998) *Molecular Microbiology* 27, 751-61.

12. Catanese, J. & Kress, L. F. (1984) *Biochim. Biophys. Acta* 789, 37-43.

13. Karmali, M. A., Petric, M., Steele, B. T. & Lim, C. (1983) *Lancet* 1, 619-620.

14. Caprioli, A., Luzzi, I., Gianviti, A., Russmann, H. & Karch, H. (1995) *J. Med. Microbiol.* 43, 348-353.

15. Jiang, W. & Bond, J. S. (1992) *FEBS Lett* 312, 110-114.

16. Jung, C.-M., Matsushita, O., Katayama, S., Minami, J., Sakurai, J. & Okabe, A. (1999) *J. Bact.* 181, 2816-2822.

17. Frank, M. M., and L. F. Fries. (1989) Complement. In Fundamental Immunology. W. E. Paul, editor. Raven Press, New York.

18. Pensky, J., and H. G. Schwick. (1969) Human serum inhibitor of C'1 esterase: identity with alpha-2-neuraminoglycoprotein. *Science* 163:698-699.

19. Weiler, J. M., M. R. Daha, K. F. Austen, and D. T. Fearon. (1976) Control of the amplification convertase of complement by the plasma protein beta1H. *Proc Natl Acad Sci USA* 73:3268-3272.

20. Gigli, I., T. Fujita, and V. Nussenzweig. (1979) Modulation of the classical pathway C3 convertase by plasma proteins C4 binding protein and C3b inactivator. *Proc Natl Acad Sci USA* 76:6596-6600.

21. van den Berg, R. H., M. Faber-Krol, L. A. van Es, and M. R. Daha. (1995) Regulation of the function of the first component of complement by human C1q receptor. *Eur J Immunol* 25:2206-2210.

22. Potempa, J., E. Korzus, and J. Travis. (1994) The serpin superfamily of proteinase inhibitors: structure, function and regulation. *J Biol Chem* 269:15957-15960.

23. Huntington, J. A., R. J. Read, and R. W. Carrell. (2000) Structure of a serpin-protease complex shows inhibition by deformation. *Nature* 407:923-926.

24. Sim, R. B., A. Reboul, G. J. Arlaud, C. L. Villiers, and M. G. Colomb. (1979) Interaction of I125-labelled complement subcomponents C1r and C1s with protease inhibitors in plasma. *FEBS Lett* 97:111-115.

25. Chan, J. Y., C. E. Burrowes, F. M. Habal, and H. Z. Movat. (1977) The inhibition of activated factor XII (Hageman factor) by antithrombin III: the effect of other plasma proteinase inhibitors. *Biochim Biophys Res Commun* 74:150-158.

26. Schapira, M., C. F. Scott, and R. W. Colman. (1982) Contribution of plasma protease inhibitors to the inactivation of kallikrein in plasma. *J Clin Invest* 69:462-468.

27. Van den Graaf, F., J. A. Koedam, and B. N. Bouma. (1983) Inactivation of kallikrein in human plasma. *J Clin Invest* 71:149-158.

28. Pixley, R. A., M. Schapira, and R. W. Colman. (1985) The regulation of human factor XIIa by plasma proteinase inhibitors. *J Biol Chem* 260:1723-1729.

29. Wuillemin, W. A., M. Minnema, J. C. Meijers, D. Roem, A. J. M. Eerenberg, J. H. Nuijens, J. W. ten Cate, and C. E. Hack. (1995) Inactivation of factor XIa in human plasma assessed by measuring factor XIa-protease inhibitor complexes: Major role of C1-inhibitor. *Blood* 85:1517-1526.

30. Jiang, H., E. Wagner, H. Zhang, and M. M. Frank. (2001) Complement 1 Inhbitor is a regulator of the alternative complement pathway. *J Exp Med* 194:1609-1616.

31. Coutinho, M., K. S. Aulak, and A. E. Davis. (1994) Functional analysis of the serpin domain of C1 inhibitor. *J Immunol* 153:3648-3654.

32. Patston, P. A., M. Qi, J. A. Schifferli, and M. Schapira. (1995) The effect of cleavage by a Crotalus atrox alpha-proteinase fraction on the properties of C1-inhibitor. *Toxicon* 33:53-61.

33. Wuillemin, W. A., E. Eldering, F. Citarella, C. P. de Ruig, J. W. ten Cate, and C. E. Hack. (1996) Modulation of contact system proteases by glycosaminoglycans. Selective enhancement of the inhibition of factor XIa. *J Biol Chem* 271:12913-12918.

34. Caldwell, E. E., A. M. Andreasen, M. A. Blietz, J. N. Serrahn, V. VanderNoot, Y. Park, G. Yu, R. J. Linhardt, and J. M. Weiler. 1999. Heparin binding and augmentation of C1 inhibitor activity. *Arch Biochem Biophys* 361:215-222.

35. Schmaier, A. H., S. C. Murray, G. D. Heda, A. Farber, A. Kuo, K. McCrae, and D. B. Cines. (1989) Synthesis and expression of C1 inhibitor by human umbilical vein endothelial cells. *J Biol Chem* 264:18173-18179.

36. Schmaier, A. H., S. Amenta, T. Xiong, G. D. Heda, and A. M. Gewirtz. (1993) Expression of platelet C1 inhibitor. *Blood* 82:465-474.

37. Frankel, G., A. D. Phillips, I. Rosenshine, G. Dougan, J. B. Kaper, and S. Knutton. (1998) Enteropathogenic and enterohaemorrhagic *Escherichia coli*: more subversive elements. *Mol Microbiol* 30:911-921.

38. Nataro, J. P., and J. B. Kaper. (1998) Diarrheagenic *Escherichia coli*. *Clin Microbiol Rev* 11: 142-201.

39. Lathem, W. W., T. E. Grys, S. E. Witowski, A. G. Torres, J. B. Kaper, P. I. Tarr, and R. A. Welch. (2002) StcE, a metalloprotease secreted by *Escherichia coli* O157:H7, specifically cleaves C1 esterase inhibitor. *Mol Microbiol* 45:277-288.

40. Lathem, W. W., T. Bergsbaken, S. E. Witowski, N. T. Perna, and R. A. Welch. (2003) Acquisition of StcE, a C1 esterase inhibitor-specific metalloprotease, during the evolution of *Escherichia coli* O157:H7. *J Infect Dis*: in press.

41. Paton, A. W., and J. C. Paton. (2002) Reactivity of convalescent-phase hemolytic-uremic syndrome patient sera with the megaplasmid-encoded TagA protein of shiga toxigenic *Escherichia coli* O157. *J Clin Microbiol* 40:1395-1399.

42. Mayer, M. M. (1961) Experimental Immunochemistry. E. A. Kabat and M. M. Mayer, editors. Thomas, Springfield, Ill.

43. Harlow, E., and D. Lane. (1988) Antibodies: a laboratory manual. Cold Spring Harbor Laboratory Press, Cold Spring Harbor.

44. Patston, P. A. (2003) Personal communication.

45. de Agostini, A., M. Schapira, Y. T. Wachtfogel, R. W. Colman, and S. Carrel. (1985) Human plasma kallikrein and C1 inhibitor form a complex possessing an epitope that is not detectable on the parent molecules: demonstration using a monoclonal antibody. *Proc Natl Acad Sci USA* 82:5190-5193.

46. Patston, P. A., and M. Schapira. (1997) Regulation of C1-inhibitor function by binding to type IV collagen and heparin. *Biochem Biophys Res Commun* 230:597-601.

47. Hauert, J., P. A. Patston, and M. Schapira. (2000) C1 inhibitor cross-linking by tissue transglutaminase. *J Biol Chem* 275:14558-14562.

48. Matsunami, K., S. Miyagawa, M. Yamada, M. Yoshitatsu, and R. Shirakura. (2000) A surface-bound form of human C1 esterase inhibitor improves xenograft rejection. *Transplantation* 69:749-755.

49. Bergamaschini, L., G. Gobbo, S. Gatti, L. Caccamo, P. Prato, M. Maggioni, P. Braidotti, R. Di Stefano, and L. R. Fassati. (2001) Endothelial targeting with C1-inhibitor reduces complement activation in vitro and during ex vivo reperfusion of pig liver. *Clin Exp Immunol* 126:412-420.

50. Minta, J. O. (1981) The role of sialic acid in the functional activity and the hepatic clearance of C1-INH. *J Immunol* 126:245-249.

51. Storm, D., J. Herz, P. Trinder, and M. Loos. (1997) C1 inhibitor-C1s complexes are internalized and degraded by the low density lipoprotein receptor-related protein. *J Biol Chem* 272:31043-31050.

52. te Loo, D. M., L. A. Monnens, T. J. van Der Velden, M. A. Vermeer, F. Preyers, P. N. Demacker, L. P. van Den Heuvel, and V. W. van Hinsbergh. (2000) Binding and transfer of verocytotoxin by polymorphonuclear leukocytes in hemolytic uremic syndrome. *Blood* 95:3396-3402.

53. te Loo, D. M., V. W. van Hinsbergh, L. P. van Den Heuvel, and L. A. Monnens. (2001) Detection of verocytotoxin bound to circulating polymorphonuclear leukocytes of patients with hemolytic uremic syndrome. *J Am Soc Nephrol* 12:800-806.

54. Cai, S., and A. E. Davis, 3rd. (2003) Complement regulatory protein C1 inhibitor binds to selectins and interferes with endothelial-leukocyte adhesion. *J Immunol* 171: 4786-4791.

55. Cooper, N. R. (1991) Complement evasion strategies of microorganisms. *Immunol Today* 12:327-331.

56. Frank, M. M. (1992) The mechanism by which microorganisms avoid complement attack. *Curr Opin Immunol* 4:14-19.

57. Molla, A., T. Akaike, and H. Maeda. (1989) Inactivation of various proteinases inhibitors and the complement system in human plasma by the 56-kilodalton proteinase from *Serratia marcescens*. *Infect Immun* 57:1868-1871.

58. Oda, T., Y. Kojima, T. Akaike, S. Ijiri, A. Molla, and H. Maeda. (1990) Inactivation of chemotactic activity of C5a by the serratial 56-kilodalton protease. *Infect Immun* 58:1269-1272.

59. Hong, Y. Q., and B. Ghebrehiwet. (1992) Effect of *Pseudomonas aeruginosa* elastase and alkaline protease on serum complement and isolated components C1q and C3. *Clin Immunol Immunopathol* 62:133-138.

60. Hellwage, J., T. Meri, T. Heikkila, A. Alitalo, J. Panelius, P. Lahdenne, I. J. Seppala, and S. Meri. (2001) The complement regulator factor H binds to the surface protein OspE of *Borrelia burgdorferi*. *J Biol Chem* 276:8427-8435.

61. Berggard, K., E. Johnsson, E. Morfeldt, J. Persson, M. Stalhammar-Carlemalm, and G. Lindahl. (2001) Binding of human C4BP to the hypervariable region of M protein: a molecular mechanism of phagocytosis resistance in *Streptococcus pyogenes*. *Mol Microbiol* 42:539-551.

62. Them, A., L. Stenberg, B. Dahlback, and G. Lindahl. (1995) Ig-binding surface proteins of *Streptococcus pyogenes* also bind human C4b-binding protein (C4BP), a regulatory component of the complement system. *J Immunol* 154:375-386.

63. Plunkett, G., 3rd, D. J. Rose, T. J. Durfee, and F. R. Blattner. (1999) Sequence of Shiga toxin 2 phage 933W from *Escherichia coli* O157:H7: Shiga toxin as a phage late-gene product. *J Bacteriol* 181:1767-1778.

64. Donnenberg, M. S. & Nataro, J. P. (1992) *Methods in Enzymology*, 253, 324-327.

65. Knutton, S., et al. (1989) *Infection and Immunology*, 1290-1298.

66. Boucher, R. C. (2002) *Advanced Drug Delivery Reviews*, 54, 1359-1371.

67. Eriksson, K., et al. (2003) *Infection and Immunity*, 71(4):1740-1747.

68. Elson, C. & Ealding, W. (1984) *Journal of Immunology*, 133(6): 2892-2897.

69. Li, Y., et al. (2000) *Infection and Immunity*, 68(9): 5090-5095.

70. Shreedhar, V., et al., (2003) *Infection and Immunity*, 71(1):504-509.

71. Dean-Nystrom, E, et al. (2002) *Infection and Immunity*. 70(5): 2414-2418.

72. Pierce, N. F. (Mar. 20, 1978) The Role of Antigen Form and Function in the Primary and Secondary Intestinal Immune Responses to Cholera Toxin and Toxoid in Rats, *J. Exp. Med*, The Rockefeller University Press, 195-206.

73. Judge, N., et al. (2004) *Infection and Immunity*, 72(1): 168-175.

74. Potter, A., et al. (2004) *Vaccine*, 22, 362-369.

75. Lee, G. et al. (1998) *Jouirnal of Cell Science*, 111, 3167-3177.

76. Datsenko and Warner (2000) *PNAS* 97, 6640-6645.

77. DeLoney, et al. (2002) *J. Bacteriology*, 184(18) 5121-5129.

What is claimed is:

1. A method of reducing complement-mediated disruption of cells comprising contacting the cells with a purified polypeptide comprising amino acid residues 24-886 of SEQ ID NO: 2 or SEQ ID NO: 19 (StcE E435D) in an amount effective to reduce complement-mediated disruption relative to that of cells not contacted with the purified polypeptide.

2. The method of claim 1, further comprising contacting the cells with exogenous C1-INH.

3. The method of claim 1, wherein the cells are within a tissue, and wherein the reduction in complement mediated disruption is effective to reduce inflammation of the tissue.

* * * * *

UNITED STATES PATENT AND TRADEMARK OFFICE
CERTIFICATE OF CORRECTION

PATENT NO.         : 7,264,922 B2                                    Page 1 of 1
APPLICATION NO.    : 11/294087
DATED              : September 4, 2007
INVENTOR(S)        : Rodney A. Welch et al.

It is certified that error appears in the above-identified patent and that said Letters Patent is hereby corrected as shown below:

Cover page, item (75) Inventors:   add --Laura Walters, Monona, WI (US)--

Signed and Sealed this

Fourteenth Day of April, 2009

JOHN DOLL
*Acting Director of the United States Patent and Trademark Office*